(12) United States Patent
Uchikawa et al.

(10) Patent No.: US 8,552,037 B2
(45) Date of Patent: *Oct. 8, 2013

(54) TRICYCLIC COMPOUND AND PHARMACEUTICAL USE THEREOF

(71) Applicant: Takeda Pharmaceutical Company Limited, Osaka (JP)

(72) Inventors: Osamu Uchikawa, Kanagawa (JP); Tatsuki Koike, Kanagawa (JP); Yasutaka Hoashi, Kanagawa (JP); Takafumi Takai, Kanagawa (JP)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/657,956

(22) Filed: Oct. 23, 2012

(65) Prior Publication Data
US 2013/0079374 A1    Mar. 28, 2013

Related U.S. Application Data

(62) Division of application No. 13/047,363, filed on Mar. 14, 2011, now Pat. No. 8,349,879, and a division of application No. 12/305,560, filed as application No. PCT/JP2007/062645 on Jun. 18, 2007, now Pat. No. 8,030,337.

(30) Foreign Application Priority Data

Jun. 19, 2006   (JP) .................................. 2006-168518

(51) Int. Cl.
| | | |
|---|---|---|
| *A61K 31/428* | (2006.01) | |
| *A61K 31/423* | (2006.01) | |
| *C07D 277/60* | (2006.01) | |
| *C07D 263/52* | (2006.01) | |

(52) U.S. Cl.
USPC ............ 514/366; 514/375; 548/217; 548/150

(58) Field of Classification Search
USPC .......................... 514/375, 366; 548/217, 150
See application file for complete search history.

(56) References Cited

U.S. PATENT DOCUMENTS

| | | | |
|---|---|---|---|
| 4,877,876 A | 10/1989 | Tsuji et al. | |
| 5,276,051 A | 1/1994 | Lesieur et al. | |
| 5,596,019 A | 1/1997 | Mattson et al. | |
| 5,654,325 A | 8/1997 | Flaugh | |
| 5,753,709 A | 5/1998 | Keavy et al. | |
| 5,843,986 A | 12/1998 | Lesieur et al. | |
| 5,889,031 A | 3/1999 | Keavy et al. | |
| 6,034,239 A | 3/2000 | Ohkawa et al. | |
| 6,180,657 B1 | 1/2001 | Flaugh | |
| 6,262,095 B1 | 7/2001 | Boutherin-Falson et al. | |
| 6,569,894 B1 | 5/2003 | Takaki et al. | |
| 8,030,337 B2 * | 10/2011 | Uchikawa et al. ............ 514/375 |
| 8,236,837 B2 * | 8/2012 | Uchikawa et al. ............ 514/375 |
| 8,349,879 B2 * | 1/2013 | Uchikawa et al. ............ 514/375 |
| 2003/0216456 A1 | 11/2003 | Takaki et al. | |
| 2005/0197365 A1 | 9/2005 | Sterling et al. | |
| 2006/0223877 A1 | 10/2006 | Zemlan | |

FOREIGN PATENT DOCUMENTS

| | | |
|---|---|---|
| EP | 1 214 944 A1 | 6/2002 |
| EP | 1 334 732 A1 | 8/2003 |
| EP | 0 885 210 B2 | 6/2008 |
| JP | 6-199784 A | 7/1994 |
| JP | 8-239377 A | 9/1996 |
| JP | 2002-212063 A | 7/2002 |
| RU | 94040886 A1 | 9/1996 |
| RU | 94041028 A1 | 9/1996 |
| RU | 96111003 A | 9/1998 |
| RU | 2178791 C2 | 6/2000 |
| RU | 2146140 C1 | 10/2000 |
| RU | 2160101 C2 | 12/2000 |
| RU | 2162076 C2 | 1/2001 |
| RU | 98113147 A | 6/2006 |
| RU | 2007140242 A | 10/2007 |
| SU | 1609449 A3 | 11/1990 |

OTHER PUBLICATIONS

Berge et al. Pharmaceutical Salts J. Pharm. Sci. 1997, vol. 66, pp. 1-19.

Decision on Grant issued in corresponding Russian patent application No. 2009101299/01(001597) dated Feb. 15, 2012.

Dorwald, F. Zaragoza. Side Reactions in Organic Synthesis: A Guide to Successful Synthesis Design, Weinheim: Wiley-VCHVerlag GmbH & Co. KGaA, 2005, Preface.

Georgian Search Report corresponding to Georgian Patent Application No. AP 2007 011069 dated May 21, 2010.

Guigen et al., "Catalytic Asymmetric Aminohydroxylation (AA) of Olefins", Angew. Chem. Int. Ed. Engl. 1996, vol. 35, 451-454.

Larrow et al. Org. Synth, Coll. vol. 10, p. 29 (2004); vol. 76, p. 46 (1999).

Li-Qiang Sun et al., "Design and synthesis of benzoxazole derivatives as novel melatoninergic ligands", Bioorganic and Medical Chemistry Letters 14, 2004, pp. 1197-1200.

(Continued)

*Primary Examiner* — Joseph Kosack
*Assistant Examiner* — Matthew Coughlin
(74) *Attorney, Agent, or Firm* — Sughrue Mion, PLLC

(57) ABSTRACT

The present invention provides a compound represented by the formula

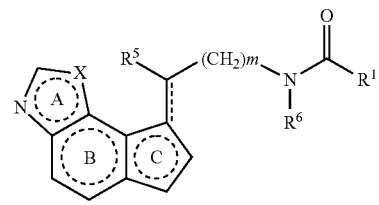

which is useful as an agent for the prophylaxis or treatment of diseases related to the action of melatonin, or a salt thereof and the like.

17 Claims, No Drawings

(56) References Cited

OTHER PUBLICATIONS

Li-Quang Sun et al., "Synthesis and structure-activity relationship of novel benzoxazole derivatives as melatonin receptor agonists", Bioorganic & Medicincal Chemistry Letters 14, 2004, pp. 3799-3802.
Mashkovsky, M.D. "Medicaments", Moscow, "Meditsina", 2001, part 1, pp. 6-7.
Rautio et al. Prodrugs: design and clinical applications Nature Reviews Drug Discovery 2008, vol. 7, pp. 255-270.
Russian Office Action issued in Russian Patent Application No. 2009101299 dated Jan. 18, 2011.
Smith, D. A. Do prodrugs deliver? Current Opinion in Drug Discovery & Development 2007, vol. 10, 550-559.
Testa, B. Prodrugs: bridging pharmacodynamic/pharmacokinetic gaps Current Opinion in Chemical Biology 2009, vol. 13, pp. 338-344.
Turek et al. "Melatonin, sleep, and circadian rhythms: rationale for development of specific melatonin agonists", Sleep Medicine, 2004, vol. 5, p. 523-532.
Uchikawa, O., Synthesis of a Novel Series of Tricyclic Indan Derivatives as Melatonin Receptor Agonists, J. Med. Chem, 2002, 45, pp. 4222-4239.
Wang et al. Drug Delivery: Principles and Applications, 2005 John Wiley & Sons, Inc. Publication, Section 8.3, pp. 136-137.
Colombian Office Action dated Sep. 18, 2012, issued in corresponding Colombian Patent Application No. 09003953.
Bohm et al., "Scaffold hopping", Drug Discovery Today: Technologies, vol. 1, No. 3, 2004, pp. 217-224.

* cited by examiner

TRICYCLIC COMPOUND AND PHARMACEUTICAL USE THEREOF

This is a Divisional of Application Ser. No. 13/047,363 filed Mar. 14, 2011, which is a Divisional of Application Ser. No. 12/305,560 filed Dec. 18, 2008 which is a National Stage Application of PCT/JP2007/062645 filed Jun. 18, 2007, claiming priority based on Japanese Patent Application No. 168518/2006 filed Jun. 19, 2006, the contents of each of which are incorporated herein by reference in their entirety.

TECHNICAL FIELD

The present invention relates to a tricyclic compound having superior affinity for melatonin receptor, and useful as an agent for the prophylaxis or treatment of a disease related to the action of melatonin.

BACKGROUND OF THE INVENTION

Melatonin (N-acetyl-5-methoxytryptamine), which is a hormone synthesized and secreted principally in the pineal gland, increases in dark environments and decreases in light environments. Melatonin acts suppressively on pigment cells and the female gonads, and acts as a synchronous factor of biological clock while taking part in transmittance of photoperiodic code. Therefore, melatonin is expected to be usable for the treatment of diseases related to melatonin activity, such as reproductive and endocrinic disorders, sleep-awake rhythm disorders, jet-lag syndrome, various disorders related to aging and the like. It has been clarified that the production amount of melatonin decreases with aging and there is a report documenting that retention of the production amount of melatonin could prevent aging itself [Ann. N.Y. Acad. Sci., Vol. 719, pp. 456-460, (1994)]. However, since melatonin is easily metabolized by metabolic enzymes in vivo [Clinical Examinations, Vol. 38, No. 11, pp. 282-284 (1994)]. Therefore, melatonin is not entirely suitable as a drug.

US2003/0216456 discloses a compound represented by the formula:

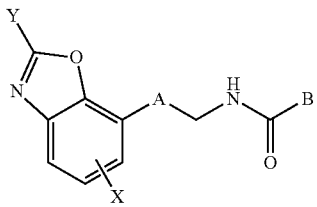

wherein A is $C_{1-4}$ alkylene or 1,2 disubstituted cyclopropyl; B is $C_{1-6}$ alkyl, $C_{3-6}$ cycloalkyl, $C_{1-6}$ alkoxy, or $C_{1-4}$ alkylamino; X is hydrogen, halogen, $C_{2-4}$ alkenyl, $C_{1-6}$ alkyl, furyl, or phenyl optionally substituted with halogen, $C_{1-6}$ alkoxy or haloalkyl; and Y is hydrogen, phenyl, or $C_{1-6}$ alkyl optionally substituted with phenyl, which has an affinity for melatonin receptor and is useful as a therapeutic agent for circadian rhythm-related disorders. Moreover, a compound similar to the above-mentioned compound is also disclosed in Bioorg. Med. Chem. Lett. Vol. 14, pp. 1197-1200 (2004) and Bioorg. Med. Chem. Lett. Vol. 14, pp. 3799-3802 (2004).

U.S. Pat. No. 6,569,894 discloses a compound of the formula:

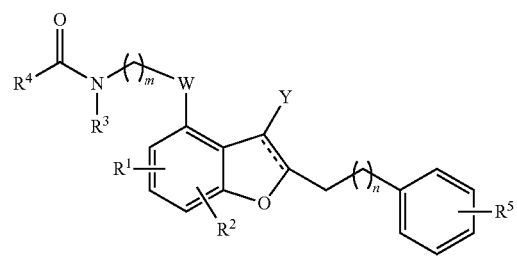

wherein the dashed line represents a single or double bond; $R^1$ and $R^2$ are each independently hydrogen or halogen; $R^3$ is hydrogen or $C_{1-4}$ alkyl; $R^4$ is $C_{1-4}$ alkyl, $C_{3-6}$ cycloalkyl, $C_{1-3}$ haloalkyl, $C_{2-6}$ alkenyl, $C_{1-4}$ alkoxy, $C_{1-2}$ trifluoromethylalkyl or $C_{1-4}$ alkylamino; $R^5$ is hydrogen, halogen, $C_{1-4}$ alkyl or $C_{1-4}$ alkoxy; Y is hydrogen or halogen; W is ethylene or 1,2 disubstituted cyclopropyl group; m is 1 or 2; and n is 1 to 9, which has an affinity for melatonin receptor and is useful as a therapeutic agent for circadian rhythm-related disorders.

U.S. Pat. No. 6,034,239 discloses a compound represented by the formula:

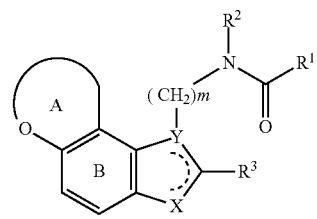

wherein $R^1$ represents an optionally substituted hydrocarbon group, an optionally substituted amino group or an optionally substituted heterocyclic group; $R^2$ represents a hydrogen atom or an optionally substituted hydrocarbon group; $R^3$ represents a hydrogen atom, an optionally substituted hydrocarbon group or an optionally substituted heterocyclic group; X represents $CHR^4$, $NR^4$, O or S wherein $R^4$ represents a hydrogen atom or an optionally substituted hydrocarbon group; Y represents C, CH or N, provided that when X is $CH_2$, Y is C or CH; ----- represents a single bond or a double bond; ring A represents an optionally substituted 5- to 7-membered oxygen-containing heterocyclic ring; ring B represents an optionally substituted benzene ring; and m represents an integer of 1 to 4, or a salt thereof, which has an affinity for melatonin receptor and is useful as a therapeutic agent for sleep disorder.

DISCLOSURE OF THE INVENTION

Melatonin agonists having different structures from that of melatonin, and having superior affinity for melatonin receptor, superior intracerebral mobility and superior metabolic stability are expected to be more effective for the treatment of sleep disorder and the like than melatonin. While the above-mentioned compounds and the like have been reported as melatonin agonists, the development of a novel compound, which is different from the above-mentioned known compounds in the chemical structure, has superior agonistic activity for melatonin receptor, and is useful as a pharmaceutical product, is desired.

The present inventors have conducted various studies and first succeeded in the production of a novel compound represented by the following formula (I) and a salt thereof. They have further found that the compound and a salt thereof unexpectedly have superior properties as melatonin agonists and are useful as pharmaceutical agents and, based on these findings, completed the present invention.

Accordingly, the present invention relates to
(1) a compound represented by the formula:

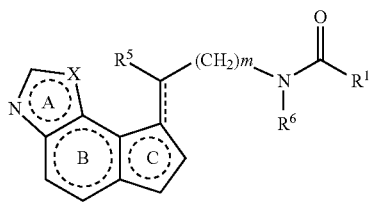

(I)

wherein
$R^1$ is a hydrocarbon group optionally having substituent(s), amino optionally having substituent(s), hydroxy optionally having a substituent or a heterocyclic group optionally having substituent(s);
$R^5$ is a hydrogen atom, a halogen atom, a hydrocarbon group optionally having substituent(s), amino optionally having substituent(s), hydroxy optionally having a substituent or mercapto optionally having a substituent;
$R^6$ is a hydrogen atom or a hydrocarbon group optionally having substituent(s);
X is an oxygen atom or a sulfur atom;
m is 0, 1 or 2;
ring A is a 5-membered ring optionally having substituent(s);
ring B is a 6-membered ring optionally having substituent(s);
ring C is a 5-membered ring optionally having substituent(s); and
___ shows a single bond or a double bond, or a salt thereof [hereinafter sometimes to be abbreviated as compound (I)];
(2) the compound of the aforementioned (1), which is represented by the formula:

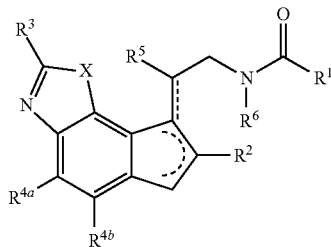

(I')

wherein
$R^2$ is a hydrogen atom, a halogen atom, a hydrocarbon group optionally having substituent(s) or a heterocyclic group optionally having substituent(s);
$R^3$ is a hydrogen atom, a hydrocarbon group optionally having substituent(s), amino optionally having substituent(s), hydroxy optionally having a substituent, mercapto optionally having a substituent or a heterocyclic group optionally having substituent(s);
$R^{4a}$ and $R^{4b}$ are the same or different and each is a hydrogen atom, a halogen atom, a hydrocarbon group optionally having substituent(s), amino optionally having substituent(s), hydroxy optionally having a substituent or mercapto optionally having a substituent;
and other symbols are as defined in the aforementioned (1);
(3) the compound of the aforementioned (1) or (2), which is represented by the formula:

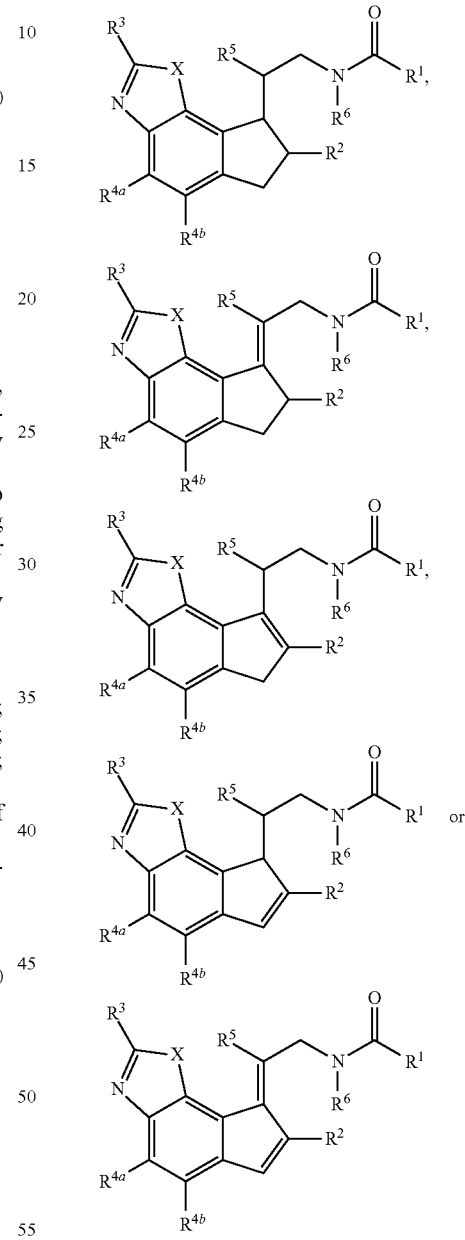

wherein $R^2$, $R^3$, $R^{4a}$ and $R^{4b}$ are as defined in the aforementioned (2), and other symbols are as defined in the aforementioned (1);

(4) the compound of the aforementioned (1) or (2), wherein $R^1$ is $C_{1-6}$ alkyl optionally having substituent(s), $C_{3-6}$ cycloalkyl optionally having substituent(s) or $C_{2-6}$ alkenyl optionally having substituent(s);

(5) the compound of the aforementioned (1) or (2), wherein $R^5$ is a hydrogen atom or $C_{1-6}$ alkyl optionally having substituent(s);

(6) the compound of the aforementioned (1) or (2), wherein $R^6$ is a hydrogen atom or $C_{1-6}$ alkyl optionally having substituent(s);

(7) the compound of the aforementioned (1), wherein m is 1;

(8) the compound of the aforementioned (1), wherein ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent;

(9) the compound of the aforementioned (1), wherein ring B is a 6-membered ring optionally having 1 or 2 substituents selected from a halogen atom, a hydrocarbon group optionally having substituent(s), amino optionally having substituent(s), hydroxy optionally having a substituent, mercapto optionally having a substituent and a heterocyclic group optionally having substituent(s);

(10) the compound of the aforementioned (1), wherein ring C is a 5-membered ring optionally having 1 or 2 substituents selected from a halogen atom, a hydrocarbon group optionally having substituent(s), hydroxy optionally having a substituent and a heterocyclic group optionally having substituent(s);

(11) the compound of the aforementioned (2), wherein $R^2$ is a hydrogen atom, a hydrocarbon group optionally having substituent(s) or a heterocyclic group optionally having substituent(s);

(12) the compound of the aforementioned (2), wherein $R^3$ is a hydrogen atom, $C_{1-6}$ alkyl optionally having substituent(s), $C_{2-6}$ alkenyl optionally having substituent(s) or amino optionally having substituent(s);

(13) the compound of the aforementioned (2), wherein $R^{4a}$ and $R^{4b}$ are the same or different and each is a hydrogen atom, a halogen atom, hydroxy optionally having a substituent or $C_{1-6}$ alkyl optionally having substituent(s);

(14) the compound of the aforementioned (2), wherein $R^1$ is $C_{1-6}$ alkyl optionally having substituent(s), $C_{3-6}$ cycloalkyl optionally having substituent(s) or $C_{2-6}$ alkenyl optionally having substituent(s);

$R^2$ is a hydrogen atom, a hydrocarbon group optionally having substituent(s) or a heterocyclic group optionally having substituent(s);

$R^3$ is a hydrogen atom, $C_{1-6}$ alkyl optionally having substituent(s), $C_{2-6}$ alkenyl optionally having substituent(s) or amino optionally having substituent(s);

$R^{4a}$ and $R^{4b}$ are the same or different and each is a hydrogen atom, a halogen atom, hydroxy optionally having a substituent or $C_{1-6}$ alkyl optionally having substituent(s);

$R^5$ is a hydrogen atom or $C_{1-6}$ alkyl optionally having substituent(s); and $R^6$ is a hydrogen atom or $C_{1-6}$ alkyl optionally having substituent(s);

(15) the compound of the aforementioned (2), wherein $R^1$ is $C_{1-6}$ alkyl optionally having substituent(s);

$R^2$ is a hydrogen atom;

$R^3$ is a hydrogen atom or $C_{1-6}$ alkyl optionally having substituent(s);

$R^{4a}$ and $R^{4b}$ are the same or different and each is a hydrogen atom or a halogen atom;

$R^5$ is a hydrogen atom or $C_{1-6}$ alkyl optionally having substituent(s); and $R^6$ is a hydrogen atom;

(16) the compound of the aforementioned (1), which is represented by the formula:

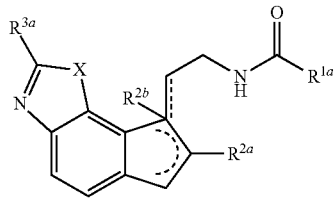

wherein
$R^{1a}$ is (a) $C_{1-6}$ alkyl optionally having 1 to 3 substituents selected from $C_{1-6}$ alkyl-carbonyloxy, hydroxy and a halogen atom, (b) $C_{3-6}$ cycloalkyl, (c) phenyl or (d) mono- or di-$C_{1-6}$ alkylamino;

$R^{2a}$ is a hydrogen atom or $C_{1-6}$ alkyl;

$R^{2b}$ is a hydrogen atom or hydroxy;

$R^{3a}$ is (a) a hydrogen atom, (b) $C_{1-6}$ alkyl optionally having 1 to 3 substituents selected from phenyl, hydroxy, a halogen atom, $C_{1-6}$ alkyl-carbonyl, $C_{7-13}$ aralkyloxy and pyridyl, (c) $C_{3-6}$ cycloalkyl, (d) phenyl, (e) $C_{1-6}$ alkoxy, (f) mercapto, (g) $C_{1-6}$ alkylthio or (h) mono- or di-$C_{1-6}$ alkylamino;

(17) N-[2-(2-methyl-6,7-dihydro-8H-indeno[5,4-d][1,3]oxazol-8-ylidene)ethyl]acetamide, N-[2-(2-methyl-6H-indeno[5,4-d][1,3]oxazol-8-yl)ethyl]acetamide, N-[2-(2-methyl-6,7-dihydro-8H-indeno[5,4-d][1,3]oxazol-8-ylidene)ethyl]propionamide, N-{2-[2-(4-phenylbutyl)-6,7-dihydro-8H-indeno[5,4-d][1,3]oxazol-8-ylidene]ethyl}acetamide, N-[2-(2-methyl-6,7-dihydro-8H-indeno[5,4-d][1,3]thiazol-8-ylidene)ethyl]acetamide, N-[2-(2-methyl-7,8-dihydro-6H-indeno[5,4-d][1,3]oxazol-8-yl)ethyl]acetamide, (R)-N-[2-(2-methyl-7,8-dihydro-6H-indeno[5,4-d][1,3]oxazol-8-yl)ethyl]acetamide, (S)-N-[2-(2-methyl-7,8-dihydro-6H-indeno[5,4-d][1,3]oxazol-8-yl)ethyl]acetamide, N-[2-(2-methyl-7,8-dihydro-6H-indeno[5,4-d][1,3]oxazol-8-yl)ethyl]propionamide, (R)-N-[2-(2-methyl-7,8-dihydro-6H-indeno[5,4-d][1,3]oxazol-8-yl)ethyl]propionamide, (S)-N-[2-(2-methyl-7,8-dihydro-6H-indeno[5,4-d][1,3]oxazol-8-yl)ethyl]propionamide, N-[2-(2-methyl-7,8-dihydro-6H-indeno[5,4-d][1,3]thiazol-8-yl)ethyl]acetamide, (R)-N-[2-(2-methyl-7,8-dihydro-6H-indeno[5,4-d][1,3]thiazol-8-yl)ethyl]acetamide, (S)-N-[2-(2-methyl-7,8-dihydro-6H-indeno[5,4-d][1,3]thiazol-8-yl)ethyl]acetamide, N-[2-(2-ethyl-7,8-dihydro-6H-indeno[5,4-d][1,3]oxazol-8-yl)ethyl]acetamide, (R)-N-[2-(2-ethyl-7,8-dihydro-6H-indeno[5,4-d][1,3]oxazol-8-yl)ethyl]acetamide, (S)-N-[2-(2-ethyl-7,8-dihydro-6H-indeno[5,4-d][1,3]oxazol-8-yl)ethyl]acetamide, N-[2-(2-methoxy-7,8-dihydro-6H-indeno[5,4-d][1,3]oxazol-8-yl)ethyl]acetamide, (R)-N-[2-(2-methoxy-7,8-dihydro-6H-indeno[5,4-d][1,3]oxazol-8-yl)ethyl]acetamide, (S)-N-[2-(2-methoxy-7,8-dihydro-6H-indeno[5,4-d][1,3]oxazol-8-yl)ethyl]acetamide, or a salt thereof;

(18) a prodrug of the compound of the aforementioned (1);

(19) a pharmaceutical composition comprising the compound of the aforementioned (1) or a prodrug thereof;

(20) the pharmaceutical composition of the aforementioned (19), which is a melatonin receptor agonist;

(21) the pharmaceutical composition of the aforementioned (19), which is an agent for the prophylaxis or treatment of sleep disorder;

(22) a compound represented by the formula:

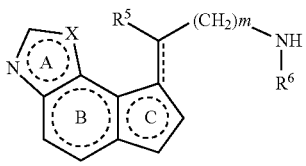

wherein each symbol is as defined in the aforementioned (1), or a salt thereof;

(23) the compound of the aforementioned (22), which is represented by the formula:

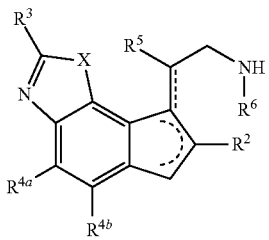

wherein $R^2$, $R^3$, $R^{4a}$ and $R^{4b}$ are as defined in the aforementioned (2), and other symbols are as defined in the aforementioned (1); and the like.

In the aforementioned formulas, the ring represented by

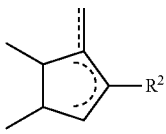

means

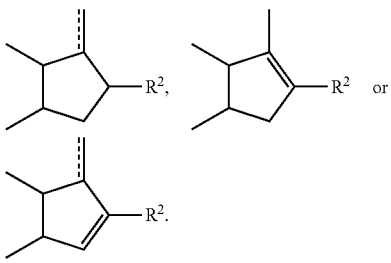

In the aforementioned formulas, the ring represented by

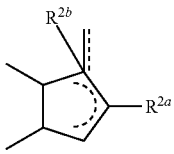

means

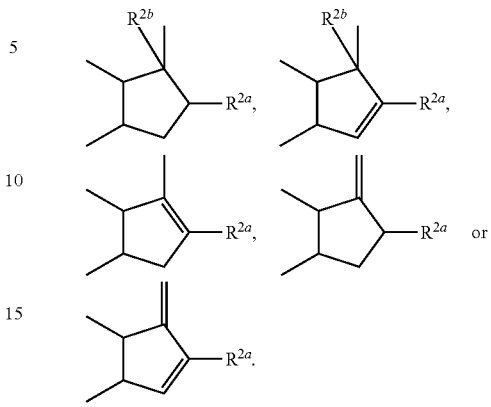

Since compound (I) of the present invention shows superior affinity for melatonin receptors, superior pharmacokinetics (e.g., metabolic stability) and the like, a clinically useful agent for the prophylaxis or treatment of diseases related to the action of melatonin in the living body can be provided.

As the "halogen atom" used in the present specification, fluorine, chlorine, bromine or iodine can be mentioned.

The term "optionally halogenated" used in the present specification means being optionally substituted by 1 to 5, preferably 1 to 3, halogen atoms.

As the "hydrocarbon group" of the term "hydrocarbon group optionally having substituent(s)" used in the present specification, for example, aliphatic hydrocarbon group, monocyclic saturated hydrocarbon group and aromatic hydrocarbon group and the like can be mentioned, with preference given to those having 1 to 16 carbon atoms. Specifically, for example, alkyl, alkenyl, alkynyl, cycloalkyl, aryl and the like are used.

The "alkyl" is preferably, for example, lower alkyl or the like, and, for example, $C_{1-6}$ alkyl such as methyl, ethyl, propyl, isopropyl, butyl, isobutyl, sec-butyl, tert-butyl, pentyl, hexyl etc., and the like are widely used.

The "alkenyl" is preferably, for example, lower alkenyl or the like, and, for example, $C_{2-6}$ alkenyl such as vinyl, 1-propenyl, allyl, isopropenyl, butenyl, isobutenyl etc., and the like are widely used.

The "alkynyl" is preferably, for example, lower alkynyl or the like, and, for example, $C_{2-6}$ alkynyl such as ethynyl, propargyl, 1-propynyl etc., and the like are widely used.

The "cycloalkyl" is preferably, for example, lower cycloalkyl or the like, and, for example, $C_{3-6}$ cycloalkyl such as cyclopropyl, cyclobutyl, cyclopentyl and cyclohexyl, and the like are widely used.

The "aryl" is preferably, for example, $C_{6-14}$ aryl such as phenyl, 1-naphthyl, 2-naphthyl, biphenylyl, 2-anthryl etc., or the like, more preferably $C_{6-10}$ aryl, and, for example, phenyl and the like are widely used.

As the substituent which the "hydrocarbon group" of the "hydrocarbon group optionally having substituent(s)" may have, for example, (1) halogen atom (e.g., fluorine, chlorine, bromine, iodine),
(2) nitro,
(3) cyano,
(4) lower alkyl optionally having substituent(s) (e.g., $C_{1-6}$ alkyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkyl such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl etc., and the like), (5) aryl optionally having substituent(s) (e.g., $C_{6-10}$ aryl optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl such as phenyl, naphthyl etc., and the like), (6) hydroxy, (7) alkylenedioxy (e.g., $C_{1-3}$ alkylenedioxy such as methylenedioxy, ethylenedioxy etc., and the like), (8) lower alkoxy optionally having substituent(s) (e.g., $C_{1-6}$ alkoxy optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkoxy such as methoxy, ethoxy, propoxy, isopropoxy, butoxy, isobutoxy, pentyloxy, hexyloxy, trifluoromethoxy etc., and the like), (9) aryloxy optionally having substituent(s) (e.g., $C_{6-10}$ aryloxy optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryloxy such as phenyloxy, naphthyloxy etc., and the like),

(10) lower alkanoyloxy optionally having substituent(s) (e.g., formyloxy; $C_{1-6}$ alkyl-carbonyloxy optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{1-6}$ alkyl-carbonyloxy such as acetyloxy, propionyloxy, butyryloxy, isobutyryloxy etc., and the like),

(11) arylcarbonyloxy optionally having substituent(s) (e.g., $C_{6-10}$ aryl-carbonyloxy optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl-carbonyloxy such as benzoyloxy, naphthoyloxy etc., and the like),

(12) carboxy,

(13) lower alkanoyl optionally having substituent(s) (e.g., $C_{1-6}$ alkyl-carbonyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like or formyl; for example, $C_{1-6}$ alkyl-carbonyl such as acetyl, propionyl etc., and the like),

(14) arylcarbonyl optionally having substituent(s) (e.g., $C_{6-10}$ aryl-carbonyl optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl-carbonyl such as benzoyl, naphthoyl etc., and the like),

(15) lower alkoxycarbonyl optionally having substituent(s) (e.g., $C_{1-6}$ alkoxy-carbonyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{1-6}$ alkoxy-carbonyl such as methoxycarbonyl, ethoxycarbonyl, propoxycarbonyl, butoxycarbonyl etc., and the like),

(16) aralkyloxycarbonyl optionally having substituent(s) (e.g., $C_{7-12}$ aralkyloxy-carbonyl optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{7-12}$ aralkyloxy-carbonyl such as benzyloxycarbonyl etc., and the like),

(17) carbamoyl,

(18) mono-lower alkylcarbamoyl optionally having substituent(s) (e.g., mono-$C_{1-6}$ alkyl-carbamoyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, mono-$C_{1-6}$ alkyl-carbamoyl such as methylcarbamoyl, ethylcarbamoyl etc., and the like),

(19) di-lower alkylcarbamoyl optionally having substituent(s) (e.g., di-$C_{1-6}$ alkyl-carbamoyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, di-$C_{1-6}$ alkyl-carbamoyl such as dimethylcarbamoyl, diethylcarbamoyl etc., and the like),

(20) arylcarbamoyl optionally having substituent(s) (e.g., $C_{6-10}$ aryl-carbamoyl optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl-carbamoyl such as phenylcarbamoyl, naphthylcarbamoyl etc., and the like),

(21) amino,

(22) mono-lower alkylamino optionally having substituent(s) (e.g., mono-$C_{1-6}$ alkylamino optionally having 1 to 5 substituents selected from halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, mono-$C_{1-6}$ alkylamino such as methylamino, ethylamino etc., and the like),

(23) di-lower alkylamino optionally having substituent(s) (e.g., di-$C_{1-6}$ alkylamino optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, di-$C_{1-6}$ alkylamino such as dimethylamino, diethylamino etc., and the like),

(24) 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s) (e.g., 3- to 6-membered cyclic amino optionally containing, besides a carbon atom and one nitrogen atom, 1 to 3 hetero atoms selected from a nitrogen atom, an oxygen atom and a sulfur atom, which optionally has 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like),

(25) lower alkylcarbonylamino optionally having substituent(s) (e.g., $C_{1-6}$ alkyl-carbonylamino optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkyl-carbonylamino such as acetylamino, trifluoroacetylamino etc., and the like),

(26) oxo,

(27) heterocyclic group optionally having substituent(s) (e.g., 5- or 6-membered heterocyclic group optionally containing, besides a carbon atom, 1 to 3 hetero atoms selected from a nitrogen atom, an oxygen atom and a sulfur atom, which optionally has 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, thienyl, furyl, pyrrolyl, pyrrolidinyl, oxazolyl, isoxazolyl, triazolyl, isothiazolyl, pyrazolyl, pyrazolidinyl, imidazolyl, imidazolinyl, triazolyl, tetrazolyl, pyridyl, pyrimidinyl, thiomorpholinyl, morpholinyl, piperidino, piperidyl, thiopyranyl, oxazinyl, triazinyl, piperazinyl, triazinyl, pyridazinyl, pyrazinyl and the like; preferably pyridyl and the like),

(28) mercapto,

(29) lower alkylthio (e.g., $C_{1-6}$ alkylthio such as methylthio, ethylthio, propylthio, isopropylthio, butylthio, sec-butylthio, tert-butylthio etc., and the like),

(30) arylthio (e.g., $C_{6-10}$ arylthio such as phenylthio, naphthylthio etc., and the like),

(31) lower alkylsulfinyl (e.g., $C_{1-6}$ alkylsulfinyl such as methylsulfinyl, ethylsulfinyl, propylsulfinyl, butylsulfinyl etc., and the like),

(32) arylsulfinyl (e.g., $C_{6-10}$ arylsulfinyl such as phenylsulfinyl, naphthylsulfinyl etc., and the like),

(33) lower alkylsulfonyl (e.g., $C_{1-6}$ alkylsulfonyl such as methylsulfonyl, ethylsulfonyl, propylsulfonyl, butylsulfonyl etc., and the like),

(34) arylsulfonyl (e.g., $C_{6-10}$ arylsulfonyl such as phenylsulfonyl, naphthylsulfonyl etc., and the like)

(35) sulfamoyl,

(36) mono-lower alkylsulfamoyl (e.g., mono-$C_{1-6}$ alkylsulfamoyl such as N-methylsulfamoyl, N-ethylsulfamoyl, N-propylsulfamoyl, N-isopropylsulfamoyl, N-butylsulfamoyl etc., and the like),

(37) di-lower alkylsulfamoyl (e.g., di-$C_{1-6}$ alkylsulfamoyl such as N,N-dimethylsulfamoyl, N,N-diethylsulfamoyl, N,N-dipropylsulfamoyl, N,N-dibutylsulfamoyl etc., and the like) and the like are used.

The "hydrocarbon group" of the "hydrocarbon group optionally having substituent(s)" may have 1 to 5, preferably 1 to 3, substituents selected from the aforementioned substituents (1)-(37) [hereinafter the group consisting of these (1)-(37) is sometimes to be abbreviated as "substituent group A"] at substitutable position(s) of the hydrocarbon group. When the number of substituents is two or more, each substituent may be the same or different.

As the substituent which the "hydrocarbon group" optionally has, preferably, 1 to 5 (preferably 1 to 3) substituents selected from (1) halogen atom, (2) nitro, (3) cyano, (4) hydroxy, (5) optionally halogenated $C_{1-6}$ alkyl, (6) optionally halogenated $C_{1-6}$ alkoxy, (7) $C_{7-13}$ aralkyloxy, (8) amino, (9) mono-$C_{1-6}$ alkylamino, (10) di-$C_{1-6}$ alkylamino, (11) carboxy, (12) $C_{1-6}$ alkyl-carbonyl, (13) $C_{1-6}$ alkoxy-carbonyl, (14) carbamoyl, (15) mono-$C_{1-6}$ alkyl-carbamoyl, (16) di-$C_{1-6}$ alkyl-carbamoyl, (17) $C_{6-10}$ aryl-carbamoyl, (18) $C_{6-10}$ aryl (e.g., phenyl), (19) $C_{6-10}$ aryloxy, (20) $C_{1-6}$ alkylcarbonylamino, (21) $C_{1-6}$ alkyl-carbonyloxy, (22) heterocyclic group (e.g., pyridyl and the like) and the like can be mentioned.

As the "heterocyclic group" of the term "heterocyclic group optionally having substituent(s)" used in the present specification, for example, a 5- to 14-membered (preferably 5- to 10-membered) (monocyclic, bicyclic or tricyclic, preferably monocyclic or bicyclic) heterocyclic group containing, besides a carbon atom, 1 to 4 (preferably 1 to 3) hetero atoms of one or two kinds selected from a nitrogen atom, an oxygen atom and a sulfur atom, can be mentioned. For example, a 5-membered ring group containing, besides a carbon atom, 1 to 4 hetero atoms selected from a nitrogen atom, an oxygen atom and a sulfur atom, such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 2- or 4-imidazolinyl, 1,2,3-triazolyl, 1,2,4-triazolyl, 1H- or 2H-tetrazolyl and the like; for example, a 6-membered ring group containing, besides a carbon atom, 1 to 4 hetero atoms selected from a nitrogen atom, an oxygen atom and a sulfur atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxazinyl, 1,4-thiazinyl, 1,3-thiazinyl, 1- or 2-piperazinyl, triazinyl, 3- or 4-pyridazinyl, pyrazinyl, N-oxido-3- or 4-pyridazinyl and the like; for example, a bicyclic or tricyclic fused ring group containing, besides a carbon atom, 1 to 4 hetero atoms selected from a nitrogen atom, an oxygen atom and a sulfur atom (preferably, a group formed by condensation of the aforementioned 5- or 6-membered ring with one or two 5- or 6-membered ring group(s) optionally containing, besides a carbon atom, 1 to 4 hetero atoms selected from a nitrogen atom, an oxygen atom and a sulfur atom), such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl and the like; and the like are used. Of these, a 5- to 7-membered (preferably 5- or 6-membered) heterocyclic group containing, besides a carbon atom, 1 to 3 hetero atoms selected from a nitrogen atom, an oxygen atom and a sulfur atom is preferable.

As the substituent that the "heterocyclic group" of the "heterocyclic group optionally having substituent(s)" may have, (i) the aforementioned "hydrocarbon group optionally having substituent(s)", (ii) the groups recited as examples of the substituents that the "hydrocarbon group optionally having substituent(s)" may have, and the like can be mentioned. Particularly preferably, for example, (1) halogen atom (e.g., fluorine, chlorine, bromine, iodine),
(2) optionally halogenated lower alkyl (e.g., optionally halogenated $C_{1-6}$ alkyl such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl etc., and the like),
(3) cycloalkyl (e.g., $C_{3-6}$ cycloalkyl such as cyclopropyl, cyclobutyl, cyclopentyl, cyclohexyl, and the like),
(4) lower alkynyl (e.g., $C_{2-6}$ alkynyl such as ethynyl, 1-propynyl, propargyl etc., and the like),
(5) lower alkenyl (e.g., $C_{2-6}$ alkenyl such as vinyl, allyl, isopropenyl, butenyl, isobutenyl etc., and the like),
(6) aralkyl (e.g., $C_{7-12}$ aralkyl such as benzyl, α-methylbenzyl, phenethyl etc., and the like),
(7) aryl (e.g., $C_{6-10}$ aryl such as phenyl, naphthyl etc., and the like, preferably phenyl),
(8) lower alkoxy (e.g., $C_{1-6}$ alkoxy such as methoxy, ethoxy, propoxy, isopropoxy, butoxy, isobutoxy, sec-butoxy, tert-butoxy etc., and the like),
(9) aryloxy (e.g., $C_{6-10}$ aryloxy such as phenoxy etc., and the like),
(10) lower alkanoyl (e.g., formyl; $C_{1-6}$ alkyl-carbonyl such as acetyl, propionyl, butyryl, isobutyryl etc., and the like),
(11) arylcarbonyl (e.g., $C_{6-10}$ aryl-carbonyl such as benzoyl, naphthoyl etc., and the like),
(12) lower alkanoyloxy (e.g., formyloxy; $C_{1-6}$ alkyl-carbonyloxy such as acetyloxy, propionyloxy, butyryloxy, isobutyryloxy etc., and the like),
(13) arylcarbonyloxy (e.g., $C_{6-10}$ aryl-carbonyloxy such as benzoyloxy, naphthoyloxy etc., and the like),
(14) carboxy,
(15) lower alkoxycarbonyl (e.g., $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl etc., and the like),
(16) aralkyloxycarbonyl (e.g., $C_{7-12}$ aralkyloxy-carbonyl such as benzyloxycarbonyl etc., and the like),
(17) carbamoyl,
(18) oxo,
(19) amidino,
(20) imino,
(21) amino,
(22) mono-lower alkylamino (e.g., mono-$C_{1-6}$ alkylamino such as methylamino, ethylamino, propylamino, isopropylamino, butylamino etc., and the like),
(23) di-lower alkylamino (e.g., di-$C_{1-6}$ alkylamino such as dimethylamino, diethylamino, dipropylamino, diisopropylamino, dibutylamino, N-ethyl-N-methylamino etc., and the like),
(24) 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s) (e.g., 3- to 6-membered cyclic amino optionally containing, besides a carbon atom and one nitrogen atom, 1 to 3 hetero atoms selected from a nitrogen atom, an oxygen atom and a sulfur atom, which optionally has 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like),
(25) alkylenedioxy (e.g., $C_{1-3}$ alkylenedioxy such as methylenedioxy, ethylenedioxy etc., and the like),
(26) hydroxy,
(27) nitro,
(28) cyano,
(29) mercapto,
(30) sulfo,
(31) sulfino,
(32) phosphono,
(33) sulfamoyl,

(34) mono-lower alkylsulfamoyl (e.g., mono-$C_{1-6}$ alkylsulfamoyl such as N-methylsulfamoyl, N-ethylsulfamoyl, N-propylsulfamoyl, N-isopropylsulfamoyl, N-butylsulfamoyl etc., and the like),

(35) di-lower alkylsulfamoyl (e.g., di-$C_{1-6}$ alkylsulfamoyl such as N,N-dimethylsulfamoyl, N,N-diethylsulfamoyl, N,N-dipropylsulfamoyl, N,N-dibutylsulfamoyl etc., and the like),

(36) lower alkylthio (e.g., $C_{1-6}$ alkylthio such as methylthio, ethylthio, propylthio, isopropylthio, butylthio, sec-butylthio, tert-butylthio etc., and the like),

(37) arylthio (e.g., $C_{6-10}$ arylthio such as phenylthio, naphthylthio etc., and the like),

(38) lower alkylsulfinyl (e.g., $C_{1-6}$ alkylsulfinyl such as methylsulfinyl, ethylsulfinyl, propylsulfinyl, butylsulfinyl etc., and the like),

(39) arylsulfinyl (e.g., $C_{6-10}$ arylsulfinyl such as phenylsulfinyl, naphthylsulfinyl etc., and the like),

(40) lower alkylsulfonyl (e.g., $C_{1-6}$ alkylsulfonyl such as methylsulfonyl, ethylsulfonyl, propylsulfonyl, butylsulfonyl etc., and the like),

(41) arylsulfonyl (e.g., $C_{6-10}$ arylsulfonyl such as phenylsulfonyl, naphthylsulfonyl etc., and the like) and the like are used.

The "heterocyclic group" of the "heterocyclic group optionally having substituent(s)" may have 1 to 5, preferably 1 to 3, substituents selected from the aforementioned substituents (1)-(41) [hereinafter the group consisting of these (1)-(41) is sometimes to be abbreviated as "substituent group B"], at substitutable position(s) of the heterocyclic group. When the number of the substituents is two or more, each substituent may be the same or different.

The term used in the present specification "amino optionally having substituent(s)" means amino optionally having, as substituent, 1 or 2, the same or different groups selected from, for example, (i) the aforementioned "hydrocarbon group optionally having substituent(s)", (ii) the groups recited as examples of the substituent that the "hydrocarbon group optionally having substituent(s)" may have and the like. Preferable examples of the substituent that the "amino" may have include $C_{1-6}$ alkyl optionally having substituent(s), $C_{6-10}$ aryl optionally having substituent(s) and the like. As the substituent that the "$C_{1-6}$ alkyl" and "$C_{6-10}$ aryl" may have, those similar to the substituents that the aforementioned "hydrocarbon group" may have are used.

The term used in the present specification "hydroxy optionally having a substituent" means (1) hydroxy or (2) hydroxy having, instead of the hydrogen atom of hydroxy, one group selected from, for example, (i) the aforementioned "hydrocarbon group optionally having substituent(s)", (ii) the groups recited as examples of the substituent that the "hydrocarbon group optionally having substituent(s)" may have and the like. As the "hydroxy optionally having a substituent", for example, hydroxy, $C_{1-6}$ alkoxy optionally having substituent(s), $C_{2-6}$ alkenyloxy optionally having substituent(s), $C_{2-6}$ alkynyloxy optionally having substituent(s), $C_{3-6}$ cycloalkyloxy optionally having substituent(s), $C_{6-14}$ aryloxy optionally having substituent(s) and the like can be mentioned. Preferred are hydroxy, $C_{1-6}$ alkoxy optionally having substituent(s), $C_{6-14}$ aryloxy optionally having substituent(s) and the like. As the substituent that the "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, those similar to the substituents that the aforementioned "hydrocarbon group" may have are used.

The term used in the present specification "mercapto(thiol) optionally having a substituent" means (1) mercapto or (2) mercapto having, instead of the hydrogen atom of mercapto, one group selected from, for example, (i) the aforementioned "hydrocarbon group optionally having substituent(s)", (ii) the groups recited as examples of the substituent that the "hydrocarbon group optionally having substituent(s)" may have and the like. As the "mercapto optionally having a substituent", for example, mercapto, $C_{1-6}$ alkylthio optionally having substituent(s), $C_{2-6}$ alkenylthio optionally having substituent(s), $C_{2-6}$ alkynylthio optionally having substituent(s), $C_{3-6}$ cycloalkylthio optionally having substituent(s), $C_{6-14}$ arylthio optionally having substituent(s) and the like can be mentioned. Preferred are mercapto, $C_{1-6}$ alkylthio optionally having substituent(s), $C_{6-14}$ arylthio optionally having substituent(s) and the like. As the substituent that the "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, those similar to the substituents that the aforementioned "hydrocarbon group" may have are used.

As the "lower alkyl" of the term used in the present specification "lower alkyl optionally having substituent(s)", for example, $C_{1-6}$ alkyl such as methyl, ethyl, propyl, isopropyl, butyl, isobutyl, sec-butyl, tert-butyl etc., and the like can be mentioned. The "lower alkyl" may have, as the substituent, for example, 1 to 3 substituents that the aforementioned "hydrocarbon group" may have, and the like.

As the "optionally halogenated $C_{1-6}$ alkyl" used in the present specification, for example, $C_{1-6}$ alkyl optionally having 1 to 5 (preferably 1 to 3) halogen atoms such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl and the like can be mentioned.

As the "optionally halogenated $C_{1-6}$ alkoxy" used in the present specification, for example, $C_{1-6}$ alkoxy optionally having 1 to 5 (preferably 1 to 3) halogen atoms such as methoxy, ethoxy, propoxy, isopropoxy, butoxy, isobutoxy, pentyloxy, hexyloxy, trifluoromethoxy and the like can be mentioned.

As the "optionally halogenated $C_{1-6}$ alkyl-carbonylamino" used in the present specification, for example, $C_{1-6}$ alkyl-carbonylamino optionally having 1 to 5 (preferably 1 to 3) halogen atoms such as acetylamino, trifluoroacetylamino and the like can be mentioned.

As the "$C_{7-13}$ aralkyloxy" used in the present specification, for example, benzyloxy, phenethyloxy and the like can be mentioned.

In the aforementioned formulas, $R^1$ is a hydrocarbon group optionally having substituent(s), amino optionally having substituent(s), hydroxy optionally having a substituent or a heterocyclic group optionally having substituent(s).

Preferable examples of the "hydrocarbon group" of the "hydrocarbon group optionally having substituent(s)" for $R^1$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include alkyl (e.g., $C_{1-6}$ alkyl such as methyl, ethyl etc., and the like), alkenyl (e.g., $C_{2-6}$ alkenyl such as vinyl etc., and the like), cycloalkyl (e.g., $C_{3-6}$ cycloalkyl such as cyclopropyl etc., and the like), phenyl and the like. The "alkyl", "alkenyl", "alkynyl", "cycloalkyl" and "aryl" may have, for example, 1 to 5, preferably 1 to 3, substituents (preferably, halogen atom such as chlorine, fluorine etc.; $C_{1-6}$ alkoxy such as methoxy, ethoxy etc.; hydroxy; $C_{1-6}$ alkyl-carbonyloxy such as acetyloxy etc., and the like) that the aforementioned "hydrocarbon group" may have, and the like.

As the substituent of the "amino optionally having substituent(s)" for $R^1$, preferably, for example, 1 or 2 substituents selected from lower alkyl optionally having substituent(s), aryl optionally having substituent(s) and the like are used, and particularly, one lower alkyl optionally having substituent(s) is used. As the "lower alkyl", for example, $C_{1-6}$ alkyl such as methyl, ethyl, propyl, isopropyl, butyl, isobutyl, sec-butyl, tert-butyl etc., and the like are used. The "lower alkyl" may have, for example, 1 to 3 substituents that the aforementioned "hydrocarbon group" may have, and the like. As the "aryl", for example, $C_{6-10}$ aryl such as phenyl etc., and the like are used. The "aryl" may have, for example, 1 to 5, preferably 1 to 3, substituents (preferably, halogen atom such as fluorine, chlorine etc.; $C_{1-6}$ alkoxy such as methoxy, ethoxy etc., and the like) that the aforementioned "hydrocarbon group" may have, and the like. As the "amino optionally having substituent(s)", for example, $C_{6-10}$ arylamino (e.g., phenylamino and the like) optionally having 1 to 3 $C_{1-6}$ alkoxy (e.g., methoxy and the like), or mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like) and the like are widely used.

Preferable examples of the "hydroxy optionally having a substituent" for $R^1$ include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like. More preferable examples include $C_{1-6}$ alkoxy (e.g., methoxy and the like) optionally having substituent(s), $C_{2-6}$ alkenyloxy (e.g., vinyloxy and the like) optionally having substituent(s), $C_{3-6}$ cycloalkyloxy (e.g., cyclopropyloxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "heterocyclic group" of the "heterocyclic group optionally having substituent(s)" for $R^1$ include a 5- or 6-membered heterocyclic group containing, besides a carbon atom, 1 to 3 hetero atoms selected from a nitrogen atom, an oxygen atom and a sulfur atom, and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, a 6-membered nitrogen-containing heterocyclic group (e.g., pyridyl and the like) and the like can be used. Preferable examples of the substituent of the "heterocyclic group optionally having substituent(s)" for $R^1$ include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), $C_{7-12}$ aralkyloxy-carbonyl (e.g., benzyloxycarbonyl and the like) and the like.

$R^1$ is preferably for example, (i) $C_{1-6}$ alkyl optionally having substituent(s), (ii) $C_{3-6}$ cycloalkyl optionally having substituent(s), (iii) $C_{2-6}$ alkenyl optionally having substituent(s) or the like. Particularly, $C_{1-6}$ alkyl (e.g., methyl, ethyl) optionally having substituent(s) is more preferable. These groups optionally have, as the substituent, for example, 1 to 5 substituents that the aforementioned "hydrocarbon group" may have and the like.

$R^1$ is preferably (i) $C_{1-6}$ alkyl optionally having substituent (s), (ii) $C_{3-6}$ cycloalkyl, (iii) $C_{6-14}$ aryl, (iv) amino optionally having substituent(s) or the like. More preferably, $R^1$ is (i) $C_{1-6}$ alkyl optionally having 1 to 3 substituents selected from $C_{1-6}$ alkyl-carbonyloxy, hydroxy, a halogen atom and the like, (ii) $C_{3-6}$ cycloalkyl, (iii) phenyl, (iv) mono- or di-$C_{1-6}$ alkylamino or the like.

In the aforementioned formulas, $R^5$ is a hydrogen atom, a halogen atom, a hydrocarbon group optionally having substituent(s), amino optionally having substituent(s), hydroxy optionally having a substituent or mercapto optionally having a substituent.

The "halogen atom" for $R^5$ is preferably fluorine, chlorine or bromine.

Preferable examples of the "hydrocarbon group" of the "hydrocarbon group optionally having substituent(s)" for $R^5$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. Particularly preferably, alkyl (e.g., $C_{1-6}$ alkyl such as methyl etc., and the like), alkenyl (e.g., $C_{2-6}$ alkenyl such as vinyl etc., and the like) and the like can be mentioned. The "alkyl", "alkenyl", "alkynyl", "cycloalkyl" and "aryl" may have, for example, 1 to 5, preferably 1 to 3, substituents that the aforementioned "hydrocarbon group" may have, and the like.

Preferable examples of the substituent of the "amino optionally having substituent(s)" for $R^5$ include 1 or 2 substituents selected from lower alkyl optionally having substituent(s), aryl optionally having substituent(s) and the like. More preferably, for example, one lower alkyl optionally having substituent(s) is used. As the "lower alkyl", for example, $C_{1-6}$ alkyl such as methyl, ethyl, propyl, isopropyl, butyl, isobutyl, sec-butyl, tert-butyl etc., and the like are used. The "lower alkyl" may have, for example, 1 to 3 substituents that the aforementioned "hydrocarbon group" may have, and the like. As the "aryl", for example, $C_{6-10}$ aryl such as phenyl etc., and the like are used. The "aryl" may have, for example, 1 to 5, preferably 1 to 3, substituents (preferably, halogen atom such as fluorine, chlorine etc.; $C_{1-6}$ alkoxy such as methoxy, ethoxy etc., and the like) that the aforementioned "hydrocarbon group" may have, and the like. As the "amino optionally having substituent(s)", for example, $C_{6-10}$ arylamino (e.g., phenylamino and the like) optionally having 1 to 3 $C_{1-6}$ alkoxy (e.g., methoxy and the like), mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like) and the like are widely used.

Preferable examples of the "hydroxy optionally having a substituent" for $R^5$ include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like. More preferable examples include hydroxy, $C_{1-6}$ alkoxy (e.g., methoxy and the like) optionally having substituent(s), $C_{6-14}$ aryloxy (e.g., phenoxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "mercapto optionally having a substituent" for $R^5$ include mercapto, $C_{1-6}$ alkylthio (e.g., methylthio, ethylthio, propylthio, isopropylthio and the like) optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio (e.g., phenylthio and the like) optionally having substituent(s) and the like. More preferable examples include mercapto, $C_{1-6}$ alkylthio (e.g., methylthio and the like) optionally having substituent(s), $C_{6-14}$ arylthio (e.g., phenylthio and the like) optionally having substituent(s) and the like. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

$R^5$ is preferably a hydrogen atom, $C_{1-6}$ alkyl optionally having substituent(s) or the like. More preferably, it is a hydrogen atom, $C_{1-6}$ alkyl or the like, particularly preferably a hydrogen atom.

In the aforementioned formulas, $R^6$ is a hydrogen atom or a hydrocarbon group optionally having substituent(s).

Preferable examples of the "hydrocarbon group" of the "hydrocarbon group optionally having substituent(s)" for $R^6$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferred are alkyl (e.g., $C_{1-6}$ alkyl such as methyl etc., and the like), aryl (e.g., $C_{6-14}$ aryl such as phenyl etc., and the like) and the like. The "alkyl", "alkenyl", "alkynyl", "cycloalkyl" and "aryl" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

$R^6$ is preferably a hydrogen atom, $C_{1-6}$ alkyl optionally having substituent(s) or the like. More preferably, it is a hydrogen atom, $C_{1-6}$ alkyl or the like. Particularly preferably, it is a hydrogen atom.

In the aforementioned formulas, ring A is a 5-membered ring optionally having substituent(s).

As the substituent of the "5-membered ring optionally having substituent(s)", for example, a halogen atom, a hydrocarbon group optionally having substituent(s), amino optionally having substituent(s), hydroxy optionally having a substituent, mercapto optionally having a substituent, a heterocyclic group optionally having substituent(s) and the like can be mentioned. Ring A may have 1 or 2 of the above-mentioned substituents at substitutable position(s).

Preferable examples of the "halogen atom" include fluorine, chlorine and bromine.

Preferable examples of the "hydrocarbon group" of the "hydrocarbon group optionally having substituent(s)" include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include alkyl (e.g., $C_{1-6}$ alkyl such as methyl etc., and the like), alkenyl (e.g., $C_{2-6}$ alkenyl such as vinyl etc., and the like) and the like. The "alkyl", "alkenyl", "alkynyl", "cycloalkyl" and "aryl" may have, for example, 1 to 5, preferably 1 to 3, substituents that the aforementioned "hydrocarbon group" may have, and the like.

Preferable examples of the "amino optionally having substituent(s)" include amino, $C_{1-6}$ alkylamino optionally having substituent(s), $C_{6-10}$ arylamino optionally having substituent(s) and the like. More preferable examples include amino, mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like), $C_{6-10}$ arylamino (e.g., phenylamino and the like) and the like.

Preferable examples of the "hydroxy optionally having a substituent" include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like. More preferable examples include hydroxy, $C_{1-6}$ alkoxy (e.g., methoxy and the like) optionally having substituent(s), $C_{6-14}$ aryloxy (e.g., phenoxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "mercapto optionally having a substituent" include mercapto, $C_{1-6}$ alkylthio (e.g., methylthio, ethylthio, propylthio, isopropylthio and the like) optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio (e.g., phenylthio and the like) optionally having substituent(s) and the like. More preferable examples include mercapto, $C_{1-6}$ alkylthio (e.g., methylthio and the like) optionally having substituent(s), $C_{6-14}$ arylthio (e.g., phenylthio and the like) optionally having substituent(s) and the like. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "heterocyclic group" of the "heterocyclic group optionally having substituent(s)" include a 5- or 6-membered heterocyclic group containing, besides a carbon atom, 1 to 3 hetero atoms selected from a nitrogen atom, an oxygen atom and a sulfur atom and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. More preferable examples include a 6-membered nitrogen-containing heterocyclic group (e.g., pyridyl and the like) and the like. Preferable examples of the substituent of the "heterocyclic group optionally having substituent(s)" include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), $C_{7-12}$ aralkyloxy-carbonyl (e.g., benzyloxycarbonyl and the like), amino, mono-$C_{1-6}$ alkylamino (e.g., methylamino, ethylamino and the like), di-$C_{1-6}$ alkylamino (e.g., dimethylamino, diethylamino and the like) and the like.

Ring A is preferably a 5-membered ring optionally having 1 or 2 substituents selected from a halogen atom, a hydrocarbon group optionally having substituent(s), amino optionally having substituent(s), hydroxy optionally having a substituent and mercapto optionally having a substituent. Preferable examples of ring A include a 5-membered ring optionally having 1 or 2 substituents selected from $C_{1-6}$ alkyl optionally having substituent(s) (e.g., 1 to 5 substituents selected from substituent group A), $C_{2-6}$ alkenyl optionally having substituent(s) (e.g., 1 to 5 substituents selected from substituent group A) and $C_{3-6}$ cycloalkyl optionally having substituent(s) (e.g., 1 to 5 substituents selected from substituent group A), and the like. More preferable examples include a 5-membered ring optionally having 1 or 2 $C_{1-6}$ alkyl optionally having substituent(s) (e.g., 1 to 5 substituents selected from substituent group A) and the like. Particularly, a 5-membered ring optionally having one $C_{1-6}$ alkyl optionally having substituent(s) (e.g., 1 to 5 substituents selected from substituent group A) is preferable. Preferable examples of the "substituent" include a halogen atom, optionally halogenated $C_{1-6}$ alkyl, optionally halogenated $C_{1-6}$ alkoxy, $C_{7-12}$ aralkyl, phenyl and the like.

In the aforementioned formulas, ring B is a 6-membered ring optionally having substituent(s).

As the substituent of the "6-membered ring optionally having substituent(s)", a halogen atom, a hydrocarbon group optionally having substituent(s), amino optionally having substituent(s), hydroxy optionally having a substituent, mercapto optionally having a substituent, a heterocyclic group optionally having substituent(s) and the like can be mentioned. Ring B optionally has 1 or 2 substituents mentioned above at substitutable position(s). Preferable examples of these substituents include preferable examples of the substituent of ring A and the like.

Preferable examples of ring B include a 6-membered ring optionally having 1 or 2 substituents selected from a halogen atom, a hydrocarbon group optionally having substituent(s), amino optionally having substituent(s), hydroxy optionally having a substituent and mercapto optionally having a substituent, and the like. Ring B is more preferably a 6-membered ring optionally having 1 or 2 substituents selected from a halogen atom, hydroxy optionally having a substituent and $C_{1-6}$ alkyl optionally having substituent(s). Of these, a 6-membered ring optionally having 1 or 2 halogen atoms is preferable. Unsubstituted 6-membered ring is more preferable.

In the aforementioned formulas, ring C is a 5-membered ring optionally having substituent(s).

As the substituent of the "5-membered ring optionally having substituent(s)", for example, a halogen atom, a hydrocarbon group optionally having substituent(s), hydroxy optionally having a substituent, a heterocyclic group optionally having substituent(s) and the like can be mentioned. Ring C optionally has 1 or 2 substituents mentioned above at substitutable position(s).

Preferable examples of the "halogen atom" include fluorine, chlorine and bromine.

Preferable examples of the "hydrocarbon group" of the "hydrocarbon group optionally having substituent(s)" include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include for example, alkyl (e.g., $C_{1-6}$ alkyl such as methyl etc., and the like), aryl (e.g., $C_{6-14}$ aryl phenyl etc., and the like) and the like. The "alkyl", "alkenyl", "alkynyl", "cycloalkyl" and "aryl" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "hydrocarbon group" of the "hydrocarbon group optionally having substituent(s)" include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include for example, alkyl (e.g., $C_{1-6}$ alkyl such as methyl etc., and the like), aryl (e.g., $C_{6-14}$ aryl such as phenyl etc., and the like) and the like. The "alkyl", "alkenyl", "alkynyl", "cycloalkyl" and "aryl" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

As a preferable example of the "heterocyclic group" of the "heterocyclic group optionally having substituent(s)", for example, a 5- or 6-membered heterocyclic group containing, besides a carbon atom, 1 to 3 hetero atoms selected from a nitrogen atom, an oxygen atom and a sulfur atom and the like can be mentioned. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, a 6-membered nitrogen-containing heterocyclic group (e.g., pyridyl and the like) and the like can be mentioned. Preferable examples of the substituent of the "heterocyclic group optionally having substituent(s)" include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), $C_{7-12}$ aralkyloxy-carbonyl (e.g., benzyloxycarbonyl and the like), amino, mono-$C_{1-6}$ alkylamino (e.g., methylamino, ethylamino and the like), di-$C_{1-6}$ alkylamino (e.g., dimethylamino, diethylamino and the like) and the like.

Preferable examples of ring C include a 5-membered ring optionally having 1 or 2 substituents selected from a halogen atom, a hydrocarbon group optionally having substituent(s), hydroxy optionally having a substituent and a heterocyclic group optionally having substituent(s), and the like. More preferable examples of ring C include a 5-membered ring optionally having 1 or 2 substituents selected from $C_{1-6}$ alkyl optionally having substituent(s) (e.g., 1 to 5 substituents selected from substituent group A), $C_{3-6}$ cycloalkyl optionally having substituent(s) (e.g., 1 to 5 substituents selected from substituent group A), $C_{6-10}$ aryl optionally having substituent(s) (e.g., 1 to 5 substituents selected from substituent group A) and a 5- or 6-membered heterocyclic group optionally having substituent(s) (e.g., 1 to 5 substituents selected from substituent group B). As the substituent, 1 or 2 substituents selected from a halogen atom, optionally halogenated $C_{1-6}$ alkyl, optionally halogenated $C_{3-6}$ cycloalkyl, optionally halogenated $C_{6-10}$ aryl, optionally halogenated $C_{7-12}$ aralkyl, optionally halogenated $C_{1-6}$ alkoxy, amino, mono-$C_{1-6}$ alkylamino, di-$C_{1-6}$ alkylamino, optionally halogenated 5- or 6-membered aromatic heterocyclic group and the like can be mentioned. Ring C is more preferably a 5-membered ring optionally having one substituent selected from optionally halogenated $C_{1-6}$ alkyl, optionally halogenated $C_{3-6}$ cycloalkyl, optionally halogenated phenyl, optionally halogenated $C_{7-12}$ aralkyl and optionally halogenated 5- or 6-membered aromatic heterocyclic group.

As the tricycle consisting of ring A, ring B and ring C, for example, a ring represented by the formula

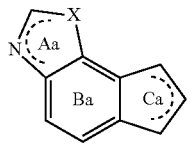

wherein ring Aa is as defined for ring A, ring Ba is as defined for ring B, ring Ca is as defined for ring C, and X is as defined above, and the like can be mentioned. Preferable examples of the tricycle include a ring represented by the formula

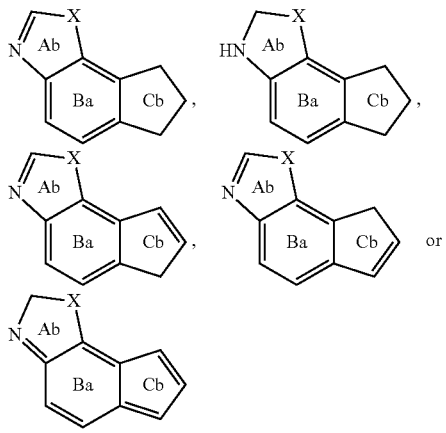

wherein ring Ab is as defined for ring A, ring Cb is as defined for ring C, and other symbols are as defined above, and the like.

In the aforementioned formulas, $R^2$ is a hydrogen atom, a halogen atom, a hydrocarbon group optionally having substituent(s) or a heterocyclic group optionally having substituent(s).

The "halogen atom" for $R^2$ is preferably fluorine, chlorine or bromine.

Preferable examples of the "hydrocarbon group" of the "hydrocarbon group optionally having substituent(s)" for $R^2$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include alkyl (e.g., $C_{1-6}$ alkyl such as methyl etc., and the like), aryl (e.g., $C_{6-14}$ aryl such as phenyl etc., and the like) and the like. The "alkyl", "alkenyl", "alkynyl", "cycloalkyl" and "aryl" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "heterocyclic group" of the "heterocyclic group optionally having substituent(s)" for $R^2$ include a 5- or 6-membered heterocyclic group containing, besides a carbon atom, 1 to 3 hetero atoms selected from a nitrogen atom, an oxygen atom and a sulfur atom and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, a 6-membered nitrogen-containing heterocyclic group (e.g., pyridyl and the like) and the like can be mentioned. Preferable examples of the substituent of the "heterocyclic group optionally having substituent(s)" for $R^2$ include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), $C_{7-12}$ aralkyloxy-carbonyl (e.g., benzyloxycarbonyl and the like), amino, mono-$C_{1-6}$ alkylamino (e.g., methylamino, ethylamino and the like), di-$C_{1-6}$ alkylamino (e.g., dimethylamino, diethylamino and the like) and the like.

$R^2$ is preferably for example, a hydrogen atom, a hydrocarbon group optionally having substituent(s), a heterocyclic group optionally having substituent(s) or the like. More preferable examples include (i) a hydrogen atom, (ii) $C_{1-6}$ alkyl optionally having substituent(s), (iii) $C_{6-10}$ aryl optionally having substituent(s), (iv) a 5- or 6-membered heterocyclic group optionally having substituent(s) and the like. More preferably, for example, (i) a hydrogen atom, (ii) $C_{1-6}$ alkyl, (iii) $C_{6-10}$ aryl optionally having 1 or 2 substituents selected from a halogen atom, $C_{1-6}$ alkyl, $C_{1-6}$ alkoxy, amino and mono- or di-$C_{1-6}$ alkylamino, (iv) a 6-membered nitrogen-containing heterocyclic group optionally having 1 or 2 substituents selected from a halogen atom, $C_{1-6}$ alkyl, $C_{1-6}$ alkoxy, amino and mono- or di-$C_{1-6}$ alkylamino and the like can be mentioned. More preferable $R^2$ includes a hydrogen atom, $C_{1-6}$ alkyl, phenyl and the like. More preferable $R^2$ includes a hydrogen atom, $C_{1-6}$ alkyl and the like. Particularly preferable $R^2$ is a hydrogen atom.

In the aforementioned formulas, $R^3$ is a hydrogen atom, a hydrocarbon group optionally having substituent(s), amino optionally having substituent(s), hydroxy optionally having a substituent, mercapto optionally having a substituent or a heterocyclic group optionally having substituent(s).

Preferable examples of the "hydrocarbon group" of the "hydrocarbon group optionally having substituent(s)" for $R^3$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include alkyl (e.g., $C_{1-6}$ alkyl such as methyl etc., and the like), alkenyl (e.g., $C_{2-6}$ alkenyl such as vinyl etc., and the like) and the like. The "alkyl", "alkenyl", "alkynyl", "cycloalkyl" and "aryl" may have, for example, 1 to 5, preferably 1 to 3, substituents that the aforementioned "hydrocarbon group" may have, and the like.

Preferable examples of the substituent of the "amino optionally having substituent(s)" for $R^3$ include 1 or 2 substituents selected from lower alkyl optionally having substituent(s), aryl optionally having substituent(s) and the like. More preferably, one lower alkyl optionally having substituent(s) is used. As the "lower alkyl", for example, $C_{1-6}$ alkyl such as methyl, ethyl, propyl, isopropyl, butyl, isobutyl, sec-butyl, tert-butyl etc., and the like are used. The "lower alkyl" may have, for example, 1 to 3 substituents that the aforementioned "hydrocarbon group" may have, and the like. As the "aryl", for example, $C_{6-10}$ aryl such as phenyl etc., and the like are used. The "aryl" may have, for example, 1 to 5, preferably 1 to 3, substituents (preferably, halogen atom such as fluorine, chlorine etc.; $C_{1-6}$ alkoxy such as methoxy, ethoxy etc., and the like) that the aforementioned "hydrocarbon group" may have, and the like. As the "amino optionally having substituent(s)", for example, $C_{6-10}$ arylamino (e.g., phenylamino and the like) optionally having 1 to 3 $C_{1-6}$ alkoxy (e.g., methoxy and the like), or mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like) and the like are widely used.

Preferable examples of the "hydroxy optionally having a substituent" for $R^3$ include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like. More preferable examples include hydroxy, $C_{1-6}$ alkoxy (e.g., methoxy and the like) optionally having substituent(s), $C_{6-14}$ aryloxy (e.g., phenoxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "mercapto optionally having a substituent" for $R^3$ include mercapto, $C_{1-6}$ alkylthio (e.g., methylthio, ethylthio, propylthio, isopropylthio and the like) optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio (e.g., phenylthio and the like) optionally having substituent(s) and the like. More preferable examples include mercapto, $C_{1-6}$ alkylthio (e.g., methylthio and the like) optionally having substituent(s), $C_{6-14}$ arylthio (e.g., phenylthio and the like) optionally having substituent(s) and the like. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "heterocyclic group" of the "heterocyclic group optionally having substituent(s)" for $R^3$ include a 5- or 6-membered heterocyclic group containing, besides a carbon atom, 1 to 3 hetero atoms selected from a nitrogen atom, an oxygen atom and a sulfur atom, and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like are used. Particularly preferably, a 6-membered nitrogen-containing heterocyclic group (e.g., pyridyl and the like) and the like are used. Preferable examples of the substituent of the "heterocyclic group optionally having substituent(s)" for $R^3$ include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), $C_{7-12}$ aralkyloxy-carbonyl (e.g., benzyloxycarbonyl and the like), amino, mono-$C_{1-6}$ alkylamino (e.g., methylamino, ethylamino and the like), di-$C_{1-6}$ alkylamino (e.g., dimethylamino, diethylamino and the like) and the like.

$R^3$ is preferably a hydrogen atom, $C_{1-6}$ alkyl optionally having substituent(s), $C_{2-6}$ alkenyl optionally having substituent(s), amino optionally having substituent(s) or the like. More preferable examples include a hydrogen atom, $C_{1-6}$ alkyl optionally having substituent(s) and the like.

As more preferable examples for $R^3$, (i) a hydrogen atom, (ii) $C_{1-6}$ alkyl optionally having 1 to 5 substituents selected from halogen atom and $C_{1-6}$ alkoxy, (iii) $C_{6-10}$ aryl-$C_{1-6}$ alkyl optionally having 1 to 5 substituents selected from halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and optionally halogenated $C_{1-6}$ alkyl-carbonylamino, and the like can be mentioned.

$R^3$ is preferably, for example, (i) a hydrogen atom, (ii) $C_{1-6}$ alkyl optionally having substituent(s), (iii) $C_{3-6}$ cycloalkyl, (iv) $C_{6-14}$ aryl, (v) hydroxy optionally having a substituent, (vi) mercapto optionally having a substituent, (vii) amino optionally having substituent(s) or the like. More preferable examples include (i) a hydrogen atom, (ii) $C_{1-6}$ alkyl optionally having 1 to 3 substituents selected from phenyl, hydroxy, a halogen atom, $C_{1-6}$ alkyl-carbonyl, $C_{7-13}$ aralkyloxy, pyridyl and the like, (iii) $C_{3-6}$ cycloalkyl, (iv) phenyl, (v) $C_{1-6}$ alkoxy, (vi) mercapto, (vii) $C_{1-6}$ alkylthio, (viii) mono- or di-$C_{1-6}$ alkylamino and the like.

In the aforementioned formulas, $R^{4a}$ and $R^{4b}$ are the same or different and each is a hydrogen atom, a halogen atom, a hydrocarbon group optionally having substituent(s), amino optionally having substituent(s), hydroxy optionally having a substituent, mercapto optionally having a substituent or a heterocyclic group optionally having substituent(s).

The "halogen atom" for $R^{4a}$ or $R^{4b}$ is preferably fluorine, chlorine or bromine.

Preferable examples of the "hydrocarbon group optionally having substituent(s)" for $R^{4a}$ or $R^{4b}$ include those similar to the "hydrocarbon group optionally having substituent(s)" for $R^3$.

Preferable examples of the "amino optionally having substituent(s)" for $R^{4a}$ or $R^{4b}$ include those similar to the "amino optionally having substituent(s)" for $R^3$.

Preferable examples of the "hydroxy optionally having a substituent" for $R^{4a}$ or $R^{4b}$ include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like. More preferable examples include hydroxy, $C_{1-6}$ alkoxy (e.g., methoxy and the like) optionally having substituent(s), $C_{6-14}$ aryloxy (e.g., phenoxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "mercapto optionally having a substituent" for $R^{4a}$ or $R^{4b}$ include mercapto, $C_{1-6}$ alkylthio (e.g., methylthio, ethylthio, propylthio, isopropylthio and the like) optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio (e.g., phenylthio and the like) optionally having substituent(s) and the like. More preferable examples include mercapto, $C_{1-6}$ alkylthio (e.g., methylthio and the like) optionally having substituent(s), $C_{6-14}$ arylthio (e.g., phenylthio and the like) optionally having substituent(s) and the like. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, for example, 1 to 5, preferably 1 to 3, substituents (preferably, halogen atom such as chlorine, fluorine etc.; $C_{1-6}$ alkoxy such as methoxy, ethoxy etc., and the like) that the aforementioned "hydrocarbon group" may have, and the like.

Preferable examples of the "heterocyclic group optionally having substituent(s)" for $R^{4a}$ or $R^{4b}$ include those similar to the "heterocyclic group optionally having substituent(s)" recited as examples of the substituents that the "6-membered ring optionally having substituent(s)" for ring B may have.

Preferable examples of $R^{4a}$ include a hydrogen atom, a halogen atom, hydroxy optionally having a substituent, $C_{1-6}$ alkyl optionally having substituent(s) and the like. More preferably, $R^{4a}$ is a hydrogen atom or a halogen atom, and particularly preferably a hydrogen atom.

Preferable examples of $R^{4b}$ include a hydrogen atom, a halogen atom, hydroxy optionally having a substituent, $C_{1-6}$ alkyl optionally having substituent(s) and the like. More preferably, $R^{4b}$ is a hydrogen atom or a halogen atom, and particularly preferably a hydrogen atom.

In the aforementioned formulas, X is an oxygen atom or a sulfur atom.

As the formula (I), for example, the following formula

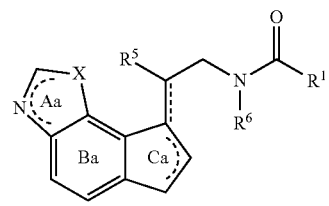

wherein each symbol is as defined above, can be mentioned.

Preferable examples of compound (I) include a compound represented by the formula

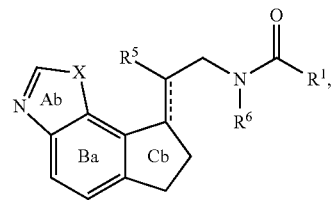,

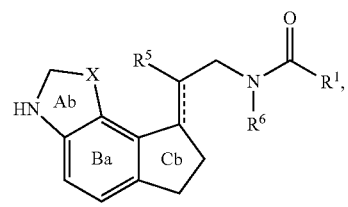,

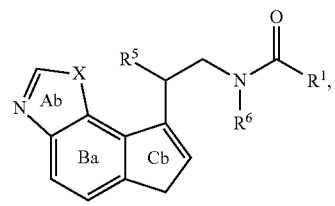,

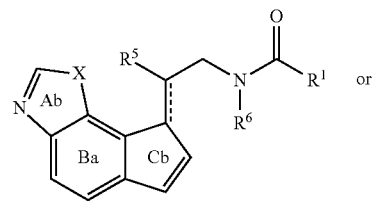 or

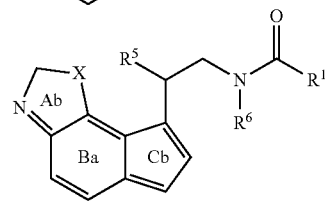

wherein each symbol is as defined above, and the like.

More preferable examples of the compound (I) include a compound represented by the formula

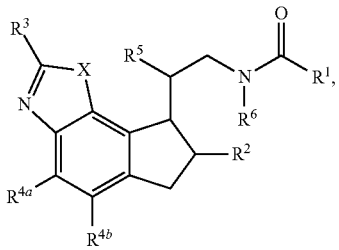

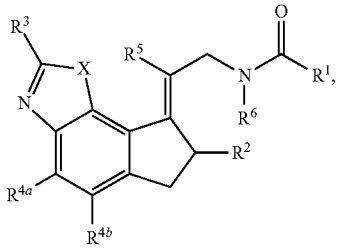

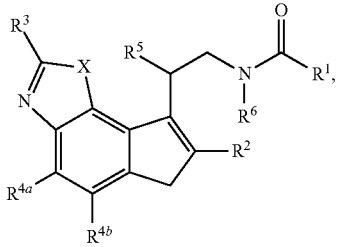

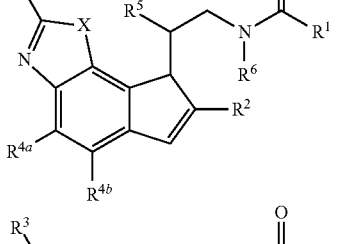 or

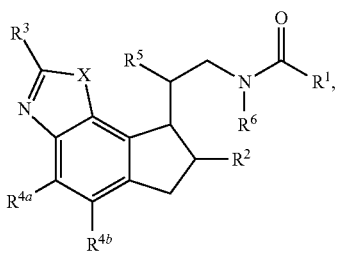

wherein each symbol is as defined above, and the like.

More preferable examples of the compound (I) include a compound represented by the formula

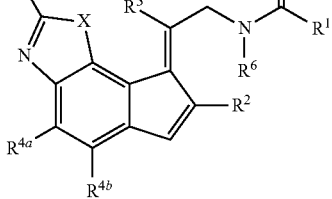

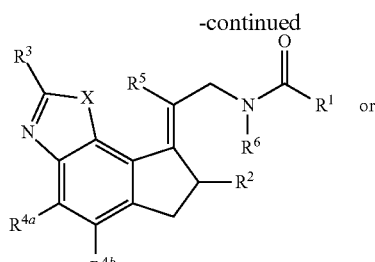 or

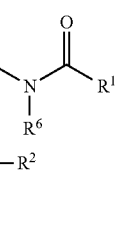

wherein each symbol is as defined above, and the like.

Particularly preferable examples of the compound (I) include a compound represented by the formula

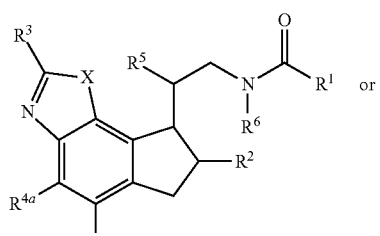 or

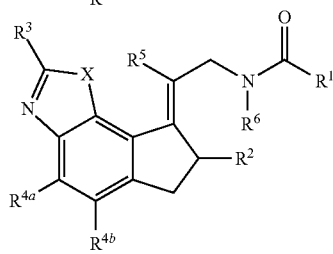

wherein each symbol is as defined above, and the like.

Preferable examples of compound (I) include the following compounds and the like.

[Compound A]

A compound of the formula (I'), wherein $R^1$ is $C_{1-6}$ alkyl optionally having substituent(s), $C_{3-6}$ cycloalkyl optionally having substituent(s) or $C_{2-6}$ alkenyl optionally having substituent(s);

$R^2$ is a hydrogen atom, a hydrocarbon group optionally having substituent(s) or a heterocyclic group optionally having substituent(s);

$R^3$ is a hydrogen atom, $C_{1-6}$ alkyl optionally having substituent(s), $C_{2-6}$ alkenyl optionally having substituent(s) or amino optionally having substituent(s);

$R^{4a}$ and $R^{4b}$ are the same or different and each is a hydrogen atom, a halogen atom, hydroxy optionally having a substituent or $C_{1-6}$ alkyl optionally having substituent(s);

$R^5$ is a hydrogen atom or $C_{1-6}$ alkyl optionally having substituent(s); and $R^6$ is a hydrogen atom or $C_{1-6}$ alkyl optionally having substituent(s), or a salt thereof.

[Compound B]

A compound of the formula (I'), wherein $R^1$ is (i) (a) $C_{1-6}$ alkyl, (b) $C_{2-6}$ alkenyl, (c) $C_{2-6}$ alkynyl, (d) $C_{3-6}$ cycloalkyl or (e) $C_{6-14}$ aryl, each of which optionally has 1 to 5 substituents selected from substituent group A, (ii) amino optionally having 1 or 2 substituents selected from (a) $C_{1-6}$ alkyl, (b) $C_{2-6}$ alkenyl, (c) $C_{2-6}$ alkynyl, (d) $C_{3-6}$ cycloalkyl and (e) $C_{6-14}$ aryl, each of which optionally has 1 to 5 substituents selected from substituent group A, or (iii) a 5- to 14-membered heterocyclic group containing, besides a carbon atom, 1 to 3 hetero atoms selected from an oxygen atom, a sulfur atom and a nitrogen atom, which optionally has 1 to 5 substituents selected from substituent group B;

$R^2$ is (i) a hydrogen atom, (ii) a halogen atom, (iii) (a) $C_{1-6}$ alkyl, (b) $C_{2-6}$ alkenyl, (c) $C_{2-6}$ alkynyl, (d) $C_{3-6}$ cycloalkyl or (e) $C_{6-14}$ aryl, each of which optionally has 1 to 5 substituents selected from substituent group A, or (iv) a 5- to 14-membered heterocyclic group containing, besides a carbon atom, 1 to 3 hetero atoms selected from an oxygen atom, a sulfur atom and a nitrogen atom, which optionally has 1 to 5 substituents selected from substituent group B;

$R^3$ is, (i) a hydrogen atom, (ii) (a) $C_{1-6}$ alkyl, (b) $C_{2-6}$ alkenyl, (c) $C_{2-6}$ alkynyl, (d) $C_{3-6}$ cycloalkyl or (e) $C_{6-14}$ aryl, each of which optionally has 1 to 5 substituents selected from substituent group A, (iii) amino optionally having 1 or 2 substituents selected from (a) $C_{1-6}$ alkyl, (b) $C_{2-6}$ alkenyl, (c) $C_{2-6}$ alkynyl, (d) $C_{3-6}$ cycloalkyl and (e) $C_{6-14}$ aryl, each of which optionally has 1 to 5 substituents selected from substituent group A, (iv) (1) hydroxy, or (2) (a) $C_{1-6}$ alkoxy, (b) $C_{2-6}$ alkenyloxy, (c) $C_{2-6}$ alkynyloxy, (d) $C_{3-6}$ cycloalkyloxy or (e) $C_{6-14}$ aryloxy, each of which optionally has 1 to 5 substituents selected from substituent group A, (v) (1) mercapto, or (2) (a) $C_{1-6}$ alkylthio, (b) $C_{2-6}$ alkenylthio, (d) $C_{2-6}$ alkynylthio, (d) $C_{3-6}$ cycloalkylthio or (e) $C_{6-14}$ arylthio, each of which optionally has 1 to 5 substituents selected from substituent group A, or (vi) a 5- to 14-membered heterocyclic group containing, besides a carbon atom, 1 to 3 hetero atoms selected from an oxygen atom, a sulfur atom and a nitrogen atom, which optionally has 1 to 5 substituents selected from substituent group B;

$R^{4a}$ and $R^{4b}$ are the same or different and each is (i) a hydrogen atom, (ii) a halogen atom, (iii) (a) $C_{1-6}$ alkyl, (b) $C_{2-6}$ alkenyl, (c) $C_{2-6}$ alkynyl, (d) $C_{3-6}$ cycloalkyl or (e) $C_{6-14}$ aryl, each of which optionally has 1 to 5 substituents selected from substituent group A, (iv) amino optionally having 1 or 2 substituents selected from (a) $C_{1-6}$ alkyl, (b) $C_{2-6}$ alkenyl, (c) $C_{2-6}$ alkynyl, (d) $C_{3-6}$ cycloalkyl and (e) $C_{6-14}$ aryl, each of which optionally has 1 to 5 substituents selected from substituent group A, (v) (1) hydroxy, or (2) (a) $C_{1-6}$ alkoxy, (b) $C_{2-6}$ alkenyloxy, (c) $C_{2-6}$ alkynyloxy, (d) $C_{3-6}$ cycloalkyloxy or (e) $C_{6-14}$ aryloxy, each of which optionally has 1 to 5 substituents selected from substituent group A, or (vi) (1) mercapto, or (2) (a) $C_{1-6}$ alkylthio, (b) $C_{2-6}$ alkenylthio, (d) $C_{2-6}$ alkynylthio, (d) $C_{3-6}$ cycloalkylthio or (e) $C_{6-14}$ arylthio, each of which optionally has 1 to 5 substituents selected from substituent group A;

$R^5$ is (i) a hydrogen atom, (ii) a halogen atom, (iii) (a) $C_{1-6}$ alkyl, (b) $C_{2-6}$ alkenyl, (c) $C_{2-6}$ alkynyl, (d) $C_{3-6}$ cycloalkyl or (e) $C_{6-14}$ aryl, each of which optionally has 1 to 5 substituents selected from substituent group A, (iv) amino optionally having 1 or 2 substituents selected from (a) $C_{1-6}$ alkyl, (b) $C_{2-6}$ alkenyl, (c) $C_{2-6}$ alkynyl, (d) $C_{3-6}$ cycloalkyl and (e) $C_{6-14}$ aryl, each of which optionally has 1 to 5 substituents selected from substituent group A, (v) (1) hydroxy, or (2) (a) $C_{1-6}$ alkoxy, (b) $C_{2-6}$ alkenyloxy, (c) $C_{2-6}$ alkynyloxy, (d) $C_{3-6}$ cycloalkyloxy or (e) $C_{6-14}$ aryloxy, each of which optionally has 1 to 5 substituents selected from substituent group A, or (vi) (1) mercapto, or (2) (a) $C_{1-6}$ alkylthio, (b) $C_{2-6}$ alkenylthio, (d) $C_{2-6}$ alkynylthio, (d) $C_{3-6}$ cycloalkylthio or (e) $C_{6-14}$ arylthio, each of which optionally has 1 to 5 substituents selected from substituent group A;

$R^6$ is, (i) a hydrogen atom or (ii) (a) $C_{1-6}$ alkyl, (b) $C_{2-6}$ alkenyl, (c) $C_{2-6}$ alkynyl, (d) $C_{3-6}$ cycloalkyl or (e) $C_{6-14}$ aryl, each of which optionally has 1 to 5 substituents selected from substituent group A; and X is an oxygen atom or a sulfur atom, or a salt thereof.

[Compound C]

A compound of the formula (I'), wherein $R^1$ is $C_{1-6}$ alkyl, $C_{3-6}$ cycloalkyl or $C_{2-6}$ alkenyl, each of which optionally has 1 to 5 substituents selected from substituent group A;

$R^2$ is (i) a hydrogen atom, (ii) (a) $C_{1-6}$ alkyl, (b) $C_{2-6}$ alkenyl, (c) $C_{2-6}$ alkynyl, (d) $C_{3-6}$ cycloalkyl or (e) $C_{6-14}$ aryl, each of which optionally has 1 to 5 substituents selected from substituent group A, or (iii) a 6-membered nitrogen-containing heterocyclic group (e.g., pyridyl and the like) optionally having 1 to 5 substituents selected from substituent B;

$R^3$ is (i) a hydrogen atom, (ii) (a) $C_{1-6}$ alkyl or (b) $C_{2-6}$ alkenyl, each of which optionally has 1 to 5 substituents selected from substituent group A, or (iii) amino optionally having 1 or 2 substituents selected from (a) $C_{1-6}$ alkyl, (b) $C_{2-6}$ alkenyl, (c) $C_{2-6}$ alkynyl, (d) $C_{3-6}$ cycloalkyl and (e) $C_{6-14}$ aryl, each of which optionally has 1 to 5 substituents selected from substituent group A;

$R^{4a}$ and $R^{4b}$ are the same or different and each is (i) a hydrogen atom, (ii) a halogen atom, (iii) hydroxy optionally substituted by $C_{1-6}$ alkyl optionally having 1 to 5 substituents selected from substituent group A or (iv) $C_{1-6}$ alkyl optionally having 1 to 5 substituents selected from substituent group A;

$R^5$ is (i) a hydrogen atom or (ii) $C_{1-6}$ alkyl optionally having 1 to 5 substituents selected from substituent group A;

$R^6$ is (i) a hydrogen atom or (ii) $C_{1-6}$ alkyl optionally having 1 to 5 substituents selected from substituent group A; and X is an oxygen atom or a sulfur atom, or a salt thereof.

[Compound D]

A compound of the formula (I'), wherein $R^1$ is $C_{1-6}$ alkyl optionally having substituent(s) (e.g., 1 to 5 substituents selected from substituent group A);

$R^2$ is a hydrogen atom;

$R^3$ is a hydrogen atom or $C_{1-6}$ alkyl optionally having substituent(s) (e.g., 1 to 5 substituents selected from substituent group A);

$R^{4a}$ and $R^{4b}$ are the same or different and each is a hydrogen atom or a halogen atom;

$R^5$ is a hydrogen atom or $C_{1-6}$ alkyl optionally having substituent(s) (e.g., 1 to 5 substituents selected from substituent group A); and $R^6$ is a hydrogen atom, or a salt thereof.

[Compound E]

A compound of the formula (I'), wherein $R^1$ is $C_{1-6}$ alkyl optionally having 1 to 5 substituents selected from the group consisting of a halogen atom, nitro, cyano, hydroxy, optionally halogenated $C_{1-6}$ alkoxy, $C_{7-13}$ aralkyloxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl (e.g., phenyl), $C_{6-10}$ aryloxy, $C_{1-6}$ alkyl-carbonylamino, $C_{1-6}$ alkyl-carbonyloxy and heterocyclic group (e.g., a 5- or 6-membered heterocyclic group containing, besides a carbon atom, 1 to 3 hetero atoms selected from a nitrogen atom, an oxygen atom and a sulfur atom; for example, pyridyl and the like) (hereinafter to be abbreviated as "substituent group C");

$R^2$ is a hydrogen atom;

$R^3$ is a hydrogen atom or $C_{1-6}$ alkyl optionally having 1 to 5 substituents selected from substituent group C;

$R^{4a}$ and $R^{4b}$ are the same or different and each is a hydrogen atom or a halogen atom;

$R^5$ is a hydrogen atom or $C_{1-6}$ alkyl optionally having 1 to 5 substituents selected from substituent group C; and $R^6$ is a hydrogen atom, or a salt thereof.

[Compound F]

A compound represented by the formula

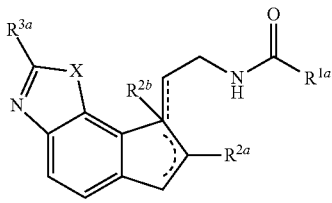

wherein $R^{1a}$ is (a) $C_{1-6}$ alkyl optionally having 1 to 3 substituents selected from $C_{1-6}$ alkyl-carbonyloxy, hydroxy and halogen atom, (b) $C_{3-6}$ cycloalkyl, (c) phenyl or (d) mono- or di-$C_{1-6}$ alkylamino;

$R^{2a}$ is a hydrogen atom or $C_{1-6}$ alkyl;

$R^{2b}$ is a hydrogen atom or hydroxy;

$R^{3a}$ is (a) a hydrogen atom, (b) $C_{1-6}$ alkyl optionally having 1 to 3 substituents selected from phenyl, hydroxy, a halogen atom, $C_{1-6}$ alkyl-carbonyl, $C_{7-13}$ aralkyloxy and pyridyl, (c) $C_{3-6}$ cycloalkyl, (d) phenyl, (e) $C_{1-6}$ alkoxy, (f) mercapto, (g) $C_{1-6}$ alkylthio or (h) mono- or di-$C_{1-6}$ alkylamino, or a salt thereof.

Preferable specific examples of compound (I) include N-[2-(2-methyl-6,7-dihydro-8H-indeno[5,4-d][1,3]oxazol-8-ylidene)ethyl]acetamide, N-[2-(2-methyl-6H-indeno[5,4-d][1,3]oxazol-8-yl)ethyl]acetamide, N-[2-(2-methyl-6,7-dihydro-8H-indeno[5,4-d][1,3]oxazol-8-ylidene)ethyl]propionamide, N-{2-[2-(4-phenylbutyl)-6,7-dihydro-8H-indeno[5,4-d][1,3]oxazol-8-ylidene]ethyl}acetamide, N-[2-(2-methyl-6,7-dihydro-8H-indeno[5,4-d][1,3]thiazol-8-ylidene)ethyl]acetamide, N-[2-(2-methyl-7,8-dihydro-6H-indeno[5,4-d][1,3]oxazol-8-yl)ethyl]acetamide, (R)-N-[2-(2-methyl-7,8-dihydro-6H-indeno[5,4-d][1,3]oxazol-8-yl)ethyl]acetamide, (S)-N-[2-(2-methyl-7,8-dihydro-6H-indeno[5,4-d][1,3]oxazol-8-yl)ethyl]acetamide, N-[2-(2-methyl-7,8-dihydro-6H-indeno[5,4-d][1,3]oxazol-8-yl)ethyl]propionamide, (R)-N-[2-(2-methyl-7,8-dihydro-6H-indeno[5,4-d][1,3]oxazol-8-yl)ethyl]propionamide, (S)-N-[2-(2-methyl-7,8-dihydro-6H-indeno[5,4-d][1,3]oxazol-8-yl)ethyl]propionamide, N-[2-(2-methyl-7,8-dihydro-6H-indeno[5,4-d][1,3]thiazol-8-yl)ethyl]acetamide, (R)-N-[2-(2-methyl-7,8-dihydro-6H-indeno[5,4-d][1,3]thiazol-8-yl)ethyl]acetamide, (S)-N-[2-(2-methyl-7,8-dihydro-6H-indeno[5,4-d][1,3]thiazol-8-yl)ethyl]acetamide, N-[2-(2-ethyl-7,8-dihydro-6H-indeno[5,4-d][1,3]oxazol-8-yl)ethyl]acetamide, (R)-N-[2-(2-ethyl-7,8-dihydro-6H-indeno[5,4-d][1,3]oxazol-8-yl)ethyl]acetamide, (S)-N-[2-(2-ethyl-7,8-dihydro-6H-indeno[5,4-d][1,3]oxazol-8-yl)ethyl]acetamide, N-[2-(2-methoxy-7,8-dihydro-6H-indeno[5,4-d][1,3]oxazol-8-yl)ethyl]acetamide, (R)-N-[2-(2-methoxy-7,8-dihydro-6H-indeno[5,4-d][1,3]oxazol-8-yl)ethyl]acetamide, (S)-N-[2-(2-methoxy-7,8-dihydro-6H-indeno[5,4-d][1,3]oxazol-8-yl)ethyl]acetamide or a salt thereof and the like.

As a salt of compound (I), for example, a pharmacologically acceptable salt and the like are used. For example, a salt with inorganic base, a salt with organic base, a salt with inorganic acid, a salt with organic acid, a salt with basic or acidic amino acid and the like can be mentioned. Preferable examples of salts with inorganic base include alkali metal salt such as sodium salt, potassium salt and the like, alkaline earth metal salt such as calcium salt, magnesium salt and the like, and aluminum salt, ammonium salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acid include salts with arginine, lysine, ornithine and the like, and preferable examples of salts with acidic amino acid include salts with aspartic acid, glutamic acid and the like. Of these, a pharmaceutically acceptable salt is preferable. Examples thereof when compound (I) has a basic functional group include salts with inorganic acid such as hydrochloric acid, hydrobromic acid, nitric acid, sulfuric acid, phosphoric acid and the like, and salts with organic acid such as acetic acid, phthalic acid, fumaric acid, tartaric acid, maleic acid, citric acid, succinic acid, methanesulfonic acid, p-toluenesulfonic acid and the like. Examples thereof when compound (I) has an acidic functional group include alkali metal salts such as sodium salt, potassium salt and the like, alkaline earth metal salts such as calcium salt, magnesium salt and the like, ammonium salt and the like.

The production methods of compound (I) of the present invention are described in the following.

Compound (I) of the present invention can be obtained, for example, by the method shown by the following reaction scheme or a method analogous thereto and the like.

Compounds (II)-(XXX) in the schemes include salts thereof. As the salt, for example, one similar to the salt of compound (I) and the like are used.

The compound obtained in each step can be directly used as a reaction mixture or a crude product for the next reaction. It can be isolated from a reaction mixture according to a conventional method, and can be easily purified by a separation means such as recrystallization, distillation, chromatography and the like.

In the following, reaction schemes are shown, wherein each symbol of the compound is as defined above.

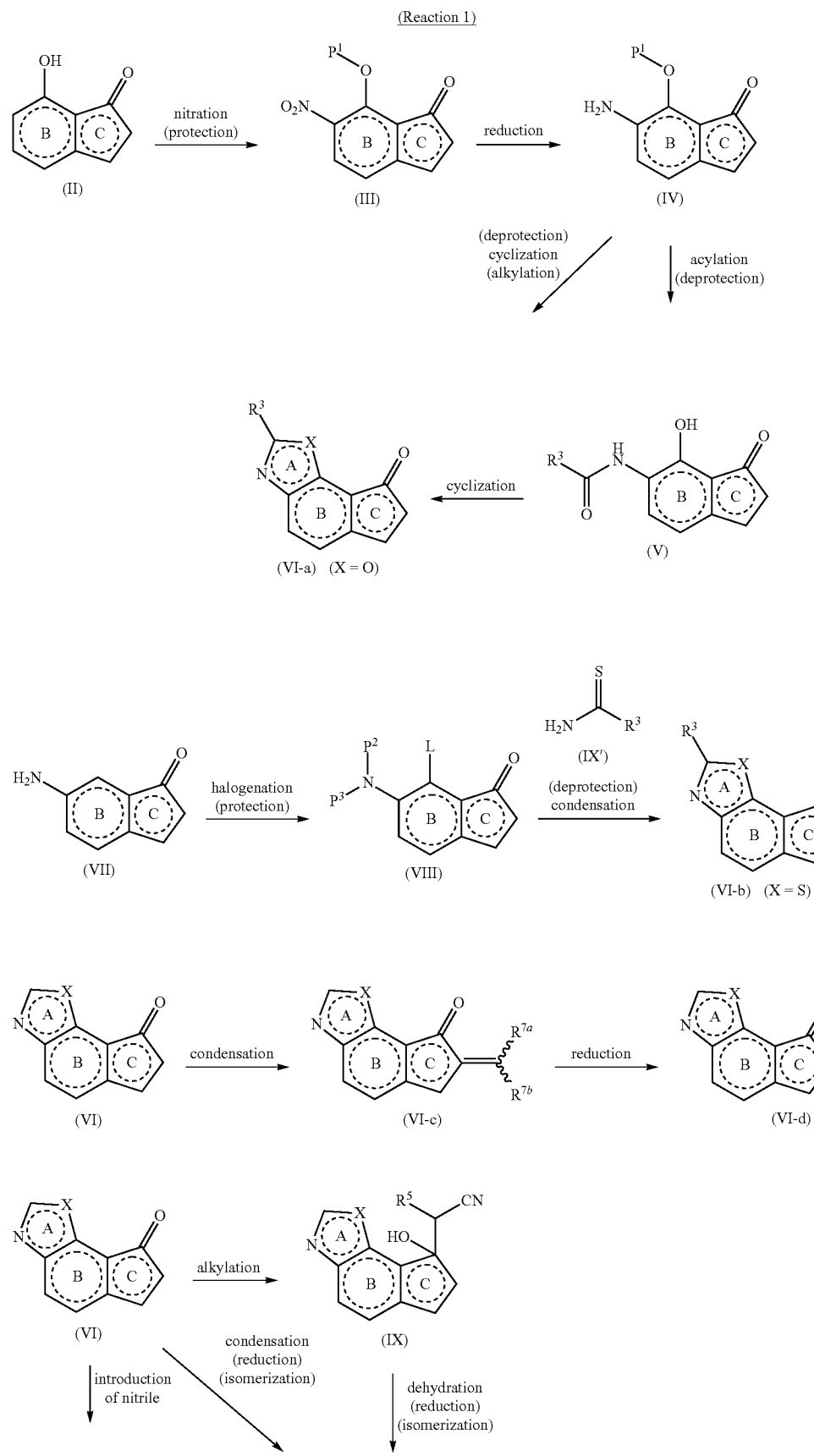

-continued

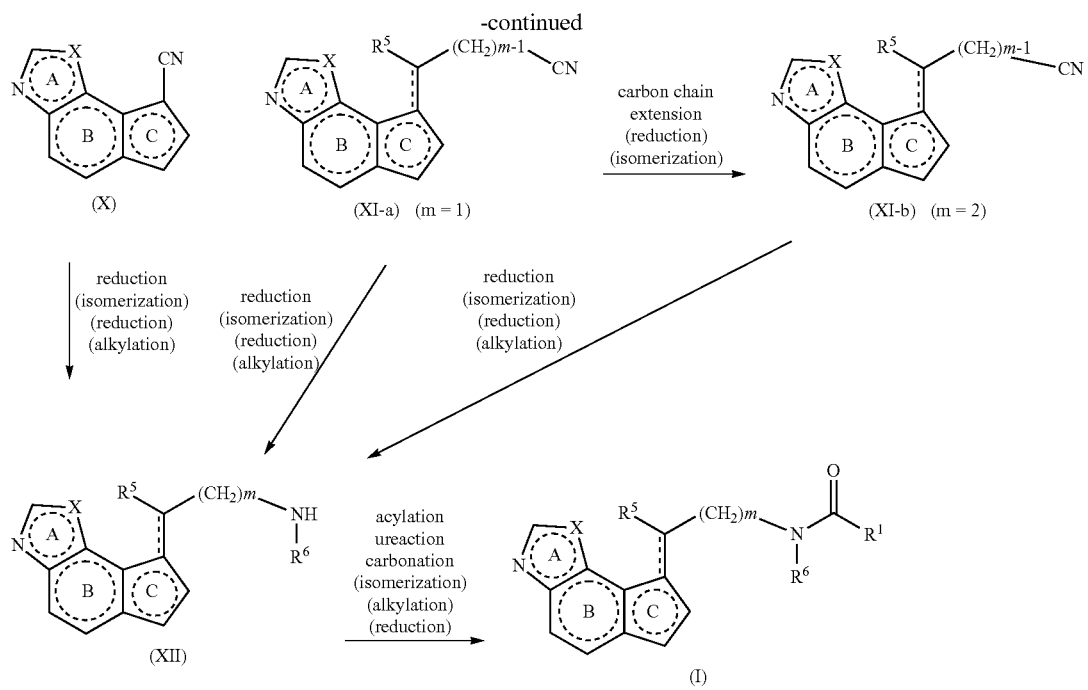

Compound (II) can be produced by a method known per se, for example, the methods described in J. Am. Chem. Soc., Vol. 71, p. 3523 (1949), J. Chem. Res. Miniprint, Vol. 11, p. 2544 (1995) and the like, or a method analogous thereto.

Compound (VII) can be produced by a method known per se, for example, the methods described in J. Chem. Soc., Vol. 123, p. 1469 (1923), J. Med. Chem., Vol. 46, p. 399 (2003) and the like, or a method analogous thereto.

Compound (IX') can be easily obtained from commercially available ones, or can also be produced by a method known per se, or a method analogous thereto.

When a compound in the schemes is commercially available, the commercially available product can be directly used.

Compound (III) can be produced by reacting compound (II) with a nitrating reagent. As the nitrating reagent, for example, metal nitrate salts such as sodium nitrate, potassium nitrate and the like, acetyl nitrate, dinitrogen pentaoxide, nitronium salt, nitric acid, mixed acid (mixture of nitric acid and sulfuric acid), and mixtures thereof can be mentioned. The nitrating reagent is used in an amount of about 0.8-20 mol, preferably about 1.0-2.0 mol, relative to 1 mol of compound (II). When nitric acid, mixed acid and the like are to be used as nitrating reagents, they can also be used in excess as reaction solvents. This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like), acid anhydrides (e.g., acetic anhydride and the like), organic acids (e.g., formic acid, acetic acid, propionic acid, trifluoroacetic acid, methanesulfonic acid and the like), inorganic acids (e.g., sulfuric acid and the like) and the like, or a mixed solvent thereof and the like are preferable. The reaction time is generally 10 min-24 hr, preferably 30 min-12 hr. The reaction temperature is generally −20° C.-150° C., preferably 0° C.-80° C.

The hydroxy of compound (III) may be protected by a protecting group when desired. As the protecting group, a group represented by $P^1$ [wherein $P^1$ is i) a hydrogen atom, ii) $C_{1-6}$ alkyl optionally having substituent(s) (e.g., methyl, ethyl and the like), $C_{7-10}$ aralkyl (e.g., benzyl, p-methoxybenzyl and the like), iii) $C_{1-6}$ alkyl-carbonyl optionally having substituent(s) (e.g., acetyl, propionyl and the like), benzoyl, $C_{1-6}$ alkoxy-carbonyl (e.g., methoxycarbonyl, ethoxycarbonyl, tert-butoxycarbonyl (Boc) and the like), allyloxycarbonyl (Aloc), phenoxycarbonyl, fluorenylmethyloxycarbonyl (Fmoc), $C_{7-10}$ aralkyl-carbonyl (e.g., benzylcarbonyl and the like), $C_{7-10}$ aralkyloxy-carbonyl (e.g., benzyloxycarbonyl (Z) and the like), or iv) $C_{1-6}$ alkyl-silyl optionally having substituent(s) (e.g., triethylsilyl, tert-butyldimethylsilyl and the like) or the like. As these substituents, 1 to 3 substituents selected from phenyl, a halogen atom (e.g., fluorine, chlorine, bromine, iodine and the like), $C_{1-6}$ alkyl-carbonyl (e.g., methylcarbonyl, ethylcarbonyl, butylcarbonyl and the like), nitro and the like can be mentioned] and the like can be mentioned. The protecting group can be introduced by a method known per se, for example, the method described in Wiley-Interscience, 1999 "Protective Groups in Organic Synthesis, 3$^{rd}$ Ed." (by Theodora W. Greene, Peter G. M. Wuts) and the like.

Compound (IV) can be produced by subjecting compound (III) to a reduction reaction. The reduction reaction is generally performed according to a conventional method using a reducing agent. As the reducing agent, for example, metal hydrides such as aluminum hydride, diisobutylaluminum hydride, tributyltin hydride and the like, metal hydride complex compounds such as sodium cyanoborohydride, sodium triacetoxyborohydride, sodium borohydride, lithium aluminum hydride and the like, borane complexes such as borane tetrahydrofuran complex, borane dimethyl sulfide complex and the like, alkylboranes such as thexylborane, disiamylborane and the like, diborane, metals such as zinc, aluminum, tin, iron and the like, alkali metal (e.g., sodium, lithium etc.)/liquid ammonia (Birch reduction), and the like can be mentioned. The amount of the reducing agent to be used is appropriately determined according to the kind of the reducing agent. For example, the amount of the metal hydride, the metal hydride complex compound, the borane complex, the alkylborane or the diborane to be used is about 0.25-10 mol, preferably about 0.5-5 mol, per 1 mol of compound (III) and the amount of the metals (including alkali metal to be used in Birch reduction) to be used is about 1.0-20 mol, preferably about 1.0-5.0 mol, per 1 mol of compound (III). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), organic acids (e.g., formic acid, acetic acid, propanoic acid, trifluoroacetic acid, methanesulfonic acid and the like), water and the like, or a mixed solvent thereof and the like are preferable. While the reaction time varies depending on the reagent and solvent to be used, it is generally 10 min-100 hr, preferably 30 min-50 hr. The reaction temperature is generally $-20°$ C.-$100°$ C., preferably $0°$ C.-$80°$ C.

The reduction reaction of compound (III) may be carried out by a hydrogenation reaction. In the case of a hydrogenation reaction, for example, a catalyst such as palladium carbon, platinum(IV) oxide, Raney nickel, Raney cobalt etc., and the like are used. The amount of the catalyst to be used is about 1.0-2000 wt %, preferably about 10-300 wt %, relative to compound (III). Various hydrogen sources can also be used instead of gaseous hydrogen. As the "hydrogen source", formic acid, ammonium formate, triethylammonium formate, sodium phosphinate, hydrazine and the like are used. The amount of the hydrogen source to be used is about 1.0-10 mol, preferably about 1.0-5.0 mol, per 1 mol of compound (III). This reaction is advantageously performed using a solvent inert to the reaction. For example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), organic acids (e.g., formic acid, acetic acid, propionic acid, trifluoroacetic acid, methanesulfonic acid and the like), esters (e.g., methyl acetate, ethyl acetate, butyl acetate and the like), water and the like, or a mixed solvent thereof and the like are preferable. The reaction time is generally 10 min-24 hr, preferably 30 min-12 hr. The reaction temperature is generally $-20°$ C.-$150°$ C., preferably $0°$ C.-$80°$ C. While the reaction time varies depending on the kind and amount of the reducing agent and the activity and amount of the catalyst to be used, it is generally 30 min-100 hr, preferably 1 hr-50 hr. The reaction temperature is generally $-20°$ C.-$120°$ C., preferably $0°$ C.-$80°$ C. When gaseous hydrogen is used, the pressure of hydrogen is generally 1-100 atm.

Compound (VI-a) wherein X is an oxygen atom can be produced by reacting compound (IV) with a carboxylic acid, a salt thereof or a reactive derivative thereof, to give compound (V), then subjecting compound (V) to cyclization reaction known per se. As the carboxylic acid, for example, a compound represented by the formula $R^3$—COOH, wherein $R^3$ is as defined above, can be mentioned. As the reactive derivative of the carboxylic acid, for example, acid halides such as acid chloride, acid bromide and the like, acid amides with pyrazole, imidazole, benzotriazole and the like, acid anhydrides such as acetic anhydride, propionic anhydride, butyric anhydride and the like, acid azides, active esters such as diethoxyphosphoric acid ester, diphenoxyphosphoric acid ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone and the like, active thioesters such as 2-pyridyl thioester, 2-benzothiazolyl thioester etc., and the like can be mentioned.

Instead of using the reactive derivative, the carboxylic acid or a salt thereof may be directly reacted with compound (IV) in the presence of a suitable condensation agent. As the condensation agent, for example, N,N'-disubstituted carbodiimides such as N,N'-dicyclohexylcarbodiimide, 1-ethyl-3-(3-dimethylaminopropyl)carbodiimide (WSC) hydrochloride and the like, azolides such as N,N'-carbonyldiimidazole and the like, dehydrating agents such as N-ethoxycarbonyl-2-ethoxy-1,2-dihydroquinoline, phosphorus oxychloride, alkoxyacetylene and the like, 2-halogenopyridinium salts such as 2-chloromethylpyridinium iodide, 2-fluoro-1-methylpyridinium iodide etc., and the like can be mentioned. When these condensation agents are used, the reaction is considered to proceed via a reactive derivative of carboxylic acid. The carboxylic acid or a reactive derivative thereof is generally used in an amount of about 1.0-5.0 mol, preferably about 1.0-2.0 mol, per 1 mol of compound (IV). This reaction is advantageously performed using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), aromatic amines (e.g., pyridine, lutidine and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like) and the like, or a mixed solvent thereof and the like are preferable. When an acidic substance is released due to the reaction, the reaction can be carried out in the presence of a deacidifying agent to remove the substance from the reaction system. As the deacidifying agent, for example, carbonates such as sodium carbonate, potassium carbonate, sodium hydrogencarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine etc., and the like can be used. While the reaction time varies depending on the reagent and solvent to be used, it is generally 10 min-24 hr, preferably 30 min-4 hr. The reaction temperature is generally 0° C.-100° C., preferably 0° C.-70° C.

As the cyclization reaction of compound (V), for example, a method using heating, a method using an acidic substance, a method analogous thereto and the like are used. In addition, compound (VI-a) may be directly produced from compound (IV) by the above-mentioned acylation step. Cyclization by heating is advantageously performed without solvent or using a solvent inert to the reaction. While the solvent is not particularly limited as long as the reaction proceeds, for example, solvents such as high boiling point hydrocarbons such as 1,2,3,4-tetrahydronaphthalene and the like, high boiling point ethers such as diphenyl ether, diethyleneglycol dimethyl ether and the like, aromatic hydrocarbons such as benzene, toluene, xylene etc., and the like, or a mixed solvent thereof and the like are preferable. The reaction time is generally 10 min-100 hr, preferably 1 hr-10 hr. The reaction temperature is generally 100° C.-300° C., preferably 100° C.-200° C.

For cyclization reaction using an acidic substance, for example, an acidic substance such as phosphorus oxychloride, phosphorus pentachloride, phosphorus trichloride, thionyl chloride, hydrochloric acid, sulfuric acid, polyphosphoric acid, p-toluenesulfonic acid, pyridinium p-toluenesulfonate and the like are used. The acidic substance is used in an amount of about 0.05-100 mol, preferably about 0.1-10 mol, per 1 mol of compound (V). This reaction is advantageously carried out without solvent or using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), sulfoxides (e.g., dimethyl sulfoxide and the like) and the like, or a mixed solvent thereof and the like are preferable. The reaction time is generally 10 min-100 hr, preferably 30 min-12 hr. The reaction temperature is generally 0° C.-200° C., preferably 0° C.-150° C.

Compound (VI-a) can also be produced by reacting compound (IV) with an ortho ester or an ortho carbonate. As the ortho ester, for example, triethyl orthoformate, trimethyl orthoacetate and the like can be mentioned. As the ortho carbonate, for example, tetramethoxyethane and the like can be mentioned. The ortho ester or ortho carbonate is generally used in an amount of about 1.0-100 mol, preferably about 1.0-10 mol, per 1 mol of compound (IV). The reaction is carried out, for example, by a method using heating, a method using an acidic substance, a method analogous thereto and the like. Cyclization by heating is advantageously performed without solvent or using a solvent inert to the reaction. While the solvent is not particularly limited as long as the reaction proceeds, solvents such as ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), sulfoxides (e.g., dimethyl sulfoxide and the like) and the like, or a mixed solvent thereof and the like are preferable. The reaction time is generally 10 min-100 hr, preferably 1 hr-24 hr. The reaction temperature is generally 0° C.-200° C., preferably 40° C.-150° C.

For cyclization reaction using an acidic substance, for example, an acidic substance such as phosphorus oxychloride, phosphorus pentachloride, phosphorus trichloride, thionyl chloride, hydrochloric acid, sulfuric acid, polyphosphoric acid, p-toluenesulfonic acid, pyridinium p-toluenesulfonate and the like are used. The acidic substance is used in an amount of about 0.05-100 mol, preferably about 0.1-10 mol, per 1 mol of compound (IV). This reaction is advantageously carried out without solvent or using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), sulfoxides (e.g., dimethyl sulfoxide and the like) and the like, or a mixed solvent thereof and the like are preferable. The reaction time is generally 10 min-100 hr, preferably 30 min-12 hr. The reaction temperature is generally 0° C.-200° C., preferably 0° C.-150° C.

Compound (VI-a) can also be produced by reacting compound (IV) with thiocarbonyl. As the thiocarbonyl, for example, potassium O-ethyl dithiocarbonate, carbon disulfide, thiocarbonyldiimidazole, thiophosgene, thiourea and the like can be mentioned. To promote the reaction, the reaction can be carried out in the presence of an acid or a base. As the acid, for example, inorganic acids such as hydrochloric acid, sulfuric acid, nitric acid, hydrobromic acid, phosphoric acid and the like, organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like, boron trifluoride ether complex and the like can be mentioned. As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate and the like, organic bases such as triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like, metal alkoxides such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide and the like, organic lithiums such as methyllithium, n-butyllithium, sec-butyllithium, tert-butyllithium etc., and the like can be mentioned. The thiocarbonyl is generally used in an amount of about 1.0-100 mol, preferably about 1.0-10 mol, per 1 mol of compound (IV). The acid or base is used in an amount of about 0.1-200 mol, preferably about 0.1-100 mol, per 1 mol of compound (IV). This reaction is advantageously carried out without solvent or using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like), esters (e.g., methyl acetate, ethyl acetate, butyl acetate and the like), ketones (e.g., acetone, methyl ethyl ketone and the like), aromatic organic bases (e.g., pyridine, lutidine and the like), acid anhydrides (e.g., acetic anhydride and the like), organic acids (e.g., formic acid, acetic acid, propionic acid, trifluoroacetic acid, methanesulfonic acid and the like), inorganic acids (e.g., sulfuric acid and the like), water and the like, or a mixed solvent thereof and the like are preferable. While the reaction time varies depending on the reagent and solvent to be used, it is generally 10 min-170 hr, preferably 1 hr-80 hr. The reaction temperature is generally 0° C.-250° C., preferably 0° C.-200° C. To promote the reaction, a microwave may be irradiated.

Compound (VI-a) can also be produced by reacting compound (IV) with dichloromethylene iminium or carbamoyl. As the dichloromethylene iminium, for example, dichloromethylenedimethyliminium chloride and the like can be mentioned. As the carbamoyl, for example, dimethylcarbamoyl chloride and the like can be mentioned. To promote the reaction, the reaction can be carried out in the presence of an acid or a base. As the acid, for example, inorganic acids such as hydrochloric acid, sulfuric acid, nitric acid, hydrobromic acid, phosphoric acid and the like, organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like, boron trifluoride ether complex and the like can be mentioned. As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate and the like, organic bases such as triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like, metal alkoxides such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide and the like, organic lithiums such as methyllithium, n-butyllithium, sec-butyllithium, tert-butyllithium etc., and the like can be mentioned. The dichloromethylene iminium or carbamoyl is generally used in an amount of about 1.0-100 mol, preferably about 1.0-10 mol, per 1 mol of compound (IV). The acid or base is used in an amount of about 0.1-200 mol, preferably about 0.1-100 mol, per 1 mol of compound (IV). This reaction is advantageously carried out without solvent or using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like), esters (e.g., methyl acetate, ethyl acetate, butyl acetate and the like), ketones (e.g., acetone, methyl ethyl ketone and the like), aromatic organic bases (e.g., pyridine, lutidine and the like), acid anhydrides (e.g., acetic anhydride and the like), organic acids (e.g., formic acid, acetic acid, propionic acid, trifluoroacetic acid, methanesulfonic acid and the like), inorganic acids (e.g., sulfuric acid and the like), water and the like, or a mixed solvent thereof and the like are preferable. While the reaction time varies depending on the reagent and solvent to be used, it is generally 10 min-170 hr, preferably 1 hr-80 hr. The reaction temperature is generally 0° C.-250° C., preferably 0° C.-200° C. To promote the reaction, a microwave may be irradiated.

$R^3$ of compound (VI-a) may be introduced by alkylation in the presence of a base using an alkylating agent when desired. As the alkylating agent, for example, alkyl halides such as methyl iodide, ethyl iodide and the like, sulfonic acid esters of alcohol and the like can be mentioned. The alkylating agent is used in an amount of about 0.8-50 mol, preferably about 1.0-10 mol, per 1 mol of compound (VI-a). As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide etc., and the like can be mentioned. The base is used in an amount of about 1.0-5.0 mol, preferably about 1.0-2.0 mol, per 1 mol of compound (VI-a). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like) and the like, or a mixed solvent thereof and the like are preferable. The reaction time is generally 30 min-48 hr, preferably 30 min-6 hr. The reaction temperature is generally −20° C.-200° C., preferably −10° C.-150° C.

Compound (VIII), wherein L is halogen atom and as the halogen atom for L, for example, fluorine, chlorine, bromine, iodine and the like can be mentioned, can be produced by reacting compound (VII) with a halogenating agent. As the halogenating agent, for example, phosphorus halides such as phosphorus trichloride, phosphorus oxychloride, phosphorus pentachloride, phosphorus tribromide, phosphorus triiodide and the like, succinimides such as N-bromosuccinimide, N-iodosuccinimide and the like, halogens such as chlorine, bromine, iodine, iodine(I) fluoride, iodine(I) chloride and the like, thionyl chloride, and mixtures thereof can be mentioned. The halogenating agent is used in an amount of about 1.0-100 mol, preferably about 1.0-10 mol, per 1 mol of compound (VII). To promote the reaction, the reaction can be carried out in the presence of a base. As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate etc., and the like can be mentioned. This reaction is advantageously carried out without solvent or using a solvent inert to the reaction. While the solvent is not particularly limited as long as the reaction proceeds, for example, alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like), acid anhydrides (e.g., acetic anhydride and the like), organic acids (e.g., formic acid, acetic acid, propionic acid, trifluoroacetic acid, methanesulfonic acid and the like), inorganic acids (e.g., sulfuric acid and the like), water or a mixed solvent thereof and the like are preferable. The reaction time is generally 10 min-50 hr, preferably 30 min-12 hr. The reaction temperature is generally 0° C.-200° C., preferably 10° C.-100° C.

The amino group of compound (VIII) may be protected with a protecting group when desired. As the protecting group, a group represented by $P^2$ or $P^3$ [wherein $P^2$ and $P^3$ are the same or different and each is i) a hydrogen atom, ii) formyl, or iii) $C_{1-6}$ alkyl-carbonyl (e.g., acetyl, propionyl and the like), benzoyl, $C_{1-6}$ alkoxy-carbonyl (e.g., methoxycarbonyl, ethoxycarbonyl, tert-butoxycarbonyl (Boc) and the like), allyloxycarbonyl (Aloc), phenoxycarbonyl, fluorenylmethyloxycarbonyl (Fmoc), $C_{7-10}$ aralkyl-carbonyl (e.g., benzylcarbonyl and the like), $C_{7-10}$ aralkyloxy-carbonyl (e.g., benzyloxycarbonyl (Z) and the like), $C_{7-10}$ aralkyl (e.g., benzyl and the like), trityl, phthaloyl or N,N-dimethylaminomethylene, each optionally having substituent(s), and the like. As the substituent, 1 to 3 substituents selected from phenyl, a halogen atom (e.g., fluorine, chlorine, bromine, iodine and the like), $C_{1-6}$ alkyl-carbonyl (e.g., methylcarbonyl, ethylcarbonyl, butylcarbonyl and the like), nitro and the like can be mentioned], and the like can be mentioned. The protecting group can be introduced by a method known per se, for example, the method described in Wiley-Interscience, 1999 "Protective Groups in Organic Synthesis, $3^{rd}$ Ed." (by Theodora W. Greene, Peter G. M. Wuts) and the like.

Compound (VI-b) can be produced by reacting compound (VIII) with thioamide (IX'). The reaction is generally carried out in the presence of a base. As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide etc., and the like can be mentioned. In addition, the reaction can also be promoted using a metal catalyst. As the metal catalyst, a metal complex having various ligands can be used and, for example, palladium compound [e.g.: palladium(II) acetate, tetrakis(triphenylphosphine)palladium(0), dichlorobis(triethylphosphine) palladium(II), tris(dibenzylideneacetone)dipalladium(0), [2,2'-bis(diphenylphosphino)-1,1'-binaphthyl]palladium(II) chloride, a complex of palladium(II) acetate and 1,1'-bis(diphenylphosphino)ferrocene, and the like], nickel compound [e.g.: tetrakis(triphenylphosphine)nickel(0), bis(triethylphosphine)nickel(II) chloride, bis(triphenylphosphine)nickel(II) chloride and the like], rhodium compound [e.g.: tris(triphenylphosphine)rhodium(III) chloride and the like], cobalt compound, copper compound [e.g.: copper oxide, copper(II) chloride and the like], platinum compound and the like can be mentioned. Of these, palladium compound, nickel compound and copper compound are preferable. The amount of thioamide (IX') to be used is about 0.8-10 mol, preferably about 1.0-3.0 mol, per 1 mol of compound (VIII). The amount of the base to be used is about 1.0-20 mol, preferably about 1.0-5.0 mol, per 1 mol of compound (VIII). The amount of the metal catalyst to be used is about 0.000001-5 mol, preferably about 0.0001-1 mol, per 1 mol of compound (VIII). When a metal catalyst unstable to oxygen is used in this reaction, for example, the reaction is preferably carried out in an inert gas stream of argon gas, nitrogen gas and the like. This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), esters (e.g., methyl acetate, ethyl acetate, butyl acetate and the like), sulfoxides (e.g., dimethyl sulfoxide and the like), sulfolane, hexamethylphosphoramide, water and the like, or a mixed solvent thereof and the like are preferable. The reaction temperature is −10° C.-250° C., preferably 0° C.-150° C. While the reaction time varies depending on compound (VIII), thioamide (IX'), the base, metal catalyst, the kind of the solvent, the reaction temperature and the like, it is generally 10 min-100 hr, preferably 30 min-50 hr.

Compound (VI-d) can be produced by aldol condensation reaction of compound (VI) with an aldehyde or ketone derivative to give compound (VI-c), then subjecting compound (VI-c) to a reduction reaction. Aldol condensation reaction is performed by a condensation of compound (VI) and an aldehyde or ketone derivative represented by the formula $R^{7a}COR^{7b}$ wherein $R^{7a}$ and $R^{7b}$ are the same or different and each is a hydrogen atom, a hydrocarbon group optionally having substituent(s), or a heterocyclic group optionally having substituent(s), in the presence of a base to give compound (VI-c) as a single configuration isomer of E isomer or Z isomer or a mixture of E and Z isomers. The amount of the aldehyde or ketone derivative to be used is about 1.0-50 mol, preferably about 1.0-5.0 mol, per 1 mol of compound (VI). As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide etc., and the like can be mentioned. The amount of the base to be used is about 1.0-5.0 mol, preferably about 1.0-2.5 mol, per 1 mol of compound (VI). In addition, basically-processed alumina (e.g., ICN Alumina B manufactured by ICN, Akt.1 and the like) and the like can also be used as a base. The amount of the alumina to be used is about 1 g-500 g, preferably about 5 g-100 g, per 1 g of compound (VI). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like) and the like, or a mixed solvent thereof and the like are preferable. The reaction time is generally 30 min-48 hr, preferably 30 min-5 hr. The reaction temperature is generally −78° C.-200° C., preferably −10° C.-150° C. In addition, the compound can also be produced by dehydrating an aldol type intermediate obtained in the presence of a base such as lithium diisopropylamide and the like, in the presence of an acid catalyst such as p-toluenesulfonic acid and the like at room temperature to under heating.

The reduction reaction can be generally carried out using a reducing agent according to a conventional method. As the reducing agent, for example, metal hydrides such as aluminum hydride, diisobutylaluminum hydride, tributyltin hydride and the like, metal hydride complex compounds such as sodium cyanoborohydride, sodium triacetoxyborohydride, sodium borohydride, lithium aluminum hydride and the like, borane complexes such as borane tetrahydrofuran complex, borane dimethyl sulfide complex and the like, alkylboranes such as thexylborane, disiamylborane and the like, diborane, metals such as zinc, aluminum, tin, iron and the like, alkali metal (e.g., sodium, lithium etc.)/liquid ammonia (Birch reduction), and the like can be mentioned. The amount of the reducing agent to be used is appropriately determined according to the kind of the reducing agent. For example, the amount of the metal hydride, the metal hydride complex compound, the borane complex, the alkylborane or the diborane to be used is about 0.25-10 mol, preferably about 0.5-5 mol, per 1 mol of compound (VI-c). The amount of the metals (including alkali metal to be used in Birch reduction) to be used is about 1.0-20 mol, preferably about 1.0-5.0 mol, per 1 mol of compound (VI-c). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), organic acids (e.g., formic acid, acetic acid, propanoic acid, trifluoroacetic acid, methanesulfonic acid and the like), water and the like, or a mixed solvent thereof and the like are preferable. While the reaction time varies depending on the reagent and solvent to be used, it is generally 10 min-100 hr, preferably 30 min-50 hr. The reaction temperature is generally −20° C.-100° C., preferably 0° C.-80° C.

In addition, compound (VI-c) can also be reduced by a hydrogenation reaction. In the case of hydrogenation reaction, for example, a catalyst such as palladium carbon, platinum(IV) oxide, Raney nickel, Raney cobalt etc., and the like are used. The amount of the catalyst to be used is about 1.0-2000 wt %, preferably about 10-300 wt %, relative to compound (VI-c). Various hydrogen sources can also be used instead of gaseous hydrogen. As the "hydrogen source", formic acid, ammonium formate, triethylammonium formate, sodium phosphinate, hydrazine and the like are used. The amount of the hydrogen source to be used is about 1.0-10 mol, preferably about 1.0-5.0 mol, per 1 mol of compound (VI-c). This reaction is advantageously performed using a solvent inert to the reaction. For example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), organic acids (e.g., formic acid, acetic acid, propionic acid, trifluoroacetic acid, methanesulfonic acid and the like), esters (e.g., methyl acetate, ethyl acetate, butyl acetate and the like) and the like, or a mixed solvent thereof and the like are preferable. The reaction time is generally 10 min-50 hr, preferably 30 min-24 hr. The reaction temperature is generally −20° C.-150° C., preferably 0° C.-80° C. While the reaction time varies depending on the kind and amount of the reducing agent and the activity and amount of the catalyst to be used, it is generally 30 min-100 hr, preferably 1 hr-50 hr. The reaction temperature is generally −20° C.-120° C., preferably 0° C.-80° C. When gaseous hydrogen is used, the pressure of hydrogen is generally 1-100 atm.

An aldehyde or ketone derivative represented by the formula $R^{7a}COR^{7b}$ can be easily obtained from commercially available ones, or can also be produced by a method known per se, or a method analogous thereto.

Compound (XI-a) wherein m is 1 can be produced by reacting carbanion, produced by treating nitrile with a base, with compound (VI) to give compound (IX), then subjecting compound (IX) to a dehydration reaction. Compound (XI-a) can be obtained as a single isomer or a mixture of isomers. As the nitrile, for example, a compound represented by the formula $R^5$—$CH_2CN$ can be mentioned. The nitrile is used in an amount of about 1.0-10 mol, preferably about 1.0-1.5 mol, per 1 mol of compound (VI). As the base, for example, metal alkoxides such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide etc., and the like can be mentioned. A base is used in an amount of about 1.0-10 mol, preferably about 1.0-1.5 mol, per 1 mol of compound (VI). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like) and the like, or a mixed solvent thereof and the like are preferable. While the reaction time varies depending on the reagent and solvent to be used, it is generally 30 min-48 hr, preferably 30 min-5 hr. The reaction temperature is generally –78° C.-100° C., preferably –78° C.-50° C.

As the catalyst to be used in the dehydration reaction, for example, acidic catalysts such as inorganic acids (e.g., hydrochloric acid, sulfuric acid, nitric acid, hydrobromic acid, phosphoric acid and the like), organic acids (e.g., acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like), boron trifluoride ether complex and the like, basic catalysts such as inorganic bases (e.g., sodium hydroxide, potassium hydroxide, magnesium hydroxide and the like), basic salts (e.g., sodium carbonate, potassium carbonate, cesium carbonate, calcium carbonate, sodium hydrogencarbonate and the like), and the like can be mentioned, further, for example, dehydrating agents such as diphosphorus pentaoxide, phosphorus oxychloride, phosphorus pentachloride, triphenylphosphine, phosgene, N,N'-dicyclohexylcarbodiimide, alumina, sodium dioxide, thionyl chloride, methanesulfonyl chloride, trifluoroacetic anhydride and the like can be used. This reaction is advantageously carried out without solvent or using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), sulfoxides (e.g., dimethyl sulfoxide and the like) and the like, or a mixed solvent thereof and the like are preferable. While the reaction time varies depending on the reagent and solvent to be used, it is generally 30 min-24 hr, preferably 30 min-5 hr. The reaction temperature is generally 0° C.-200° C., preferably 0° C.-150° C.

The nitrile derivative represented by the formula $R^5$—$CH_2CN$ may be a commercially available product, or can also be produced by a method known per se, or a method analogous thereto.

Compound (XI-a) wherein m is 1 can also be produced by reacting phosphonate carbanion, produced by treating alkylphosphonic acid diester with a base, with compound (VI). Compound (XI-a) can be obtained as a single isomer or a mixture of isomers. As the alkylphosphonic acid diester, for example, diethyl cyanomethylphosphonate, diethyl (1-cyanoethyl)phosphonate and the like are used. The alkylphosphonic acid diester is used in an amount of about 1.0-5.0 mol, preferably about 1.0-2.0 mol, per 1 mol of compound (VI). As the base, for example, metal alkoxides such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide etc., and the like can be mentioned. The base is used in an amount of about 1.0-5.0 mol, preferably about 1.0-1.5 mol, per 1 mol of compound (VI). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like) and the like, or a mixed solvent thereof and the like are preferable.

While the reaction time varies depending on the reagent and solvent to be used, it is generally 30 min-50 hr, preferably 1 hr-10 hr. The reaction temperature is generally –78° C.-200° C., preferably 0° C.-150° C.

Compound (X) can be produced by treating compound (VI) with trimethylsilyl cyanide in the presence of a Lewis acid and eliminating the resulting trimethylsilyloxy group with an acid. As the Lewis acid, for example, zinc iodide, anhydrous aluminum chloride, anhydrous zinc chloride, anhydrous iron chloride, boron trifluoride ether complex and the like can be mentioned. The Lewis acid is used in an amount of about 0.01-10 mol, preferably about 0.01-1.0 mol, per 1 mol of compound (VI). This reaction is advantageously carried out without solvent or using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like) and the like, or a mixed solvent thereof and the like are preferable. While the reaction time varies depending on the reagent and solvent to be used, it is generally 10 min-12 hr, preferably 30 min-3 hr. The reaction temperature is generally −10° C.-200° C., preferably −10° C.-100° C.

As the acid to be used for elimination of trimethylsilyloxy group, for example, inorganic acids such as hydrochloric acid, sulfuric acid, nitric acid, hydrobromic acid, phosphoric acid and the like, organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like, boron trifluoride ether complex and the like can be mentioned. The acid is used in an amount of about 1-100 mol, preferably about 1-10 mol, per 1 mol of compound (VI). This reaction is advantageously carried out without solvent or using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), sulfoxides (e.g., dimethyl sulfoxide and the like) and the like, or a mixed solvent thereof and the like are preferable. While the reaction time varies depending on the reagent and solvent to be used, it is generally 30 min-12 hr, preferably 30 min-5 hr. The reaction temperature is generally 0° C.-200° C., preferably 20° C.-150° C.

Compound (XI-b) wherein m is 2 can be produced by subjecting compound (XI-a) to a known carbon chain extension reaction or a reaction analogous thereto. For example, a cyano group is converted to a carboxy group by hydrolysis under alkaline or acidic conditions, or the carboxy group is led to an ester form, the obtained compound is subjected to a reduction reaction to give an alcohol compound, then the alcohol compound is subjected to a halogenation, a cyanation reaction and the like.

Compound (XII) can be produced as a single isomer or a mixture of isomers by subjecting compound (X), compound (XI-a) or compound (XI-b) to a reduction reaction. As the reducing agent, for example, metal hydrides such as aluminum hydride, diisobutylaluminum hydride and the like, metal hydride complex compounds such as lithium aluminum hydride, sodium borohydride and the like can be mentioned and, as the hydrogenation catalyst, for example, a catalyst such as Raney nickel, Raney cobalt etc., and the like can be mentioned. When the reducing agent is metal hydride, for example, about 1.0-10 mol, preferably about 1.0-3.0 mol, is used per 1 mol of compound (X), compound (XI-a) or compound (XI-b). When the reducing agent is a metal hydride complex compound, about 1.0-10 mol, preferably about 1.0-3.0 mol, is used per 1 mol of compound (X), compound (XI-a) or compound (XI-b). For hydrogenation, a catalyst such as Raney nickel, Raney cobalt and the like is used in an amount of about 10-5000 wt %, preferably about 100-2000 wt %, relative to compound (X), compound (XI-a) or compound (XI-b). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), esters (e.g., methyl acetate, ethyl acetate, butyl acetate and the like), organic acids (e.g., formic acid, acetic acid, propionic acid, trifluoroacetic acid, methanesulfonic acid and the like), water and the like, or a mixed solvent thereof and the like are preferable. When Raney nickel or Raney cobalt catalyst is used, amine such as ammonia and the like may be added to suppress the side reaction. While the reaction time varies depending on activity and amount of catalyst to be used, it is generally 30 min-200 hr, preferably 1 hr-50 hr. The reaction temperature is generally 0° C.-120° C., preferably 20° C.-80° C. When the catalyst such as Raney nickel, Raney cobalt and the like is used, the pressure of hydrogen is generally 1-100 atm.

Compound (I) can be produced by reacting compound (XII) with a carboxylic acid, a salt thereof or a reactive derivative thereof, or an isocyanate. As the carboxylic acid, for example, a compound represented by the formula $R^1$—COOH can be mentioned. As the reactive derivative of the carboxylic acid, for example, acid halides such as acid chloride, acid bromide and the like, acid amides with pyrazole, imidazole, benzotriazole and the like, acid anhydrides such as acetic anhydride, propionic anhydride, butyric anhydride and the like, acid azides, active esters such as diethoxyphosphoric acid ester, diphenoxyphosphoric acid ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone and the like, active thioesters such as 2-pyridyl thioester, 2-benzothiazolyl thioester etc., and the like can be mentioned. Instead of using the reactive derivative, the carboxylic acid or a salt thereof may be directly reacted with compound (XII) in the presence of a suitable condensation agent. As the condensation agent, for example, N,N'-disubstituted carbodiimides such as N,N'-dicyclohexylcarbodiimide, 1-ethyl-3-(3-dimethylaminopropyl)carbodiimide (WSC) hydrochloride and the like, azolides such as N,N'-carbonyldiimidazole and the like, dehydrating agents such as N-ethoxycarbonyl-2-ethoxy-1,2-dihydroquinoline, phosphorus oxychloride, alkoxyacetylene and the like, 2-halogenopyridinium salts such as 2-chloromethylpyridinium iodide, 2-fluoro-1-methylpyridinium iodide etc., and the like can be mentioned. When the condensation agent is used, the reaction is considered to proceed via a reactive derivative of carboxylic acid. As the isocyanate, for example, a compound represented by the formula $R^1$—NCO can be mentioned. The carboxylic acid, a salt thereof or a reactive derivative thereof, or the isocyanate is used in an amount of generally about 1.0-5.0 mol, preferably about 1.0-2.0 mol, per 1 mol of compound (XII). This reaction is advantageously performed using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like), aromatic organic bases (e.g., pyridine, lutidine and the like) and the like, or a mixed solvent thereof and the like are preferable. When an acidic substance is released by the reaction, the reaction can be carried out in the presence of a deacidifying agent to remove the substance from the reaction system. As the deacidifying agent, for example, basic salts such as sodium carbonate, potassium carbonate, cesium carbonate, calcium carbonate, sodium hydrogencarbonate and the like, organic bases such as triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene etc., and the like are used. While the reaction time varies depending on the reagent and solvent to be used, it is generally 10 min-24 hr, preferably 30 min-4 hr. The reaction temperature is generally 0° C.-100° C., preferably 0° C.-70° C.

Compound (I) can be produced by subjecting compound (XII) to carbonation reaction. The carbonation reaction can be carried out by a known method, for example, the method described in "Shin Jikken Kagaku Koza (New Experimental Chemistry Course)", Vol. 14, 15, pp. 230-239 (edited by the Chemical Society of Japan) and the like, or a method analogous thereto.

A carboxylic acid represented by the formula $R^1$—COOH, a salt thereof or a reactive derivative thereof, or an isocyanate represented by the formula $R^1$—NCO may be a commercially available product, or can also be produced by a method known per se, or a method analogous thereto.

A single isomer of compound (I) or a mixture of isomers of compound (I) can be converted to a different single isomer or a mixture of isomers at different ratio by a heat treatment, a treatment with an acid or a treatment with a base. As the acid, for example, inorganic acids such as hydrochloric acid, sulfuric acid, nitric acid, hydrobromic acid, phosphoric acid and the like, organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like, boron trifluoride ether complex and the like can be mentioned. As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate and the like, organic bases such as triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like, metal alkoxides such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide and the like, organic lithiums such as methyllithium, n-butyllithium, sec-butyllithium, tert-butyllithium etc., and the like can be mentioned. The acid or the base is used in an amount of about 0.01-100 mol, preferably about 0.01 to 5.0 mol, per 1 mol of compound (I). This reaction is advantageously carried out without solvent or using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), water and the like, or a mixed solvent thereof and the like are preferable. While the reaction time varies depending on the reagent and solvent to be used, it is generally 10 min-100 hr, preferably 30 min-24 hr. The reaction temperature is generally −10° C.-200° C., preferably −10° C.-150° C.

When a compound (I) wherein the double bond moiety is reduced is to be produced, the compound can be produced by subjecting the double bond moiety of compound (I) to a reduction reaction. The reduction reaction is generally carried out using a reducing agent according to a conventional method. As the reducing agent, for example, metal hydrides such as aluminum hydride, diisobutylaluminum hydride, tributyltin hydride and the like, metal hydride complex compounds such as sodium cyanoborohydride, sodium triacetoxyborohydride, sodium borohydride, lithium aluminum hydride and the like, borane complexes such as borane tetrahydrofuran complex, borane dimethyl sulfide complex and the like, alkylboranes such as thexylborane, disiamylborane and the like, diborane, metals such as zinc, aluminum, tin, iron and the like, alkali metal (e.g., sodium, lithium etc.)/liquid ammonia (Birch reduction) and the like can be mentioned. The amount of the reducing agent to be used is appropriately determined according to the kind of the reducing agent. For example, the metal hydride, the metal hydride complex compound, the borane complex, the alkylborane or the diborane is used in an amount of about 0.25-10 mol, preferably about 0.5-5 mol, per 1 mol of compound (I). The metals (including alkali metal to be used in Birch reduction) are used in an amount of about 1.0-20 mol, preferably about 1.0-5.0 mol, per 1 mol of compound (I). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), organic acids (e.g., formic acid, acetic acid, propionic acid, trifluoroacetic acid, methanesulfonic acid and the like), water and the like, or a mixed solvent thereof and the like are preferable. While the reaction time varies depending on the reagent and solvent to be used, it is generally 10 min-100 hr, preferably 30 min-50 hr. The reaction temperature is generally −20° C.-100° C., preferably 0° C.-80° C.

In addition, the double bond moiety can be reduced by subjecting compound (I) to a hydrogenation reaction. For hydrogenation reaction, for example, a catalyst such as palladium carbon, platinum(IV) oxide, Raney nickel, Raney cobalt etc., and the like is used. The catalyst is used in an amount of about 1.0-2000 wt %, preferably about 10-300 wt %, relative to compound (I). Various hydrogen sources can also be used instead of gaseous hydrogen. As the hydrogen source, for example, formic acid, ammonium formate, triethylammonium formate, sodium phosphinate, hydrazine and the like are used. The hydrogen source is used in an amount of about 1.0-10 mol, preferably about 1.0-5.0 mol, per 1 mol of compound (I). This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), esters (e.g., methyl acetate, ethyl acetate, butyl acetate and the like), organic acids (e.g., formic acid, acetic acid, propionic acid, trifluoroacetic acid, methanesulfonic acid and the like) and the like, or a mixed solvent thereof and the like are preferable. While the reaction time varies depending on the kind and amount of the reducing agent and the activity and amount of the catalyst to be used, it is generally 30 min-100 hr, preferably 1 hr-50 hr. The reaction temperature is generally −20° C.-120° C., preferably 0° C.-80° C. When hydrogenation catalyst is used, the pressure of hydrogen is generally 1-100 atm.

Of compounds (I), a compound wherein $R^6$ is a "hydrocarbon group optionally having substituent(s)" can be produced by subjecting a compound (I) wherein $R^6$ is a hydrogen atom to an alkylation reaction. The alkylation reaction includes reacting a compound (I) wherein $R^6$ is a hydrogen atom with a corresponding alkylating agent (e.g., alkyl halide, sulfonic acid ester of alcohol and the like) in the presence of a base. The alkylating agent is used in an amount of about 0.8-50 mol, preferably about 1.0-10 mol, per 1 mol of compound (I). As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate and the like, organic bases such as triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like, metal alkoxides such as sodium methoxide, sodium ethoxide, potassium tert-butoxide and the like, alkali metal hydrides such as sodium hydride, potassium hydride and the like, metal amides such as sodium amide, lithium diisopropylamide, lithium hexamethyldisilazide etc., and the like can be mentioned. The base is used in an amount of about 1.0-5.0 mol, preferably about 1.0-2.0 mol, per 1 mol of compound (I). This reaction is advantageously performed using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like) and the like, or a mixed solvent thereof and the like are preferable. While the reaction time varies depending on the reagent and solvent to be used, it is generally 30 min-48 hr, preferably 30 min-6 hr. The reaction temperature is generally −20° C.-200° C., preferably −10° C.-150° C.

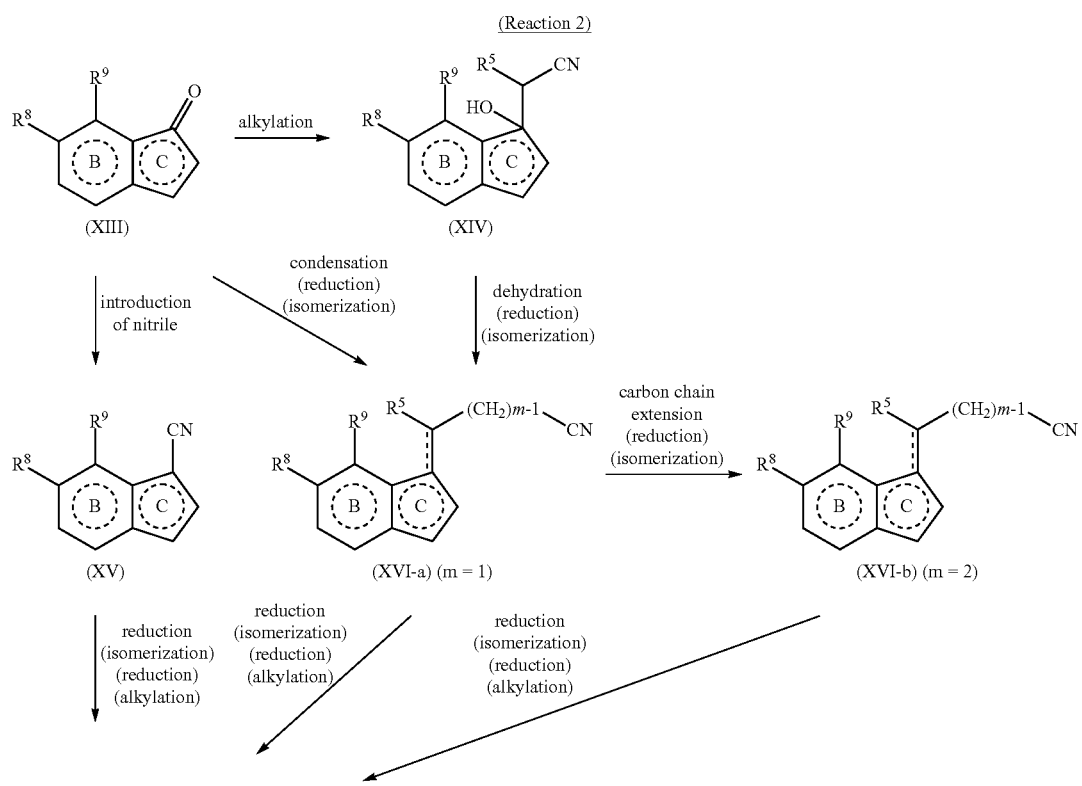

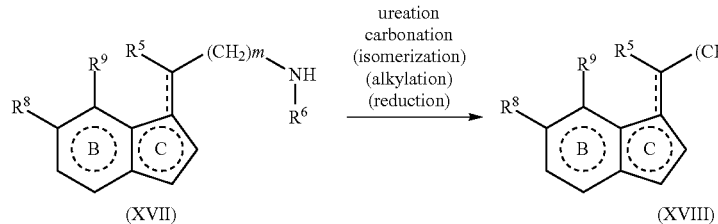

(Reaction 3)

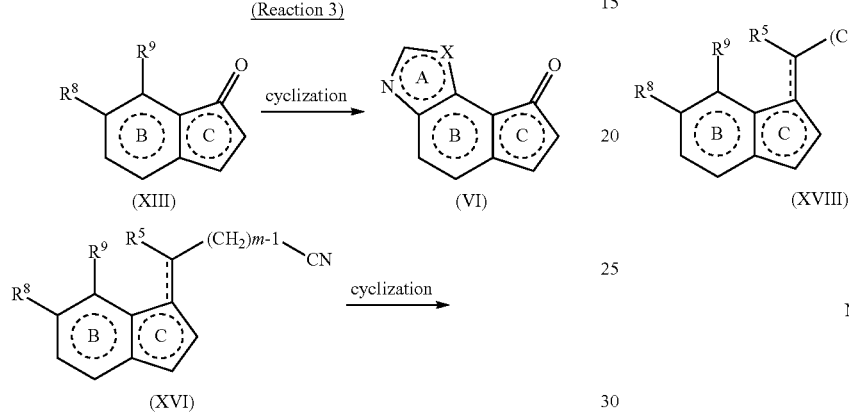

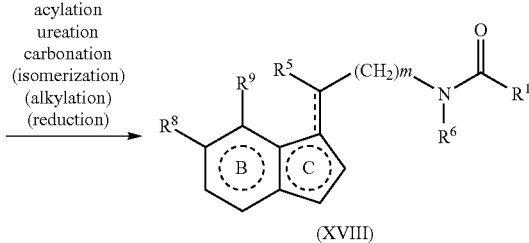

Compound (XVI-a) wherein m is 1 can be produced by reacting carbanion, produced by treating nitrile with a base, with compound (XIII) to give compound (XIV), and then subjecting compound (XIV) to a dehydration reaction. Compound (XIII) collectively shows compound (III) [$R^8$:—$NO_2$, $R^9$:—O—$P^1$], compound (IV) [$R^8$:—$NH_2$, $R^9$:—O—$P^1$], compound (V) [$R^8$:—NH—C(O)—$R^3$, $R^9$: —OH] and compound (VIII) [$R^8$:—$NP^2P^3$, $R^9$:-L], wherein each symbol is as defined above. Compound (XVI-a) is obtained as a single isomer or a mixture of isomers. The alkylation reaction and dehydration reaction can be carried out by a method similar to the method for producing compound (XI-a) from compound (VI).

Compound (XVI-a) can also be produced by subjecting phosphonate carbanion, produced by treating alkylphosphonic acid diester with a base, and compound (XIII) to a condensation reaction. The condensation reaction can be carried out by a method similar to the method for producing compound (XI-a) from compound (VI).

Compound (XVI-b) wherein m is 2 can be produced by subjecting compound (XVI-a) to a known carbon chain extension reaction or a reaction analogous thereto. The reaction can be carried out by a method similar to the method for producing compound (XI-b) from compound (XI-a).

Compound (XV) can be produced by treating compound (XIII) with trimethylsilyl cyanide in the presence of a Lewis acid, and eliminating the resulting trimethylsilyloxy group with an acid. The reaction can be carried out by a method similar to the method for producing compound (X) from compound (VI).

Compound (XVII) can be produced as a single isomer or a mixture of isomers by subjecting compound (XV), compound (XVI-a) or compound (XVI-b) to a reduction reaction. The reduction reaction can be carried out by a method similar to the method for producing compound (XII) from compound (X), compound (XI-a) or compound (XI-b).

Compound (XVIII) can be produced by reacting compound (XVII) with a carboxylic acid, a salt thereof or a reactive derivative thereof or an isocyanate or a carbonating agent. The acylation reaction, ureation reaction and carbonation reaction can be carried out by a method similar to the method for producing compound (I) from compound (XII).

Compounds (XI-a), (XI-b), (XII), (XVI-a), (XVI-b), (XVII) and (XVIII) can be converted to a different single isomer, or a mixture of isomers at different ratio by a method similar to the method for isomerizing compound (I).

Compound (XI-a), (XI-b), (XII), (XVI-a), (XVI-b), (XVII) or (XVIII), wherein the double bond moiety is reduced, can be produced by a method similar to the method for subjecting the double bond moiety of compound (I) to a reduction reaction.

Compound (XVIII) wherein $R^6$ is a "hydrocarbon group optionally having substituent(s)" can be produced by subjecting compound (XVIII) wherein $R^6$ is a hydrogen atom to an alkylation reaction. The alkylation reaction can be carried out by a method similar to the method for producing compound (I) wherein $R^6$ is a hydrocarbon group optionally having substituent(s) from compound (I) wherein $R^6$ is a hydrogen atom.

Compound (VI) can be produced by subjecting compound (XIII) to a series of reaction steps including a cyclization reaction. As the series of reaction steps including a cyclization reaction, for example, a method of producing compound (VI-a) from compound (IV), a method of producing compound (VI-b) from compound (VIII) and the like can be mentioned, and the reaction can be carried out by a method similar to the method of producing them.

Compound (XI) can be produced by subjecting compound (XVI) to a series of reaction steps including cyclization reaction. These reactions can be carried out by a method similar to the method for producing compound (VI) from compound (XIII).

Compound (X) can be produced by subjecting compound (XV) to a series of reaction steps including cyclization reaction. These reactions can be carried out by a method similar to the method for producing compound (VI) from compound (XIII).

Compound (XII) can be produced by subjecting compound (XVII) to a series of reaction steps including cyclization reaction. These reactions can be carried out by a method similar to the method for producing compound (VI) from compound (XIII).

Compound (I) can be produced by subjecting compound (XVIII) to a series of reaction steps including cyclization reaction. These reactions can be carried out by a method similar to the method for producing compound (VI) from compound (XIII).

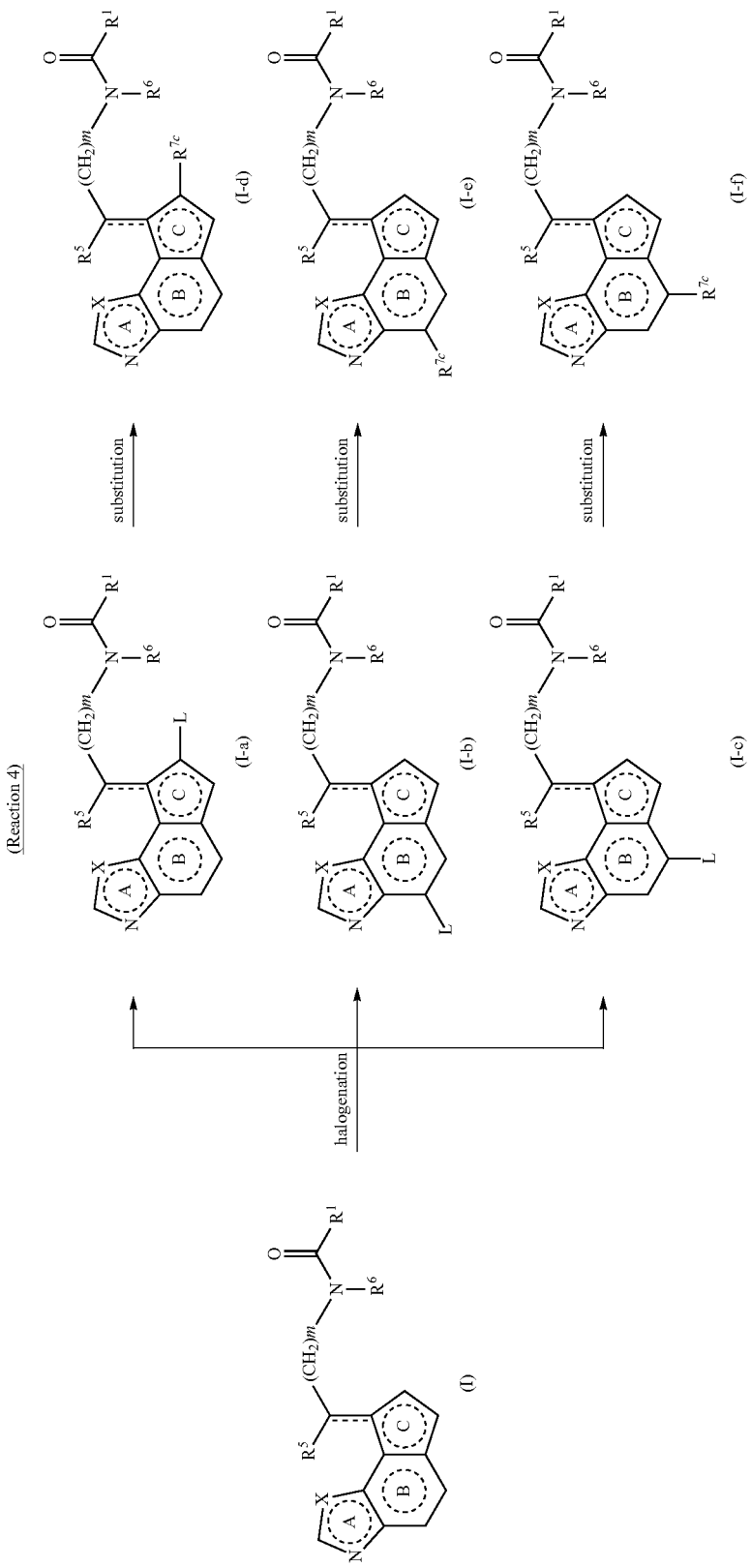

Compound (I-d) can be produced by reacting compound (I) with a halogenating agent to give compound (I-a), and then subjecting compound (I-a) to a condensation reaction. As the halogenating agent, for example, phosphorus halide such as phosphorus trichloride, phosphorus oxychloride, phosphorus pentachloride, phosphorus tribromide, phosphorus triiodide and the like, succinimides such as N-bromosuccinimide, N-iodosuccinimide and the like, halogens such as chlorine, bromine, iodine, iodine(I) fluoride, iodine(I) chloride and the like, thionyl chloride, and mixtures thereof and the like can be mentioned. The halogenating agent is used in an amount of about 1.0-100 mol, preferably about 1.0-10 mol, per 1 mol of compound (I). To promote the reaction, the reaction can be carried out in the presence of a base. As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate etc., and the like can be mentioned. This reaction is advantageously carried out without solvent or using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), sulfoxides (e.g., dimethyl sulfoxide and the like), acid anhydrides (e.g., acetic anhydride and the like), organic acids (e.g., formic acid, acetic acid, propionic acid, trifluoroacetic acid, methanesulfonic acid and the like), inorganic acids (e.g., sulfuric acid and the like), water and the like, or a mixed solvent thereof and the like are preferable. While the reaction time varies depending on the reagent and solvent to be used, it is generally 10 min-50 hr, preferably 30 min-12 hr. The reaction temperature is generally 0° C.-200° C., preferably 10° C.-100° C.

The condensation reaction can be carried out by reacting compound (I-a) with an organic boronic acid or an organic boronic acid ester in the presence of a metal catalyst. As the organic boronic acid or the organic boronic acid ester, for example, a compound represented by the formula $R^{7c}$-M wherein $R^{7c}$ is a hydrocarbon group optionally having substituent(s) or a heterocyclic group optionally having substituent(s), and M is a boron atom moiety of the organic boronic acid or the organic boronic acid ester, can be mentioned. As the M, for example, dihydroxyboranyl group, 4,4,5,5-tetramethyl-1,3,2-dioxaborolan-2-yl group and the like are preferable. As the metal catalyst, palladium compounds [e.g.: palladium(II) acetate, tetrakis(triphenylphosphine)palladium (0), dichlorobis(triethylphosphine)palladium(II), tris(dibenzylideneacetone)dipalladium(0), [2,2'-bis(diphenylphosphino)-1,1'-binaphthyl]palladium(II) chloride, a complex of palladium(II) acetate and 1,1'-bis(diphenylphosphino)ferrocene and the like] are preferable.

The reaction is generally carried out in the presence of a base. As the base, for example, inorganic bases such as sodium hydroxide, potassium hydroxide, magnesium hydroxide and the like, basic salts such as sodium carbonate, potassium carbonate, cesium carbonate, calcium carbonate, sodium hydrogencarbonate etc., and the like can be mentioned. The organic boronic acid or the organic boronic acid ester is used in an amount of about 0.1-10 mol, preferably about 0.8-2.0 mol, per 1 mol of compound (I-a). The metal catalyst is used in an amount of about 0.000001 to 5.0 mol, preferably about 0.0001-1.0 mol, per 1 mol of compound (I-a). The base is used in an amount of about 1.0-20 mol, preferably about 1.0-5.0 mol, per 1 mol of compound (I-a). When a metal catalyst unstable to oxygen is used in these reactions, for example, the reaction is preferably carried out in an inert gas stream of argon gas, nitrogen gas and the like. This reaction is advantageously performed using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), aromatic hydrocarbons (e.g., benzene, toluene, xylene and the like), saturated hydrocarbons (e.g., cyclohexane, hexane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like), nitriles (e.g., acetonitrile, propionitrile and the like), esters (e.g., methyl acetate, ethyl acetate, butyl acetate and the like), water and the like, or a mixed solvent thereof and the like are preferable. While the reaction time varies depending on the reagent and solvent to be used, it is generally 1 min-200 hr, preferably 5 min-100 hr. The reaction temperature is −10° C.-250° C., preferably 0° C.-150° C.

An organic boronic acid or an organic boronic acid ester represented by the formula $R^{7c}$-M may be a commercially available one, or can also be produced by a method known per se, or a method analogous thereto.

Compound (I-d) can also be produced by subjecting compound (I-a) to a desired substituent exchange reaction known per se. The reaction can be carried out, for example, by the method described in "Shin Jikken Kagaku Koza (New Experimental Chemistry Course)", Vols. 14 and 15, (edited by the Chemical Society of Japan) and the like, or a method analogous thereto.

Compounds (I-e) and (I-f) can be produced by a method similar to the method for producing compound (I-d) from compound (I).

Of compounds (I), a compound represented by the formula (I') or a salt thereof [hereinafter sometimes to be referred to as compound (I')] can be obtained by the method shown by the following reaction schemes, or a method analogous thereto and the like.

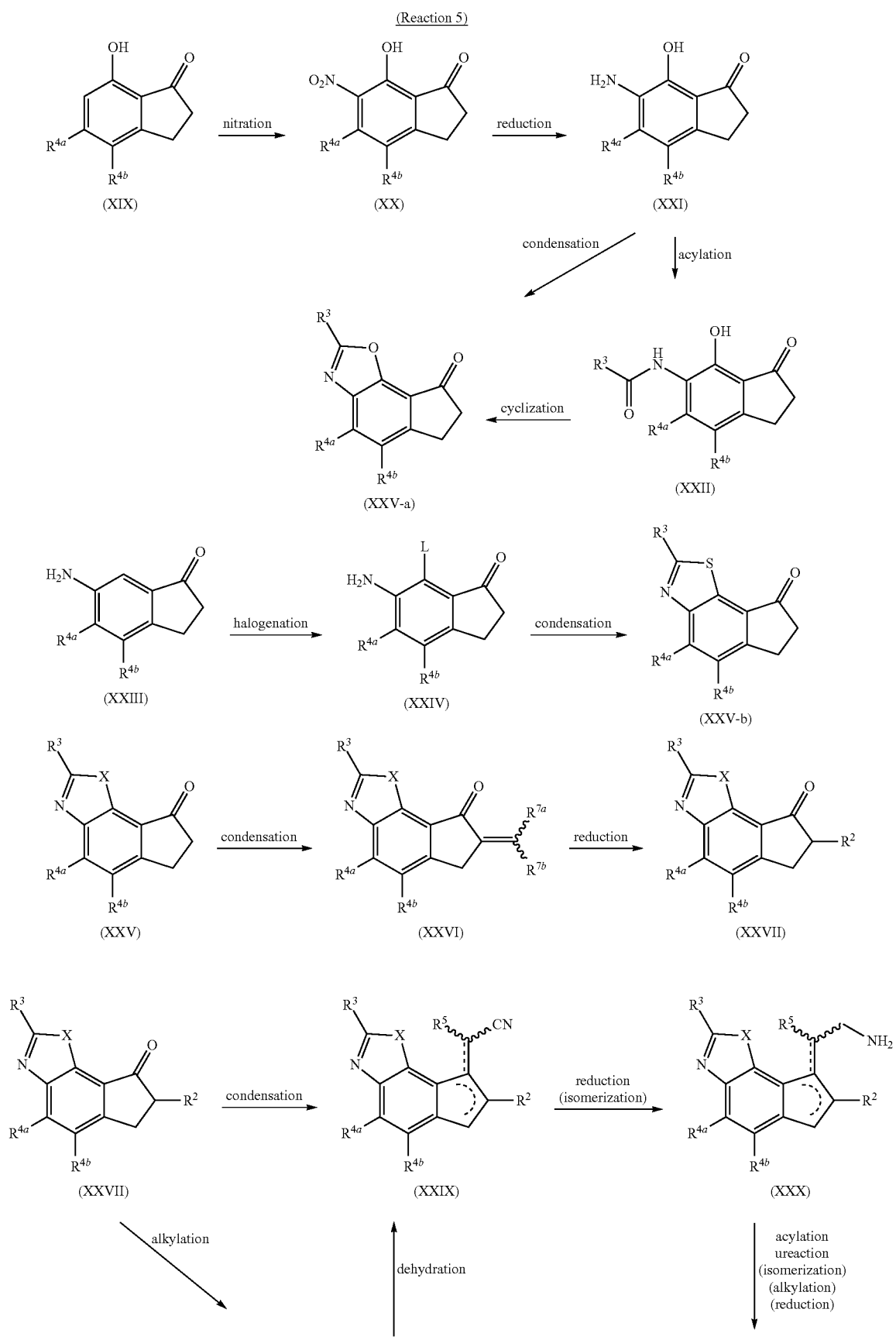

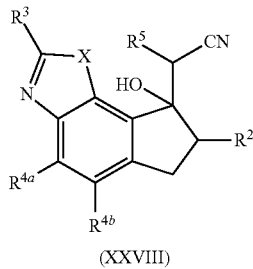

(XXVIII)

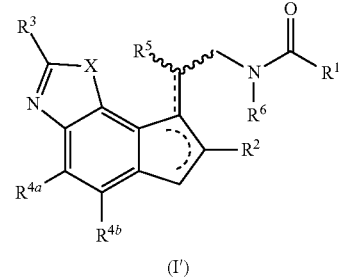

(I')

Compound (XIX) can be produced by a method similar to the method for producing compound (II). Compound (XXIII) can be produced by a method similar to the method for producing compound (VII).

Compound (XX) can be produced by a method similar to the method for producing compound (III); compound (XXI) can be produced by a method similar to the method for producing compound (IV); compound (XXII) can be produced by a method similar to the method for producing compound (V); compound (XXV-a) can be produced by a method similar to the method for producing compound (VI-a); compound (XXIV) can be produced by a method similar to the method for producing compound (VIII); compound (XXV-b) can be produced by a method similar to the method for producing compound (VI-b); compound (XXVI) can be produced by a method similar to the method for producing compound (VI-c); compound (XXVII) can be produced by a method similar to the method for producing compound (VI-d); compound (XXVIII) can be produced by a method similar to the method for producing compound (IX); compound (XXIX) can be produced by a method similar to the method for producing compound (XI-a); compound (XXX) can be produced by a method similar to the method for producing compound (XII); and compound (I') can be produced by a method similar to the method for producing compound (I) from compound (XII).

Of compounds (I'), a compound wherein $R^6$ is alkyl can be produced by subjecting a compound (I'-a) wherein $R^6$ is a hydrogen atom to an alkylation reaction. The alkylation reaction can be carried out in the same manner as in the alkylation reaction of compound (I) wherein $R^6$ is a hydrogen atom.

(Reaction 7)

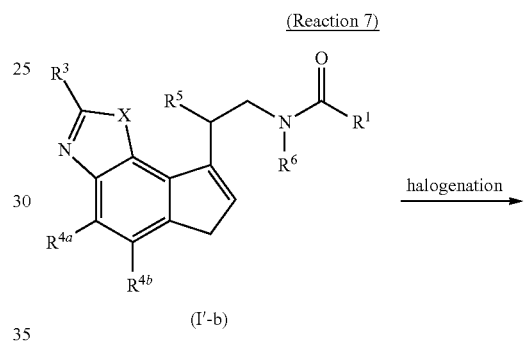

(I'-b)

halogenation →

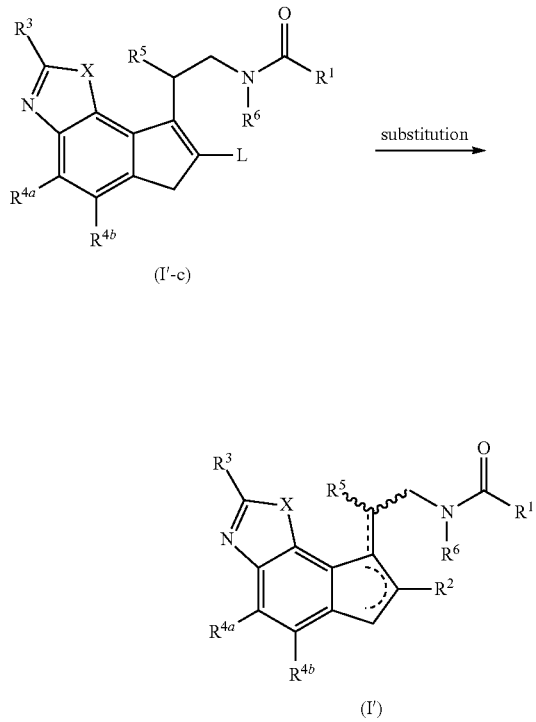

(Reaction 6)

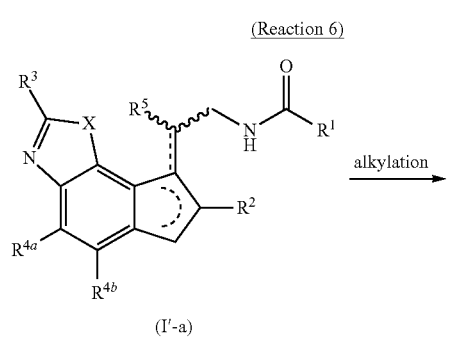

(I'-a)

alkylation →

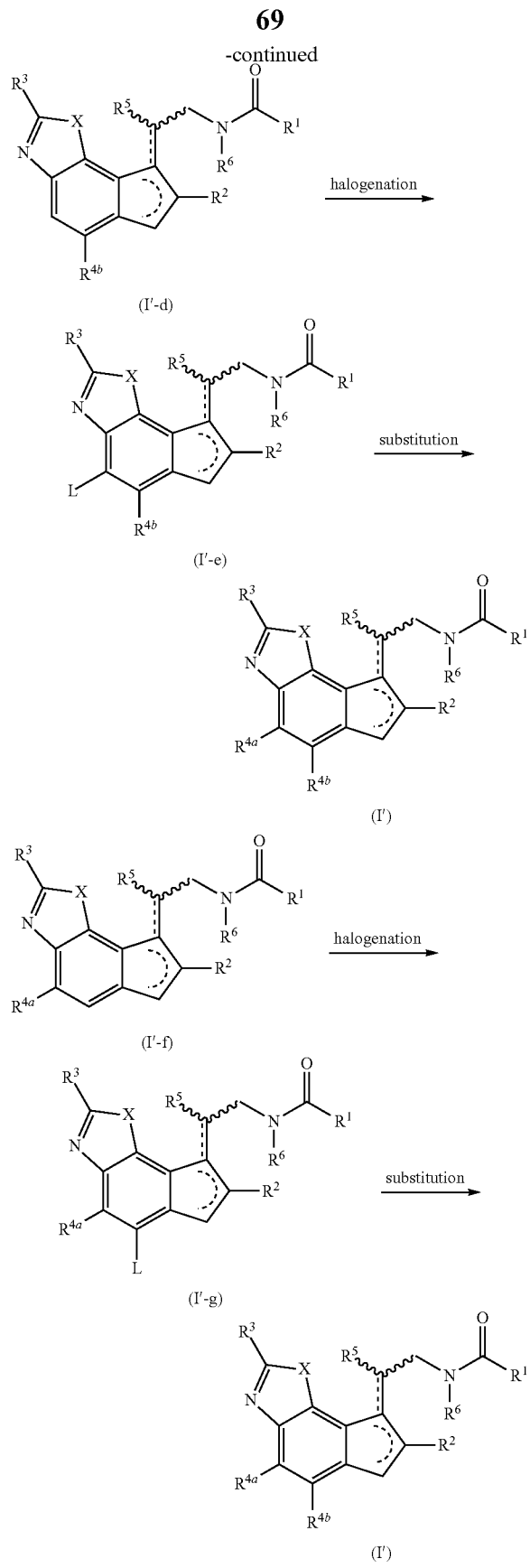

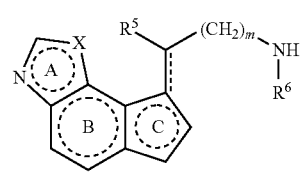

ing agent to give compound (I'-c) and then subjecting compound (I'-c) to a desired substituent exchange reaction known per se.

$R^{4a}$ of compound (I') can be introduced by reacting compound (I'-d) wherein $R^{4a}$ is a hydrogen atom with a halogenating agent to give compound (I'-e) and then subjecting compound (I'-e) to a desired substituent exchange reaction known per se.

$R^{4b}$ of compound (I') can be introduced by reacting compound (I'-f) wherein $R^{4b}$ is a hydrogen atom with a halogenating agent to give compound (I'-g) and then subjecting compound (I'-g) to a desired substituent exchange reaction known per se.

The halogenation and substituent exchange reaction can be carried out by a method similar to the method for producing, for example, compound (I-d) from compound (I).

A compound represented by the formula wherein each symbol is as defined above, or a salt thereof, which is obtained in the reaction steps for the production of the aforementioned compound (I), is a novel compound, and can be used as a starting material of the compound of the present invention. Of these, preferable compounds include 2-(6,7-dihydro-8H-indeno[5,4-d][1,3]oxazol-8-ylidene) ethanamine, 2-(2-methyl-6,7-dihydro-8H-indeno[5,4-d][1,3]oxazol-8-ylidene)ethanamine, 2-[2-(4-phenylbutyl)-6,7-dihydro-8H-indeno[5,4-d][1,3]oxazol-8-ylidene] ethanamine, 2-(2-methyl-6,7-dihydro-8H-indeno[5,4-d][1,3]thiazol-8-ylidene)ethanamine, 2-(2-methyl-7,8-dihydro-6H-indeno[5,4-d][1,3]oxazol-8-yl)ethanamine or an optically active form thereof or a salt thereof and the like.

In the aforementioned respective reactions, when the starting material compound has amino, carboxy, hydroxy or heterocyclic group, these groups may be protected by a protecting group generally used in the peptide chemistry and the like. In this case, the object compound can be obtained by removing the protecting group as necessary after the reaction. Introduction and removal of these protecting groups can be performed by a method known per se, for example, the method described in "*Protective Groups in Organic Synthesis, 3rd Ed.*" (Theodora W. Greene, Peter G. M. Wuts, Wiley-Interscience, 1999) and the like.

The configuration isomers of the aforementioned compounds (II)-(XXX) can be isolated and purified by, for example, a conventional separation means such as extraction, recrystallization, distillation, chromatography and the like, when isomerization occurs, whereby a pure compound can be produced. In addition, isomerization of double bond may be promoted by heating, acid catalyst, transition metal complex, metal catalyst, radical species catalyst, photoirradiation or strong basic catalyst and the like according to the method described in Shin Jikken Kagaku Koza (New Experimental Chemistry Course), vol. 14, pp. 251-253 (edited by the Chemical Society of Japan), Jikken Kagaku Koza (Courses in Experimental Chemistry), 4th Ed., vol. 19, pp. 273-274 (edited by the Chemical Society of Japan) and the like or a method analogous thereto, whereby a corresponding pure isomer can be obtained. While compound (I) has a stereoiso- $R^2$ of compound (I') can be introduced by reacting compound (I'-b) wherein $R^2$ is a hydrogen atom with a halogenatmer depending on the kind of the substituent, not only the isomer itself but also a mixture thereof are encompassed in the present invention. In the above-mentioned reaction steps, where desired, compound (I) can be produced by a known hydrolysis, deprotection, acylation reaction, alkylation reaction, hydrogenation reaction, oxidation reaction, reduction reaction, carbon chain extension reaction or substituent exchange reaction, conducted individually or by a combination of two or more thereof. These reactions can be carried out, for example, according to the method described in Shin Jikken Kagaku Koza (New Experimental Chemistry Course), vols. 14 and 15 (edited by the Chemical Society of Japan) and the like.

Compound (I) can be isolated and purified by a known means, for example, phase transfer, concentration, solvent extraction, fractional distillation, liquid conversion, crystallization, recrystallization, chromatography and the like.

If compound (I) is obtained as a free compound, it can be converted into a desired salt by a method known per se or a modification thereof; conversely, if compound (I) is obtained as a salt, it can be converted into a free form or another desired salt by a method known per se or a modification thereof.

The compound (I) may be used as a prodrug. A prodrug of the compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (*Development of Pharmaceuticals*), Vol. 7, Design of Molecules, p. 163-198, Published by HIROKAWA SHOTEN.

When compound (I) has isomers such as optical isomer, stereoisomer, positional isomer, rotational isomer and the like, and any isomers and mixtures are encompassed in the compound (I). For example, when compound (I) has an optical isomer, an optical isomer separated from a racemate is also encompassed in the compound (I). These isomers can be obtained as independent products by a synthesis means or a separation means (e.g., concentration, solvent extraction, column chromatography, recrystallization and the like), optical resolution methods (e.g., fractional recrystallization, chiral column method, diastereomer method and the like) and the like known per se.

The compound (I) may be a crystal, and both a single crystal and crystal mixtures are encompassed in the compound (I) of the present invention. Crystals can be produced by crystallization according to crystallization methods known per se.

The compound (I) may be a solvate (e.g., hydrate etc.) or a non-solvate (e.g., non-hydrate etc.), both of which are encompassed in the compound (I).

A compound labeled with an isotope (e.g., $^{3}H$, $^{14}C$, $^{35}S$, $^{125}I$ and the like) is also encompassed in the compound (I).

Compound (I) shows high affinity for melatonin receptors ($MT_1$ receptor, $MT_2$ receptor). Since compound (I) acts as a melatonin agonist, has physiological activities such as melatonin receptor affinity and the like, shows low toxicity (e.g., acute toxicity, chronic toxicity, genetic toxicity, reproductive toxicity, cardiotoxicity, drug interaction, carcinogenicity and the like), and is superior in the stability and in vivo kinetics (absorption, distribution, metabolism, excretion and the like), it is useful as a pharmaceutical product. Compound (I) acts as a melatonin agonist in mammals (e.g., mouse, rat, hamster, rabbit, cat, dog, bovine, sheep, monkey, human and the like), is useful as a composition with a binding affinity for melatonin receptor, particularly, a melatonin receptor agonist, and can be used as a prophylactic or therapeutic drug for a disease possibly influenced by melatonin. As the "disease possibly influenced by melatonin", for example, sleep disorders [e.g., intrinsic sleep disorders (e.g., psychophysiological insomnia and the like), extrinsic sleep disorders, circadian rhythm disorders (e.g., time-zone change syndrome (jet lag), shift work sleep disorder, irregular sleep-wake pattern, delayed sleep phase syndrome, advanced sleep phase syndrome, non-24 hour sleep-wake syndrome and the like), parasomnias, sleep disorder associated with internal or psychic disorders (e.g., chronic obstructive pulmonary disease, Alzheimer's disease, Parkinson's disease, cerebrovascular dementia, schizophrenia, depression, anxiety neurosis), insomnia and the like], neurodegenerative diseases (e.g., senile dementia, Alzheimer's disease, Parkinson's disease, Creutzfeldt-Jakob disease, amyotrophic lateral sclerosis (ALS), Huntington's disease, spinocerebellar degeneration, multiple sclerosis (MS) and the like), psychoneurotic diseases (e.g., depression, anxiety, bipolar disorder, posttraumatic stress disorder (PTSD), seasonal melancholia, schizophrenia and the like), memory disorders (e.g., senile dementia, mild cognitive impairment (MCI), amnesia and the like), ischemic central nerve disorders (e.g., cerebral infarction, cerebral hemorrhage, brain edema and the like), central nervous system injury (e.g., head trauma, spinal cord injury, whiplash injury and the like), vascular dementia (e.g., multi-infarct dementia, Binswanger's disease and the like), cancer (e.g., cerebral tumor, pituitary adenoma, glioma, acoustic neurinoma, retina sarcoma, thyroid cancer, pharyngeal cancer, laryngeal cancer, lingual cancer, thymoma, mesothelial tumor, breast cancer, lung cancer, non-small cell lung cancer, small cell lung cancer, stomach cancer, esophageal cancer, duodenal cancer, colorectal cancer, colon cancer, rectal cancer, liver cancer, hepatocellular carcinoma, pancreatic cancer, pancreatic endocrine tumor, biliary tract cancer, gallbladder cancer, penile cancer, kidney cancer, renal pelvic cancer, ureteral cancer, renal cell cancer, testis tumor, prostate cancer, bladder cancer, vulvar cancer, uterine cancer, cancer of uterine cervix, cancer of uterine body, uterine sarcoma, chorionic disease, vaginal cancer, ovarian cancer, ovarian germ cell tumor, skin cancer, malignant melanoma, mycosis fungoides, basal cell tumor, soft tissue sarcoma, malignant lymphoma, Hodgkin's disease, osteomyelodysplasia syndrome, multiple myeloma, leukemia, acute myelocytic leukemia, chronic myelocytic leukemia, acute lymphatic leukemia, chronic lymphatic leukemia, adult T cell leukemia, chronic myeloproliferative disease, pancreatic endocrine tumor, fibrous histiocytoma, leiomyosarcoma, rhabdomyosarcoma, unknown primary cancer and the like), hyperinsulinemia, metabolic syndrome, obesity, diabetes, diabetic complications (e.g., diabetic retinopathy, diabetic neuropathy, diabetic nephropathy and the like), hypertriglyceridemia (hyperlipidemia), hypertension, circulatory disease [e.g., ischemic cardiac diseases (e.g., myocardial infarction, angina pectoris and the like), cerebral apoplexy, arteriosclerosis, arterial restenosis after PTCA and the like], lower urinary tract disease or disorder (e.g., dysuria, incontinence and the like), osteoporosis, reproductive and neuroendocrine diseases, convulsion, glaucoma, headache, irritable bowel syndrome and the like can be mentioned. In addition, it is effective for immunoregulation, cognitive enhancement, tranquilization, stress or regulation of ovulation (e.g., contraception and the like).

Compound (I) or a prodrug thereof [sometimes to be abbreviated as "the compound of the present invention"] can be safely administered orally or parenterally (e.g., subcutaneous, topical, rectal, intravenous administrations etc.) by itself, or in the form of a pharmaceutical composition containing a pharmacologically acceptable carrier according to a conventional method (e.g., the method described in the Japanese Pharmacopoeia etc.), such as tablet (including sugar-coated tablet, film-coated tablet and the like), powder, granule, capsule, liquid, emulsion, suspension, injection, suppository, sustained-release preparation (e.g., sublingual tablet, microcapsule etc.), plaster, orally disintegrating tablet, orally disintegrating film and the like.

As pharmacologically acceptable carriers, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidant, coloring agent, sweetening agent, adsorbent, wetting agent and the like can be used appropriately.

As the excipient, for example, lactose, sucrose, D-mannitol, starch, cornstarch, crystalline cellulose, light anhydrous silicic acid and the like can be mentioned. As the lubricant, for example, magnesium stearate, calcium stearate, talc, colloidal silica and the like can be mentioned. As the binder, for example, crystalline cellulose, sucrose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like can be mentioned. As the disintegrant, for example, starch, carboxymethylcellulose, calcium carboxymethylcellulose, croscarmellose sodium, sodium carboxymethyl starch, L-hydroxypropylcellulose and the like can be mentioned. As the solvent, for example, water for injection, alcohol, propylene glycol, macrogol, sesame oil, corn oil, olive oil and the like can be mentioned. As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned. As the suspending agent, for example, surfactants such as stearyltriethanolamine, sodium lauryl sulfate, lauryl aminopropionate, lecithin, benzalkonium chloride, benzethonium chloride, glyceryl monostearate, and the like; for example, hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose etc., and the like can be mentioned. As the isotonicity agent, for example, glucose, D-sorbitol, sodium chloride, glycerol, D-mannitol and the like can be mentioned. As the buffer, for example, buffer such as phosphate, acetate, carbonate, citrate etc., and the like can be mentioned. As the soothing agent, for example, benzyl alcohol and the like can be mentioned. As the preservative, for example, p-hydroxybenzoates, chlorobutanol, benzyl alcohol, phenethyl alcohol, dehydroacetic acid, sorbic acid and the like can be mentioned. As the antioxidant, for example, sulfite, ascorbic acid, α-tocopherol and the like can be mentioned.

While the dose of the compound of the present invention varies depending on the subject of administration, administration route and symptom and is not particularly limited, for example, for oral administration to adult patients for the treatment of insomnia, it is about 0.001 to about 3 mg/kg body weight, preferably about 0.005 to about 2 mg/kg body weight, more preferably about 0.01 to about 1 mg/kg body weight, as the compound of the present invention, which is the active ingredient. The dose is desirably administered about 1 to 3 times a day according to the symptom.

The content of the compound of the present invention in the above-mentioned "agent (pharmaceutical composition)" is about 0.01 to 100 wt % of the whole composition.

When the compound of the present invention is applied to each of the above-mentioned diseases, it can be used in appropriate combination with a pharmaceutical agent or a treatment method generally employed for the disease.

In the following, a combined use of the compound of the present invention with a concomitant drug is referred to as "the combination agent of the present invention".

As such concomitant drug, for example, sleep inducing agents (e.g., GABA system sleep inducing agent such as brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol etc.; non-GABA system sleep inducing agent such as eplivaserin, pruvanserin, diphenhydramine, trazodone, doxepin etc., and the like), antidepressants (e.g., fluoxetine, sertraline, paroxetine, venlafaxine, nefazodone, reboxetine, mirtazapine, imipramine hydrochloride, duloxetine, escitalopram, mifepristone, doxepin, etc.), antianxiety agents (e.g., alprazolam, bromazepam, chlordiazepoxide, diazepam, etizolam, flutoprazepam, lorazepam, etc.), therapeutic agents for Alzheimer's disease (e.g., cholinesterase inhibitors such as donepezil, rivastigmine, galanthamine, zanapezil etc.; cerebral function activators such as idebenone, memantine, vinpocetine etc.; agents for suppressing progression such as Alzhemed etc., and the like), antiparkinson agents (e.g., L-DOPA, deprenyl, carbidopa+levodopa, pergolide, ropinirole, cabergoline, pramipexole, entacaprone, lazabemide etc.), therapeutic agents for amyotrophic lateral sclerosis (e.g., riluzole, mecasermin, gabapentin, etc.), neurotrophic factors, therapeutic agents for schizophrenia (e.g., olanzapine, risperidone, quetiapine, iloperidone, etc.), hypolipidemic agents (e.g., simvastatin, fluvastatin, pravastatin, atorvastatin, etc.), antihypertensive agents (e.g., captopril, delapril, enalapril, nifedipine, nicardipine, amlodipine, alprenolol, propranolol, metoprolol, losartan, valsartan, candesartan, etc.), therapeutic agents for diabetes (e.g., pioglitazone, rosiglitazone, metformin, glibenclamide, nateglinide, voglibose, etc.), antiplatelet agents (e.g., ticlopidine, heparin, urokinase, alteplase, tisokinase, nasaruplase, cilostazol, etc.), antioxidants (e.g., linolenic acid, ascorbic acid, icosapentaenoic acid, docosahexaenoic acid, tocopherol, etc.), vitamins (e.g., tocopherol, ascorbic acid, etc.), sex hormones (e.g., estrogen, estrone, estradiol, etc.), antiinflammatory agents (e.g., prednisolone, betamethasone, dexamethasone, etc.), nonsteroidal antiinflammatory agents (e.g., indomethacin, ibuprofen, acetylsalicylic acid, diclofenac, naproxen, piroxicam, etc.), COX-2 inhibitors (e.g., celecoxib, rofecoxib, etc.), cerebral circulation metabolism improving agents (e.g., nicergoline, ibudilast, ifenprodil, etc.), anticonvulsants (e.g., carbamazepine, valproic acid, clonazepam, vigabatrin, lamotrigine, gabapentin, etc.) and pharmacologically acceptable salts thereof and the like can be mentioned.

By combining the compound of the present invention and a concomitant drug, a superior effect such as
(1) the dose can be reduced as compared to single administration of the compound of the present invention or a concomitant drug,
(2) the concomitant drug can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

A combination agent of the present invention has low toxicity, and for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules, solutions, emulsions, suspensions, injections, suppositories, sustained release preparations (e.g., sublingual tablet, microcapsule etc.), plasters, orally disintegrating tablets, orally disintegrating films and the like, which can be safely administered orally or parenterally (e.g., subcutaneous, topical, rectal, intravenous administrations etc.).

As pharmacologically acceptable carriers usable for the production of the combination agent of the present invention, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidant, coloring agent, sweetening agent, adsorbent, wetting agent and the like can be used appropriately.

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the administration amount clinically used, and can be appropriately selected depending on an administration subject, administration route, disease, combination and the like.

Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention varies depending on the form of a preparation, and usually from about 0.01 to 100 wt %, preferably from about 0.1 to 50 wt %, further preferably from about 0.5 to 20 wt %, based on the whole preparation.

While the content of the concomitant drug in the combination agent of the present invention varies depending on the form of a preparation, it is usually from about 0.01 to 100 wt %, preferably from about 0.1 to 50 wt %, further preferably from about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of the compound of the present invention and the concomitant drug.

The SEQ ID NOs in the sequence listing in the present specification shows the following sequences.
SEQ ID NO: 1 shows the base sequence of cDNA fragment encoding the full-length human melatonin 1 receptor (human $MT_1$ receptor). (see Gen Bank ACCESSION No. NM_005958)
SEQ ID NO: 2 shows the base sequence of cDNA fragment encoding the full-length human melatonin 2 receptor (human $MT_2$ receptor). (see Gen Bank ACCESSION No. NM_005959)

The present invention is explained in detail in the following by referring to Reference Examples, Examples, Formulation Examples and Experimental Examples. However, the examples are mere exemplifications and do not limit the present invention. The present invention may be modified without departing from the scope of the invention.

In the following Reference Examples and Examples, the "room temperature" means generally about 10° C. to about 35° C., % means mol/mol % for the yield, % by volume for the solvent used for chromatography, and wt % for others.

Other abbreviations used in the text mean the following.

s: singlet
d: doublet
t: triplet
q: quartet
m: multiplet
br: broad
J: coupling constant
Hz: Hertz
CDCl$_3$: deuteriochloroform
DMSO-d$_6$: deuteriodimethyl sulfoxide
METHANOL-d$_4$: deuteriomethanol
$^1$H-NMR: proton nuclear magnetic resonance
ee: enantiomer excess The elution for the column chromatography in the Examples was performed under observation by TLC (Thin Layer Chromatography). In the TLC observation, 60F254 manufactured by Merck or NH manufactured by Fuji Silysia Chemical Ltd. was used as a TLC plate.

Unless otherwise specified, the silica gel packed in the column was silica gel 60 (70-230 mesh) (manufactured by Merck) or PURIF-pack (SI 60 μm) (manufactured by Moritex Corporation). When described as silica gel chromatography (NH), CHROMATOREX-NH DM1020 (100-200 mesh) (manufactured by Fuji Silysia Chemical Ltd.) or PURIF-pack (NH 60 μm) (manufactured by Moritex Corporation) was used. Unless otherwise specified, moreover, the elution solvent for silica gel column chromatography is in volume ratio.

As Raney cobalt, Raney cobalt catalyst ODHT-60 (manufactured by Kawaken Fine Chemicals Co., Ltd.) was used after washing with water and ethanol.

In the following Reference Examples and Examples, $^1$H-NMR spectrum was measured using tetramethylsilane as the internal standard and the chemical shift is expressed in δ value and the coupling constant is expressed in Hz.

In the following Reference Examples and Examples, melting point, mass spectrum (MS), specific rotation, and nuclear magnetic resonance spectrum (NMR) were measured under the following conditions.
Melting point apparatus: Yanagimoto micromelting point apparatus, or Buchi B-545 melting point apparatus
MS measurement instrument: Waters ZMD, or Waters ZQ, ionization
method: Electron Spray Ionization (ESI)
Polarimeter: JASCO P-1030
NMR measurement instrument: Varian, Inc., Varian Mercury 300 (300 MHz), Bruker BioSpin AVANCE 300 (300 MHz)

REFERENCE EXAMPLE 1

4-Bromophenyl acrylate

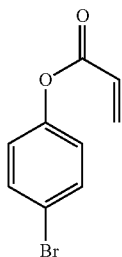

To a solution of 4-bromophenol (15.1 g, 87.3 mmol) in tetrahydrofuran (170 mL) was added 60% sodium hydride (3.68 g, 91.6 mmol) under ice-cooling and the mixture was stirred for 15 min. A solution of acryloyl chloride (8.3 g, 91.6 mmol) in tetrahydrofuran (50 mL) was added, and the mixture was stirred for 15 min under ice-cooling. Water was added, and the solvent was evaporated under reduced pressure. The residue was extracted with ethyl acetate, washed with saturated brine and dried over anhydrous sodium sulfate. The solvent was evaporated under reduced pressure, and the residue was purified by silica gel column chromatography (ethyl acetate/hexane=20/80) to give the title compound (18.1 g, yield 100%).
$^1$H-NMR (CDCl$_3$) δ: 6.03 (1H, dd, J=10.5, 1.1 Hz), 6.31 (1H, dd, J=17.3, 10.5 Hz), 6.61 (1H, dd, J=17.3, 1.1 Hz), 7.03 (2H, d, J=9.1 Hz), 7.50 (2H, d, J=9.1 Hz).

REFERENCE EXAMPLE 2

4-Bromo-7-hydroxyindan-1-one

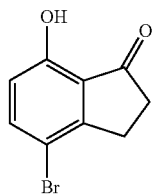

To a mixture of aluminum trichloride (120 g) and sodium chloride (40 g) heated to 100° C. was added 4-bromophenyl acrylate (10.5 g, 50.7 mmol), and the mixture was stirred for 15 min. Then, the mixture was heated to 140° C., and the mixture was stirred for 45 min. The mixture was poured into ice-cooled water and extracted with ethyl acetate. The extract was washed with saturated brine and dried over anhydrous sodium sulfate. The solvent was evaporated under reduced pressure, and the residue was purified by silica gel column chromatography (ethyl acetate/hexane=20/80) and recrystallized (ethyl acetate/hexane) to give the title compound (3.82 g, yield 36%).
$^1$H-NMR (CDCl$_3$) δ: 2.68-2.83 (2H, m), 2.99-3.09 (2H, m), 6.71 (1H, d, J=8.8 Hz), 7.58 (1H, d, J=8.8 Hz), 9.01 (1H, s).

REFERENCE EXAMPLE 3

4-Bromo-7-hydroxy-6-nitroindan-1-one

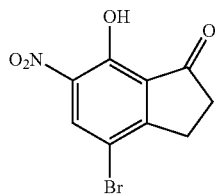 [SMILES: O=C1CCc2c(Br)cc([N+](=O)[O-])c(O)c21]

4-Bromo-7-hydroxyindan-1-one (3.06 g, 13.5 mmol) was suspended in acetic acid (20 mL), and acetic anhydride (1.66 mL, 17.6 mmol) and fuming nitric acid (838 μL, 20.2 mmol) dissolved in acetic acid (10 mL) were added. The mixture was stirred at room temperature for 3 hr. The solvent was evaporated under reduced pressure and the precipitated yellow crystals were collected by filtration to give the title compound (2.98 g, yield 79%).

¹H-NMR (CDCl₃) δ: 2.83-2.92 (2H, m), 3.08-3.16 (2H, m), 8.50 (1H, s), 10.99 (1H, s),
melting point: 149-151° C. (recrystallized from methanol),
Elemental analysis: for $C_9H_6BrNO_4$
Calcd. (%): C, 39.73; H, 2.22; N, 5.15
Found (%): C, 39.88; H, 2.40; N, 5.37.

REFERENCE EXAMPLE 4

6-Amino-7-hydroxyindan-1-one hydrobromide

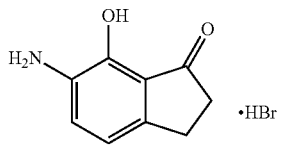

4-Bromo-7-hydroxy-6-nitroindan-1-one (2.90 g, 10.66 mmol) was dissolved in methanol (53 mL), a 10% palladium-carbon powder (290 mg) was added, and the mixture was stirred at room temperature for 6 hr under a hydrogen atmosphere. The catalyst was filtered off using celite, and the filtrate was concentrated under reduced pressure to give the title compound (2.08 g, yield 80%).

¹H-NMR (METHANOL-d₄) δ: 2.69-2.82 (2H, m), 3.12-3.21 (2H, m), 7.13 (1H, d, J=8.0 Hz), 7.57 (1H, d, J=8.0 Hz), hidden (4H).

REFERENCE EXAMPLE 5

N-(4-Hydroxy-3-oxo-2,3-dihydro-1H-inden-5-yl)acetamide

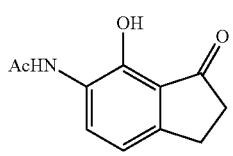

6-Amino-7-hydroxyindan-1-one hydrobromide (800 mg, 3.28 mmol) was suspended in tetrahydrofuran (20 mL), triethylamine (571 μL, 4.10 mmol) and acetic anhydride (387 μL, 4.10 mmol) were added, and the mixture was stirred at room temperature for 1.5 hr. To the reaction solution was added saturated aqueous sodium hydrogencarbonate solution. The mixture was extracted with ethyl acetate, washed with saturated brine and dried over anhydrous sodium sulfate. The solvent was evaporated under reduced pressure, and the residue was purified by silica gel column chromatography (ethyl acetate/hexane=60/40→100/0) to give the title compound (481 mg, yield 71%).

¹H-NMR (CDCl₃) δ: 2.23 (3H, s), 2.70-2.78 (2H, m), 3.07-3.13 (2H, m), 6.95 (1H, d, J=8.3 Hz), 7.51 (1H, brs), 8.51 (1H, d, J=8.2 Hz), 9.17 (1H, brs).

REFERENCE EXAMPLE 6

N-(4-Hydroxy-3-oxo-2,3-dihydro-1H-inden-5-yl)-5-phenylpentanamide

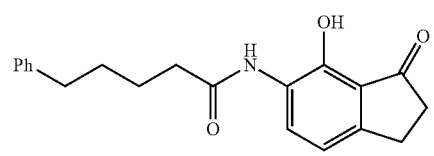 [SMILES: O=C(CCCCc1ccccc1)Nc1ccc2c(c1O)C(=O)CC2]

6-Amino-7-hydroxyindan-1-one hydrobromide (50 mg, 0.256 mmol) and 5-phenylvaleric acid (54.8 mg, 0.307 mmol) were dissolved in N,N-dimethylformamide (1.3 mL), diethyl cyanophosphate (45.7 μL, 0.307 mmol) and triethylamine (120 μL, 0.896 mmol) were added, and the mixture was stirred at room temperature for 15 min. The reaction solution was diluted with diethyl ether, washed with water and saturated brine, and dried over anhydrous sodium sulfate. The solvent was evaporated under reduced pressure, and the residue was purified by silica gel column chromatography (ethyl acetate/hexane=10/90→40/60) to give the title compound (21.8 mg, yield 26%).

¹H-NMR (CDCl₃) δ: 1.68-1.86 (4H, m), 2.44 (2H, t, J=7.0 Hz), 2.67 (2H, t, J=7.0 Hz), 2.71-2.77 (2H, m), 3.04-3.14 (2H, m), 6.95 (1H, d, J=8.0 Hz), 7.12-7.22 (3H, m), 7.23-7.32 (2H, m), 7.48 (1H, brs), 8.54 (1H, d, J=8.0 Hz), 9.17 (1H, s),
melting point: 119-121° C. (recrystallized from hexane/ethyl acetate),
MS (ESI+): 324 (M+H),
Elemental analysis: for $C_{20}H_{21}NO_3 \cdot 0.1H_2O$
Calcd. (%): C, 73.87; H, 6.57; N, 4.31
Found (%): C, 73.94; H, 6.47; N, 4.20.

REFERENCE EXAMPLE 7

6,7-Dihydro-8H-indeno[5,4-d][1,3]oxazol-8-one

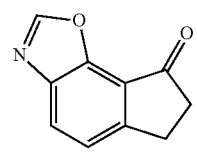 [SMILES: O=C1CCc2ccc3ncoc3c21]

6-Amino-7-hydroxyindan-1-one hydrobromide (50 mg, 0.205 mmol) and triethyl orthoformate (128 μL, 0.769 mmol) were heated under reflux in tetrahydrofuran (2.5 mL) for 0.5 hr. The mixture was diluted with ethyl acetate, washed with saturated brine and dried over anhydrous sodium sulfate. The solvent was evaporated under reduced pressure, and the residue was purified by silica gel column chromatography (ethyl acetate/hexane=30/70→80/20) to give the title compound (21.9 mg, yield from Reference Example 362%).

¹H-NMR (CDCl₃) δ: 2.80-2.87 (2H, m), 3.29-3.36 (2H, m), 7.48 (1H, d, J=8.2 Hz), 8.02 (1H, d, J=8.2 Hz), 8.19 (1H, s), melting point: 188-190° C. (recrystallized from hexane/ethyl acetate),
MS (ESI+): 174 (M+H),
Elemental analysis: for $C_{10}H_7NO_2$
Calcd. (%): C, 69.36; H, 4.07; N, 8.09
Found (%): C, 69.04; H, 4.02; N, 8.14.

REFERENCE EXAMPLE 8

2-Methyl-6,7-dihydro-8H-indeno[5,4-d][1,3]oxazol-8-one

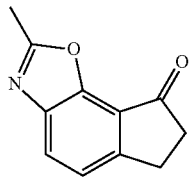

N-(4-Hydroxy-3-oxo-2,3-dihydro-1H-inden-5-yl)acetamide (469 mg, 2.29 mmol) and pyridinium p-toluenesulfonate (115 mg, 0.457 mmol) were heated under reflux in xylene (23 mL) for 2.5 hr. The solvent was evaporated under reduced pressure and the residue was purified by silica gel column chromatography (ethyl acetate/hexane=10/90→100/0) to give the title compound (363 mg, yield 85%).

$^1$H-NMR (CDCl$_3$) δ: 2.71 (3H, s), 2.78-2.85 (2H, m), 3.24-3.33 (2H, m), 7.38 (1H, d, J=8.0 Hz), 7.86 (1H, d, J=8.0 Hz),
melting point: 106-107° C. (recrystallized from hexane/ethyl acetate),
MS (ESI+): 188 (M+H),
Elemental analysis: for $C_{11}H_9NO_2 \cdot 0.1H_2O$
Calcd. (%): C, 69.90; H, 4.91; N, 7.41
Found (%): C, 70.09; H, 4.77; N, 7.20.

REFERENCE EXAMPLE 9

2-(4-Phenylbutyl)-6,7-dihydro-8H-indeno[5,4-d][1,3]oxazol-8-one

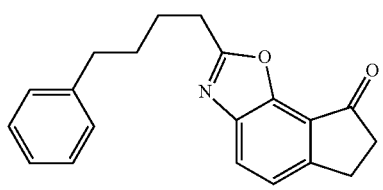 [SMILES: O=C1CCc2ccc3nc(CCCCc4ccccc4)oc3c21]

N-(4-Hydroxy-3-oxo-2,3-dihydro-1H-inden-5-yl)-5-phenylpentanamide (205 mg, 0.634 mmol) and pyridinium p-toluenesulfonate (31.9 mg, 0.127 mmol) were heated under reflux in xylene (6 mL) for 3 hr. The solvent was evaporated under reduced pressure and the residue was purified by silica gel column chromatography (ethyl acetate/hexane=10/90→40/60) to give the title compound (124 mg, yield 64%).

$^1$H-NMR (CDCl$_3$) δ: 1.70-1.84 (2H, m), 1.90-2.04 (2H, m), 2.68 (2H, t, J=7.6 Hz), 2.77-2.86 (2H, m), 3.03 (2H, t, J=7.6 Hz), 3.24-3.33 (2H, m), 7.12-7.22 (3H, m), 7.22-7.31 (2H, m), 7.38 (1H, d, J=8.2 Hz), 7.88 (1H, d, J=8.2 Hz),
MS (ESI+): 306 (M+H).

REFERENCE EXAMPLE 10

6-Nitro-1-indanone

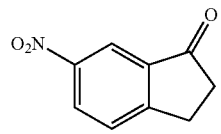 [SMILES: O=C1CCc2ccc([N+](=O)[O-])cc21]

1-Indanone (5.00 g, 37.8 mmol) was dissolved in sulfuric acid (40 mL), and thereto was added dropwise a solution of potassium nitrate (3.83 g, 37.8 mmol) in sulfuric acid (10 mL) under ice-cooling. The mixture was stirred for 1 hr under ice-cooling, ice was added to the reaction solution, and the mixture was stirred at room temperature overnight. The precipitated solid was collected by filtration, and purified by silica gel column chromatography (ethyl acetate/hexane=15/85→45/55) to give the title compound (4.01 g, yield 60%).

$^1$H-NMR (CDCl$_3$) δ: 2.78-2.90 (2H, m), 3.22-3.34 (2H, m), 7.67 (1H, d, J=8.5 Hz), 8.45 (1H, dd, J=8.5, 2.3 Hz), 8.57 (1H, d, J=2.3 Hz).

REFERENCE EXAMPLE 11

6-Amino-1-indanone

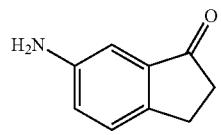

6-Nitro-1-indanone (10.0 g, 56.4 mmol) was dissolved in methanol (200 mL), a 10% palladium-carbon powder (500 mg) was added, and the mixture was stirred at room temperature for 14 hr under a hydrogen atmosphere. To the reaction solution were added dichloromethane and ethyl acetate to dissolve the precipitated crystals, and the catalyst was filtered off. The filtrate was concentrated under reduced pressure, and the residue was washed with methanol to give the title compound (6.71 g, yield 81%).

$^1$H-NMR (CDCl$_3$) δ: 2.62-2.72 (2H, m), 2.95-3.05 (2H, m), 3.79 (2H, brs), 6.92-6.97 (1H, m), 6.99 (1H, d, J=2.2 Hz), 7.25 (1H, d, J=8.0 Hz).

REFERENCE EXAMPLE 12

6-Amino-7-iodoindan-1-one

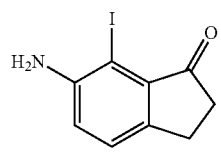 [SMILES: Nc1ccc2c(c1I)C(=O)CC2]

6-Amino-1-indanone (5.00 g, 34.0 mmol) was dissolved in a mixed solvent of methanol (200 mL) and water (50 mL), calcium carbonate (6.81 g, 68.0 mmol) and iodine(I) chloride (2.22 mL, 44.2 mmol) were added, and the mixture was stirred at room temperature for 2 hr. To the reaction solution was added saturated aqueous sodium thiosulfate solution, and the organic solvent was evaporated under reduced pressure. To the mixture was added saturated aqueous sodium hydrogencarbonate solution. The mixture was extracted with ethyl acetate and washed with saturated brine. The solvent was evaporated under reduced pressure. The residue was washed with methanol and ethyl acetate to give the title compound (7.95 g, yield 86%).

$^1$H-NMR (DMSO-$d_6$) δ: 2.56-2.66 (2H, m), 2.78-2.87 (2H, m), 5.48 (2H, s), 7.08 (1H, d, J=8.2 Hz), 7.25 (1H, d, J=8.2 Hz).

melting point: 183-186° C. (recrystallized from ethyl acetate),

MS (ESI+): 274 (M+H),

Elemental analysis: for $C_9H_8NOI$

Calcd. (%): C, 39.59; H, 2.95; N, 5.13

Found (%): C, 39.65; H, 2.87; N, 5.07.

REFERENCE EXAMPLE 13

2-Methyl-6,7-dihydro-8H-indeno[5,4-d][1,3]thiazol-8-one

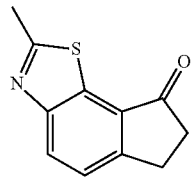

6-Amino-7-iodoindan-1-one (1.00 g, 3.66 mmol), thioacetamide (413 mg, 5.49 mmol), 1,1'-bis(diphenylphosphino)ferrocene (383 mg, 1.46 mmol), calcium oxide (411 mg, 7.32 mmol) and tris(dibenzylideneacetone)dipalladium(0) (335 mg, 0.37 mmol) were dissolved in N,N-dimethylformamide (12 mL), and the mixture was stirred at 60° C. for 1 hr. After allowing to cool to room temperature, water was added to the reaction solution. The mixture was extracted with ethyl acetate and washed with saturated brine. The solvent was evaporated under reduced pressure. The residue was purified by silica gel column chromatography (ethyl acetate/hexane=25/75→65/35), and then purified by silica gel column chromatography (NH, ethyl acetate/hexane=10/90→40/60) to give the title compound (340 mg, yield 46%).

$^1$H-NMR (CDCl$_3$) δ: 2.80-2.86 (2H, m), 2.90 (3H, s), 3.27-3.33 (2H, m), 7.54 (1H, d, J=8.2 Hz), 8.15 (1H, d, J=8.2 Hz), melting point: 163-165° C. (recrystallized from ethyl acetate),

MS (ESI+): 204 (M+H),

Elemental analysis: for $C_{11}H_9NOS$

Calcd. (%): C, 65.00; H, 4.46; N, 6.89

Found (%): C, 65.00; H, 4.29; N, 6.94.

REFERENCE EXAMPLE 14

(6,7-Dihydro-8H-indeno[5,4-d][1,3]oxazol-8-ylidene)acetonitrile

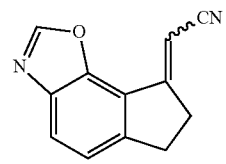 [SMILES: N#CC=C1CCc2ccc3ncoc3c21]

To a suspension of 60% sodium hydride (73.4 mg, 1.84 mmol) in tetrahydrofuran (8 mL) was added diethyl cyanomethylphosphonate (322 μL, 1.99 mmol) under ice-cooling, and the mixture was stirred for 15 min. Thereto was added a solution of 6,7-dihydro-8H-indeno[5,4-d][1,3]oxazol-8-one (265 mg, 1.53 mmol) in tetrahydrofuran (8 mL), and the mixture was further stirred for 30 min. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure, and the residue was purified by silica gel column chromatography (ethyl acetate/hexane=10/90→40/60) to give the title compound (220 mg, yield 73%).

$^1$H-NMR (CDCl$_3$) δ: 3.16-3.37 (4H, m), 6.07 (1H, t, J=2.5 Hz), 7.36 (1H, d, J=8.2 Hz), 7.81 (1H, d, J=8.2 Hz), 8.15 (1H, s), melting point: 166-168° C. (recrystallized from hexane/ethyl acetate),

MS (ESI+): 197 (M+H),

Elemental analysis: for $C_{12}H_8N_2O$

Calcd. (%): C, 73.46; H, 4.11; N, 14.28

Found (%): C, 73.44; H, 4.05; N, 14.49.

REFERENCE EXAMPLE 15

(2-Methyl-6,7-dihydro-8H-indeno[5,4-d][1,3]oxazol-8-ylidene)acetonitrile

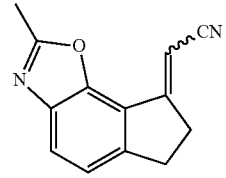 [SMILES: Cc1nc2ccc3c(c2o1)C(=CC#N)CC3]

To a suspension of 60% sodium hydride (90.0 mg, 2.24 mmol) in tetrahydrofuran (9 mL) was added diethyl cyanomethylphosphonate (393 μL, 2.43 mmol) under ice-cooling, and the mixture was stirred for 15 min. Thereto was added a solution of 2-methyl-6,7-dihydro-8H-indeno[5,4-d][1,3]oxazol-8-one (350 mg, 1.87 mmol) in tetrahydrofuran (9 mL), and the mixture was further stirred for 1 hr. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure, and the residue was purified by silica gel column chromatography (ethyl acetate/hexane=10/90→40/60) to give the title compound (300 mg, yield 76%).

$^1$H-NMR (CDCl$_3$) δ: 2.70 (3H, s), 3.15-3.31 (4H, m), 6.04 (1H, t, J=2.6 Hz), 7.28 (1H, d, J=8.0 Hz), 7.67 (1H, d, J=8.0 Hz), melting point: 180-182° C. (recrystallized from ethyl acetate),

MS (ESI+): 211 (M+H),

Elemental analysis: for C$_{13}$H$_{10}$N$_2$O

Calcd. (%): C, 74.27; H, 4.79; N, 13.33

Found (%): C, 74.22; H, 4.75; N, 13.16.

REFERENCE EXAMPLE 16

[2-(4-Phenylbutyl)-6,7-dihydro-8H-indeno[5,4-d][1,3]oxazol-8-ylidene]acetonitrile

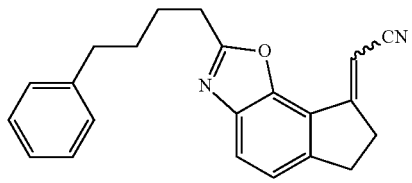 [SMILES: N#CC=C1CCc2ccc3nc(CCCCc4ccccc4)oc3c21]

To a suspension of 60% sodium hydride (19.5 mg, 0.487 mmol) in tetrahydrofuran (2 mL) was added diethyl cyanomethylphosphonate (85.4 μL, 0.528 mmol) under ice-cooling, and the mixture was stirred for 15 min. Thereto was added a solution of 2-(4-phenylbutyl)-6,7-dihydro-8H-indeno[5,4-d][1,3]oxazol-8-one (124 mg, 0.406 mmol) in tetrahydrofuran (2 mL), and the mixture was further stirred for 30 min. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure, and the residue was purified by silica gel column chromatography (ethyl acetate/hexane=10/90→40/60) to give the title compound (125 mg, yield 94%).

$^1$H-NMR (CDCl$_3$) δ: 1.71-1.85 (2H, m), 1.88-2.02 (2H, m), 2.70 (2H, t, J=7.4 Hz), 3.00 (2H, t, J=7.4 Hz), 3.15-3.31 (4H, m), 5.99 (1H, t, J=2.6 Hz), 7.14-7.23 (3H, m), 7.23-7.33 (3H, m), 7.68 (1H, d, J=8.2 Hz),

MS (ESI+): 329 (M+H).

REFERENCE EXAMPLE 17

(2-Methyl-6,7-dihydro-8H-indeno[5,4-d][1,3]thiazol-8-ylidene)acetonitrile

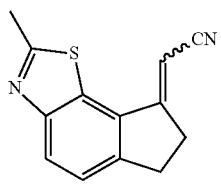 [SMILES: Cc1nc2ccc3c(c2s1)C(=CC#N)CC3]

To a suspension of diethyl cyanomethylphosphonate (393 mg, 2.22 mmol) in tetrahydrofuran (6 mL) was added 65% sodium hydride (66.0 mg, 1.79 mmol) under ice-cooling, and the mixture was stirred at room temperature for 30 min. Thereto was added a solution of 2-methyl-6,7-dihydro-8H-indeno[5,4-d][1,3]thiazol-8-one (300 mg, 1.48 mmol) in tetrahydrofuran (6 mL), and the mixture was stirred at room temperature for 2 hr. To the mixture were added diethyl cyanomethylphosphonate (131 mg, 0.74 mmol) and 65% sodium hydride (16.0 mg, 0.43 mmol), and the mixture was further stirred at room temperature for 30 min. To the reaction mixture was added saturated aqueous sodium hydrogencarbonate solution, and the mixture was extracted with ethyl acetate. The extract was washed with saturated brine and dried over anhydrous sodium sulfate. The solvent was evaporated under reduced pressure, and the residue was purified by silica gel column chromatography (ethyl acetate) to give the title compound (181 mg, yield 54%).

$^1$H-NMR (CDCl$_3$) δ: 2.91 (3H, s), 3.27 (4H, s), 5.60-5.63 (1H, m), 7.46 (1H, d, J=8.2 Hz), 8.01 (1H, d, J=8.2 Hz), melting point: 194-195° C. (recrystallized from hexane/ethyl acetate),

MS (ESI+): 227 (M+H),

Elemental analysis: for C$_{13}$H$_{10}$N$_2$S

Calcd. (%): C, 69.00; H, 4.45; N, 12.38

Found (%): C, 68.76; H, 4.19; N, 12.40.

REFERENCE EXAMPLE 18

2-(6,7-Dihydro-8H-indeno[5,4-d][1,3]oxazol-8-ylidene)ethanamine

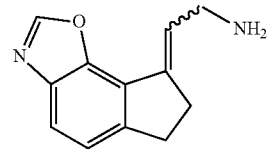 [SMILES: NCC=C1CCc2ccc3ncoc3c21]

To a solution of (6,7-dihydro-8H-indeno[5,4-d][1,3]oxazol-8-ylidene)acetonitrile (210 mg, 1.07 mmol) in ethanol (8 mL) were added Raney cobalt (2 g) and 2N ammonia/ethanol solution (4 mL), and the mixture was stirred at room temperature for 5 hr under a hydrogen atmosphere. The catalyst was filtered off using celite, and the filtrate was concentrated under reduced pressure. The residue was purified by silica gel column chromatography (NH, ethyl acetate/hexane=50/50→100/0) to give the title compound (60.2 mg, yield 28%).

$^1$H-NMR (CDCl$_3$) δ: 2.83-2.91 (2H, m), 3.14-3.21 (2H, m), 3.55 (2H, d, J=7.1 Hz), 6.38-6.47 (1H, m), 7.24 (1H, d, J=8.2 Hz), 7.59 (1H, d, J=8.2 Hz), 8.10 (1H, s), hidden (2H).

REFERENCE EXAMPLE 19

2-(2-Methyl-6,7-dihydro-8H-indeno[5,4-d][1,3]oxazol-8-ylidene)ethanamine

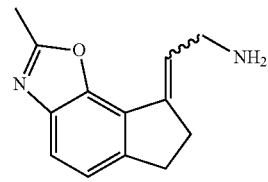 [SMILES: Cc1nc2ccc3c(c2o1)C(=CCN)CC3]

To a solution of (2-methyl-6,7-dihydro-8H-indeno[5,4-d][1,3]oxazol-8-ylidene)acetonitrile (290 mg, 1.38 mmol) in ethanol (8 mL) were added Raney cobalt (3 g) and 2N ammonia/ethanol solution (4 mL), and the mixture was stirred at room temperature for 3 hr under a hydrogen atmosphere. The catalyst was filtered off using celite, and the filtrate was concentrated under reduced pressure to give the title compound. The obtained title compound was used for the reaction of Examples 3 and 5 without further purification.

$^1$H-NMR (CDCl$_3$) δ: 2.65 (3H, s), 2.77-2.89 (2H, m), 3.08-3.17 (2H, m), 3.52 (2H, d, J=6.9 Hz), 6.35-6.43 (1H, m), 7.15 (1H, d, J=8.0 Hz), 7.44 (1H, d, J=8.0 Hz), hidden (2H).

REFERENCE EXAMPLE 20

2-[2-(4-Phenylbutyl)-6,7-dihydro-8H-indeno[5,4-d][1,3]oxazol-8-ylidene]ethanamine

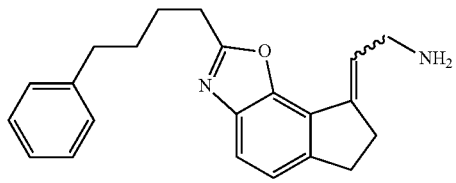 [SMILES: NCC=C1CCc2ccc3nc(CCCCc4ccccc4)oc3c21]

To a solution of [2-(4-phenylbutyl)-6,7-dihydro-8H-indeno[5,4-d][1,3]oxazol-8-ylidene]acetonitrile (125 mg, 0.382 mmol) in ethanol (2.4 mL) were added Raney cobalt (1.2 g) and 2N ammonia/ethanol solution (1.2 mL), and the mixture was stirred at room temperature for 3 hr under a hydrogen atmosphere. The catalyst was filtered off using celite, and the filtrate was concentrated under reduced pressure to give the title compound. The obtained title compound was used for the reaction of Examples 6 and 7 without further purification.

$^1$H-NMR (CDCl$_3$) δ: 1.73-1.85 (2H, m), 1.87-2.01 (2H, m), 2.70 (2H, t, J=7.6 Hz), 2.80-2.90 (2H, m), 2.98 (2H, t, J=7.6 Hz), 3.11-3.19 (2H, m), 3.54 (2H, d, J=7.1 Hz), 6.33-6.42 (1H, m), 7.14-7.22 (4H, m), 7.22-7.32 (2H, m), 7.47 (1H, d, J=8.0 Hz), hidden (2H).

REFERENCE EXAMPLE 21

2-(2-Methyl-6,7-dihydro-8H-indeno[5,4-d][1,3]thiazol-8-ylidene)ethanamine

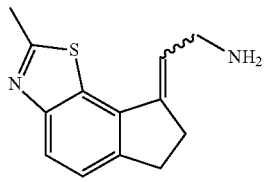 [SMILES: Cc1nc2ccc3c(c2s1)C(=CCN)CC3]

(2-Methyl-6,7-dihydro-8H-indeno[5,4-d][1,3]thiazol-8-ylidene)acetonitrile (170 mg, 0.75 mmol) was dissolved in 2N ammonia/methanol solution (30 mL), Raney cobalt (1.7 g) was added, and the mixture was stirred at room temperature for 1 hr under a hydrogen atmosphere. The catalyst was filtered off using celite, and the filtrate was concentrated under reduced pressure to give the title compound. The obtained title compound was used for the reaction of Example 8 without further purification.

$^1$H-NMR (CDCl$_3$) δ: 2.79-2.96 (5H, m), 3.08-3.21 (2H, m), 4.13 (2H, d, J=6.6 Hz), 6.01-6.12 (1H, m), 7.33 (1H, d, J=8.2 Hz), 7.80 (1H, d, J=8.2 Hz), hidden (2H).

REFERENCE EXAMPLE 22

4-Bromo-7-methoxy-6-nitroindan-1-one

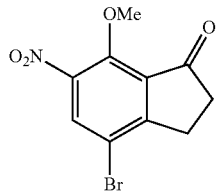 [SMILES: COc1c([N+](=O)[O-])cc(Br)c2c1C(=O)CC2]

4-Bromo-7-hydroxy-6-nitroindan-1-one (8.07 g, 29.7 mmol) and 1,8-diazabicyclo[5.4.0]undec-7-ene (5.33 mL, 35.6 mmol) were dissolved in N,N-dimethylformamide (150 mL), iodomethane (18.5 mL, 297 mmol) was added, and the mixture was stirred at room temperature for 40 hr. To the reaction solution was added saturated aqueous sodium hydrogencarbonate solution. The mixture was extracted with diethyl ether, washed with saturated brine and dried over anhydrous sodium sulfate. The solvent was evaporated under reduced pressure, and the residue was purified by silica gel column chromatography (ethyl acetate/hexane=30/70→60/40) to give the title compound (6.70 g, yield 79%).

$^1$H-NMR (CDCl$_3$) δ: 2.78-2.86 (2H, m), 3.07-3.15 (2H, m), 4.13 (3H, s), 8.16 (1H, s), melting point: 138-139° C. (recrystallized from hexane/ethyl acetate),

MS (ESI+): 286 (M+H),

Elemental analysis: for C$_{10}$H$_8$NO$_4$Br

Calcd. (%): C, 41.98; H, 2.82; N, 4.90

Found (%): C, 41.98; H, 2.76; N, 4.82.

REFERENCE EXAMPLE 23

(4-Bromo-7-methoxy-6-nitro-2,3-dihydro-1H-inden-1-ylidene)acetonitrile

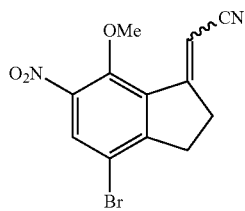 [SMILES: COc1c([N+](=O)[O-])cc(Br)c2c1C(=CC#N)CC2]

To a suspension of 60% sodium hydride (1.03 g, 25.6 mmol) in tetrahydrofuran (100 mL) was added diethyl cyanomethylphosphonate (4.52 mL, 28.0 mmol) under ice-cooling, and the mixture was stirred for 15 min. Thereto was added a solution of 4-bromo-7-methoxy-6-nitroindan-1-one (6.67 g, 23.3 mmol) in tetrahydrofuran (50 mL), and the mixture was further stirred for 30 min. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure, and the residue was purified by silica gel column chromatography (ethyl acetate/hexane=10/90→40/60) to give the title compound (5.54 g, yield 77%).

$^1$H-NMR (CDCl$_3$) δ: 3.09-3.25 (4H, m), 3.94 (3H, s), 6.27 (1H, t, J=2.6 Hz), 8.03 (1H, s), melting point: 156-158° C. (recrystallized from hexane/ethyl acetate), Elemental analysis: for C$_{12}$H$_9$N$_2$O$_3$Br
Calcd. (%): C, 46.63; H, 2.93; N, 9.06
Found (%): C, 46.66; H, 2.86; N, 9.09.

REFERENCE EXAMPLE 24

(6-Amino-7-methoxy-2,3-dihydro-1H-inden-1-ylidene)acetonitrile

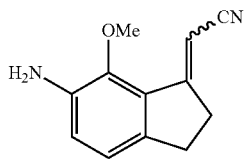 [SMILES: COc1c(N)ccc2c1C(=CC#N)CC2]

(4-Bromo-7-methoxy-6-nitro-2,3-dihydro-1H-inden-1-ylidene)acetonitrile (47.0 mg, 0.152 mmol) and triethylamine (22.3 μL, 0.160 mmol) were dissolved in ethyl acetate (1.5 mL), a 10% palladium-carbon powder (10 mg) was added, and the mixture was stirred at room temperature for 1.5 hr under a hydrogen atmosphere. The catalyst was filtered off using celite, and the filtrate was concentrated under reduced pressure to give the title compound (30.4 mg, yield 100%).

$^1$H-NMR (CDCl$_3$) δ: 2.94-3.01 (2H, m), 3.04-3.11 (2H, m), 3.76 (3H, s), 3.78 (2H, brs), 6.11 (1H, t, J=2.6 Hz), 6.81 (1H, d, J=8.0 Hz), 6.91 (1H, d, J=8.0 Hz), melting point: 140-142° C. (recrystallized from hexane/ethyl acetate), MS (ESI+): 201 (M+H),
Elemental analysis: for C$_{12}$H$_{12}$N$_2$O
Calcd. (%): C, 71.98; H, 6.04; N, 13.99
Found (%): C, 71.60; H, 6.14; N, 13.94.

REFERENCE EXAMPLE 25

3-(2-Aminoethylidene)-4-methoxyindan-5-amine

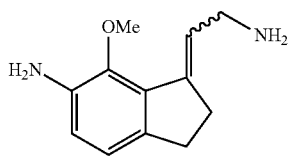 [SMILES: COc1c(N)ccc2c1C(=CCN)CC2]

To a solution of (6-amino-7-methoxy-2,3-dihydro-1H-inden-1-ylidene)acetonitrile (15.2 mg, 0.076 mmol) in ethanol (0.5 mL) were added Raney cobalt (150 mg) and 2N ammonia/ethanol solution (0.5 mL), and the mixture was stirred at room temperature for 2 hr under a hydrogen atmosphere. The catalyst was filtered off using celite, and the filtrate was concentrated under reduced pressure to give the title compound (15.3 mg, yield 99%).

$^1$H-NMR (CDCl$_3$) δ: 2.67-2.75 (2H, m), 2.84-2.94 (2H, m), 3.48 (2H, d, J=6.6 Hz), 3.72 (2H, brs), 3.77 (3H, s), 6.34-6.44 (1H, m), 6.62 (1H, d, J=7.7 Hz), 6.81 (1H, d, J=7.7 Hz), hidden (2H).

REFERENCE EXAMPLE 26

N-[2-(6-Amino-7-methoxy-2,3-dihydro-1H-inden-1-ylidene)ethyl]acetamide

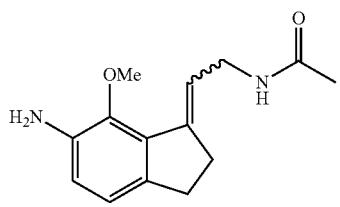 [SMILES: COc1c(N)ccc2c1C(=CCNC(C)=O)CC2]

3-(2-Aminoethylidene)-4-methoxyindan-5-amine (15.3 mg, 0.076 mmol) and triethylamine (21.2 μL, 0.152 mmol) were dissolved in tetrahydrofuran (0.9 mL), a solution of acetic anhydride (7.18 μL, 0.076 mmol) in tetrahydrofuran (0.1 mL) was added under ice-cooling, and the mixture was stirred for 15 min. To the reaction solution was added saturated aqueous sodium hydrogencarbonate solution. The mixture was extracted with ethyl acetate and washed with saturated brine. The solvent was evaporated under reduced pressure, and the residue was purified by silica gel column chromatography (ethyl acetate/methanol=100/0→90/10) to give the title compound (16.2 mg, yield 87%).

$^1$H-NMR (CDCl$_3$) δ: 2.01 (3H, s), 2.70-2.80 (2H, m), 2.85-2.96 (2H, m), 3.75 (3H, s), 4.01-4.09 (2H, m), 5.52 (1H, brs), 6.25-6.33 (1H, m), 6.65 (1H, d, J=8.0 Hz), 6.82 (1H, d, J=8.0 Hz), hidden (2H).

melting point: 105-107° C. (recrystallized from hexane/ethyl acetate),

MS (ESI+): 247 (M+H),
Elemental analysis: for C$_{14}$H$_{18}$N$_2$O$_2$
Calcd. (%): C, 68.27; H, 7.37; N, 11.37
Found (%): C, 67.93; H, 7.25; N, 11.10.

REFERENCE EXAMPLE 27

N-[2-(6-Amino-7-methoxy-2,3-dihydro-1H-inden-1-yl)ethyl]acetamide

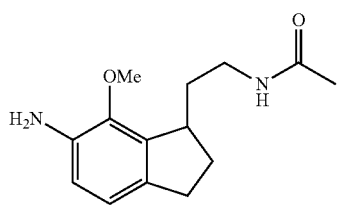 [SMILES: COc1c(N)ccc2c1C(CCNC(C)=O)CC2]

N-[2-(6-Amino-7-methoxy-2,3-dihydro-1H-inden-1-ylidene)ethyl]acetamide (2.62 g, 10.7 mmol) was dissolved in methanol (50 mL), a 10% palladium-carbon powder (500 mg) was added, and the mixture was stirred at room temperature for 5 hr under a hydrogen atmosphere. The catalyst was filtered off using celite, and the filtrate was concentrated under reduced pressure to give the title compound (2.56 g, yield 96%).

¹H-NMR (CDCl₃) δ: 1.68-1.93 (3H, m), 1.95 (3H, s), 2.16-2.31 (1H, m), 2.65-2.79 (1H, m), 2.81-2.96 (1H, m), 3.09-3.24 (1H, m), 3.28-3.50 (2H, m), 3.79 (3H, s), 3.91 (2H, brs), 5.71 (1H, brs), 6.60 (1H, d, J=8.0 Hz), 6.78 (1H, d, J=8.0 Hz), melting point: 130-132° C. (recrystallized from hexane/ethyl acetate),

MS (ESI+): 249 (M+H),

Elemental analysis: for $C_{14}H_{20}N_2O_2$

Calcd. (%): C, 67.71; H, 8.12; N, 11.28

Found (%): C, 67.56; H, 8.01; N, 11.27.

REFERENCE EXAMPLE 28

N-[2-(6-Amino-7-hydroxy-2,3-dihydro-1H-inden-1-yl)ethyl]acetamide hydrochloride

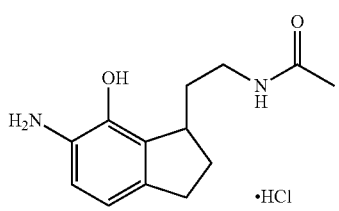 [SMILES: CC(=O)NCCC1CCc2ccc(N)c(O)c21 ; Cl]

To a solution of N-[2-(6-amino-7-methoxy-2,3-dihydro-1H-inden-1-yl)ethyl]acetamide (2.56 g, 10.3 mmol) in dichloromethane (80 mL) was added a solution of boron tribromide in dichloromethane (1M, 22.7 mL, 22.7 mmol) under ice-cooling, and the mixture was stirred at room temperature for 1.5 hr. To the reaction solution was added water, and the mixture was diluted with ethyl acetate, washed with saturated aqueous sodium hydrogencarbonate solution and saturated brine, and dried over anhydrous sodium sulfate. The solvent was evaporated under reduced pressure. The residue was dissolved in dichloromethane (80 mL), a solution of boron tribromide in dichloromethane (1M, 22.7 mL, 22.7 mmol) was added under ice-cooling, and the mixture was stirred at room temperature for 1.5 hr. To the reaction solution was added water, and the mixture was diluted with ethyl acetate, washed with saturated aqueous sodium hydrogencarbonate solution and saturated brine, and dried over anhydrous sodium sulfate. The solvent was evaporated under reduced pressure. The residue was dissolved in ethyl acetate, and converted to hydrochloride with 4N hydrochloric acid/ethyl acetate solution. The solvent was evaporated under reduced pressure to give the title compound (2.51 g, yield 90%).

¹H-NMR (DMSO-d₆) δ: 1.31-1.46 (1H, m), 1.68-1.86 (3H, m), 1.80 (3H, s), 1.99-2.14 (1H, m), 2.64-2.77 (1H, m), 2.80-2.95 (1H, m), 3.04-3.13 (1H, m), 3.37-3.50 (1H, m), 6.74 (1H, d, J=8.0 Hz), 7.13 (1H, d, J=8.0 Hz), 8.09 (1H, brs), 9.87 (3H, brs), 10.14 (1H, brs),

MS (ESI+): 235 (M+H).

REFERENCE EXAMPLE 29

N-{3-[2-(Acetylamino)ethyl]-4-hydroxy-2,3-dihydro-1H-inden-5-yl}propanamide

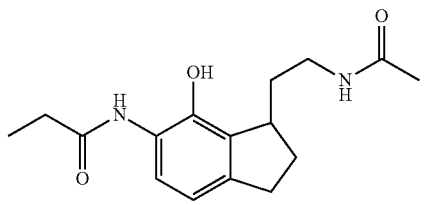 [SMILES: CCC(=O)Nc1ccc2c(c1O)C(CCNC(C)=O)CC2]

N-[2-(6-Amino-7-hydroxy-2,3-dihydro-1H-inden-1-yl)ethyl]acetamide hydrochloride (100 mg, 0.369 mmol) was dissolved in pyridine (4 mL), propionic anhydride (52.1 μL, 0.406 mmol) was added under ice-cooling, and the mixture was stirred for 15 min. Water was added to the reaction solution, and the solvent was evaporated under reduced pressure. The residue was purified by silica gel column chromatography (ethyl acetate/methanol=100/0→90/10) to give the title compound (94.5 mg, yield 88%).

¹H-NMR (CDCl₃) δ: 1.28 (3H, t, J=7.4 Hz), 1.73-1.87 (3H, m), 2.02 (3H, s), 2.16-2.31 (1H, m), 2.48 (2H, q, J=7.4 Hz), 2.67-2.79 (1H, m), 2.88-3.03 (1H, m), 3.15-3.29 (1H, m), 3.29-3.43 (2H, m), 6.29 (1H, brs), 6.71 (1H, d, J=8.0 Hz), 7.13 (1H, d, J=8.0 Hz), 7.82 (1H, brs), 9.77 (1H, brs),

MS (ESI+): 291 (M+H).

REFERENCE EXAMPLE 30

N-{3-[2-(Acetylamino)ethyl]-4-hydroxy-2,3-dihydro-1H-inden-5-yl}-2-(benzyloxy)acetamide

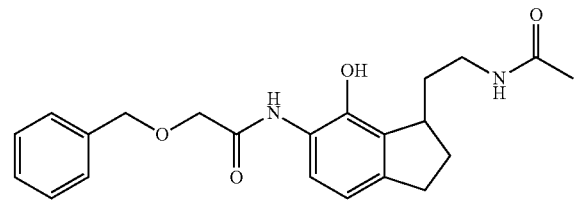

N-[2-(6-Amino-7-hydroxy-2,3-dihydro-1H-inden-1-yl)ethyl]acetamide hydrochloride (251 mg, 0.928 mmol) was dissolved in pyridine (10 mL), (benzyloxy)acetyl chloride (160 μL, 1.01 mmol) was added under ice-cooling, and the mixture was stirred for 15 min. Water was added to the reaction solution, and the solvent was evaporated under reduced pressure. The residue was purified by silica gel column chromatography (ethyl acetate/hexane=80/20→100/0) to give the title compound (285 mg, yield 80%).

¹H-NMR (CDCl₃) δ: 1.76-1.89 (3H, m), 2.00 (3H, s), 2.15-2.33 (1H, m), 2.66-2.82 (1H, m), 2.89-3.06 (1H, m), 3.10-3.30 (1H, m), 3.33-3.48 (2H, m), 4.14 (2H, s), 4.69 (2H, s), 6.17 (1H, brs), 6.73 (1H, d, J=7.9 Hz), 7.03 (1H, d, J=7.9 Hz), 7.33-7.46 (5H, m), 8.65 (1H, s), 9.71 (1H, s),

MS (ESI+): 383 (M+H).

REFERENCE EXAMPLE 31

N-{3-[2-(Acetylamino)ethyl]-4-hydroxy-2,3-dihydro-1H-inden-5-yl}-2-methylpropanamide

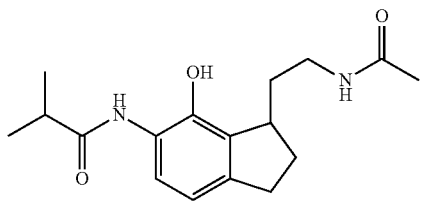

N-[2-(6-Amino-7-hydroxy-2,3-dihydro-1H-inden-1-yl)ethyl]acetamide hydrochloride (100 mg, 0.369 mmol) was dissolved in pyridine (4 mL), isobutyryl chloride (42.5 μL, 0.406 mmol) was added under ice-cooling, and the mixture was stirred for 3 hr. Water was added to the reaction solution, and the solvent was evaporated under reduced pressure. The residue was purified by silica gel column chromatography (ethyl acetate/methanol=100/0→95/5) to give the title compound (118 mg, yield 100%).

$^1$H-NMR (CDCl$_3$) δ: 1.08-1.34 (6H, m), 1.61-1.88 (2H, m), 1.90-2.09 (4H, m), 2.10-2.35 (1H, m), 2.52-2.78 (2H, m), 2.83-3.24 (2H, m), 3.26-3.58 (2H, m), 6.58 (1H, s), 6.68 (1H, d, J=8.0 Hz), 7.12 (1H, d, J=8.0 Hz), 8.33 (1H, brs), hidden (1H),

MS (ESI+): 305 (M+H).

REFERENCE EXAMPLE 32

N-{3-[2-(Acetylamino)ethyl]-4-hydroxy-2,3-dihydro-1H-inden-5-yl}-2,2,2-trifluoroacetamide

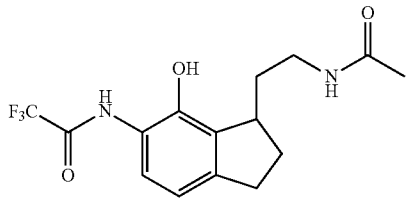 [SMILES: CC(=O)NCCC1CCc2ccc(NC(=O)C(F)(F)F)c(O)c21]

N-[2-(6-Amino-7-hydroxy-2,3-dihydro-1H-inden-1-yl)ethyl]acetamide hydrochloride (100 mg, 0.369 mmol) was dissolved in pyridine (4 mL), trifluoroacetic anhydride (56.1 μL, 0.406 mmol) was added under ice-cooling, and the mixture was stirred for 15 min. Water was added to the reaction solution, and the solvent was evaporated under reduced pressure. The residue was purified by silica gel column chromatography (ethyl acetate/hexane=30/70→80/20) to give the title compound (27.8 mg, yield 23%).

$^1$H-NMR (CDCl$_3$) δ: 1.66-1.92 (3H, m), 2.13 (3H, s), 2.17-2.32 (1H, m), 2.68-2.80 (1H, m), 2.87-3.03 (2H, m), 3.31-3.42 (1H, m), 3.62-3.78 (1H, m), 6.10 (1H, brs), 6.77 (1H, d, J=8.2 Hz), 8.07 (1H, d, J=8.2 Hz), 8.80 (1H, s), 10.83 (1H, s),

MS (ESI+): 331 (M+H).

REFERENCE EXAMPLE 33

N-{3-[2-(Acetylamino)ethyl]-4-hydroxy-2,3-dihydro-1H-inden-5-yl}-5-(benzyloxy)pentanamide

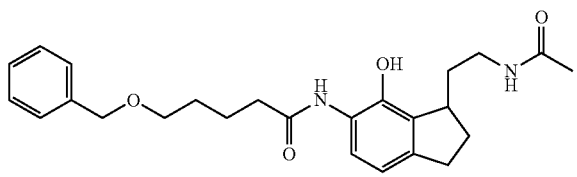 [SMILES: CC(=O)NCCC1CCc2ccc(NC(=O)CCCCOCc3ccccc3)c(O)c21]

N-[2-(6-Amino-7-hydroxy-2,3-dihydro-1H-inden-1-yl)ethyl]acetamide hydrochloride (162 mg, 0.600 mmol) was dissolved in pyridine (10 mL), 5-(benzyloxy)pentanoyl chloride (150 mg, 0.662 mmol) was added under ice-cooling, and the mixture was stirred for 15 min. The solvent was evaporated under reduced pressure, and the residue was purified by silica gel column chromatography (ethyl acetate/hexane=80/20→100/0) to give the title compound (105 mg, yield 41%).

$^1$H-NMR (CDCl$_3$) δ: 1.70-1.95 (7H, m), 1.99 (3H, s), 2.13-2.30 (1H, m), 2.50 (2H, t, J=7.1 Hz), 2.64-2.76 (1H, m), 2.86-3.02 (1H, m), 3.07-3.22 (1H, m), 3.30-3.47 (2H, m), 3.58 (2H, t, J=5.8 Hz), 4.51 (2H, s), 6.29 (1H, brs), 6.61-6.66 (1H, m), 6.68-6.73 (1H, m), 7.26-7.38 (5H, m), 8.02-8.17 (1H, m), 9.80 (1H, s),

MS (ESI+): 425 (M+H).

REFERENCE EXAMPLE 34

4-(Benzyloxy)pentanoic acid

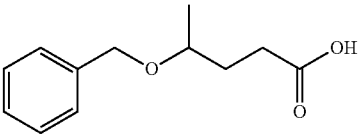

To a solution of 4-(benzyloxy)pentan-1-ol (350 mg, 1.80 mmol) in acetone (20 mL) was added Jones reagent (1.9M, 1.9 mL, 3.6 mmol) under ice-cooling, and the mixture was stirred for 30 min. Sodium sulfite was added to the reaction solution, and the solvent was evaporated under reduced pressure. The residual aqueous solution was washed with ethyl acetate, acidified with 1N hydrochloric acid, and extracted with ethyl acetate. The extract was dried over anhydrous sodium sulfate, and the solvent was evaporated under reduced pressure. The residue was purified by silica gel column chromatography (ethyl acetate/hexane=20/80-440/60) to give the title compound (236 mg, yield 63%).

¹H-NMR (CDCl₃) δ: 1.23 (3H, d, J=6.3 Hz), 1.80-1.91 (2H, m), 2.48 (2H, t, J=7.4 Hz), 3.51-3.65 (1H, m), 4.43 (1H, d, J=11.6 Hz), 4.59 (1H, d, J=11.6 Hz), 7.23-7.37 (5H, m), hidden (1H).

REFERENCE EXAMPLE 35

N-{3-[2-(Acetylamino)ethyl]-4-hydroxy-2,3-dihydro-1H-inden-5-yl}-4-(benzyloxy)pentanamide

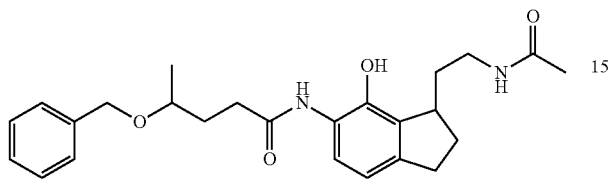

4-(Benzyloxy)pentanoic acid (230 mg, 1.10 mmol) was dissolved in tetrahydrofuran (10 mL), oxalyl chloride (90 μL, 1.05 mmol) and dimethylformamide (10 μL) were added under ice-cooling, and the mixture was stirred for 30 min. The solvent was evaporated under reduced pressure, and the residue was diluted with dichloromethane (1 mL). This was added to a solution of N-[2-(6-amino-7-hydroxy-2,3-dihydro-1H-inden-1-yl)ethyl]acetamide hydrochloride (244 mg, 0.903 mmol) in pyridine (10 mL) under ice-cooling, and the mixture was stirred at room temperature for 15 min. The solvent was evaporated under reduced pressure, and the residue was purified by silica gel column chromatography (ethyl acetate/hexane=80/20→100/0) to give the title compound (220 mg, yield 57%).

¹H-NMR (CDCl₃) δ: 1.27 (3H, d, J=6.0 Hz), 1.72-2.08 (8H, m), 2.13-2.30 (1H, m), 2.55 (2H, t, J=6.9 Hz), 2.64-2.76 (1H, m), 2.85-3.01 (1H, m), 3.04-3.22 (1H, m), 3.29-3.50 (2H, m), 3.61-3.75 (1H, m), 4.41 (1H, dd, J=11.3, 1.8 Hz), 4.66 (1H, d, J=11.3 Hz), 6.25 (1H, brs), 6.52-6.66 (2H, m), 7.22-7.38 (5H, m), 8.21 (1H, brs), 9.72 (1H, s),
MS (ESI+): 425 (M+H).

REFERENCE EXAMPLE 36

N-{3-[2-(Acetylamino)ethyl]-4-hydroxy-2,3-dihydro-1H-inden-5-yl}cyclopropanecarboxamide

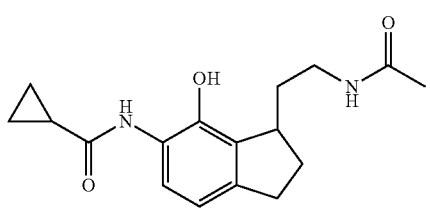 [SMILES: CC(=O)NCCC1CCc2ccc(NC(=O)C3CC3)c(O)c21]

N-[2-(6-Amino-7-hydroxy-2,3-dihydro-1H-inden-1-yl)ethyl]acetamide hydrochloride (100 mg, 0.369 mmol) was dissolved in pyridine (4 mL), cyclopropylcarbonyl chloride (36.8 μL, 0.406 mmol) was added under ice-cooling, and the mixture was stirred for 3 hr. Water was added to the reaction solution, and the solvent was evaporated under reduced pressure. The residue was purified by silica gel column chromatography (ethyl acetate/methanol=100/0→95/5) to give the title compound (119 mg, yield 100%).

¹H-NMR (CDCl₃) δ: 0.77-0.94 (2H, m), 0.97-1.13 (2H, m), 1.20-1.33 (1H, m), 1.52-1.85 (2H, m), 1.90-2.10 (4H, m), 2.10-2.32 (1H, m), 2.63-2.78 (1H, m), 2.84-3.01 (1H, m), 3.02-3.19 (1H, m), 3.20-3.54 (2H, m), 6.58 (1H, s), 6.67 (1H, d, J=8.0 Hz), 7.00 (1H, d, J=8.0 Hz), 8.44-8.90 (1H, m), hidden (1H),
MS (ESI+): 303 (M+H).

REFERENCE EXAMPLE 37

N-{3-[2-(Acetylamino)ethyl]-4-hydroxy-2,3-dihydro-1H-inden-5-yl}benzamide

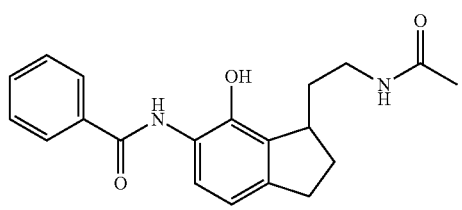 [SMILES: CC(=O)NCCC1CCc2ccc(NC(=O)c3ccccc3)c(O)c21]

N-[2-(6-Amino-7-hydroxy-2,3-dihydro-1H-inden-1-yl)ethyl]acetamide hydrochloride (100 mg, 0.369 mmol) was dissolved in pyridine (4 mL), benzoyl chloride (47.1 μL, 0.406 mmol) was added under ice-cooling, and the mixture was stirred for 15 min. Water was added to the reaction solution, and the solvent was evaporated under reduced pressure. The residue was purified by silica gel column chromatography (ethyl acetate/hexane=80/20→100/0) to give the title compound (111 mg, yield 89%).

¹H-NMR (CDCl₃) δ: 1.72-1.93 (3H, m), 2.05 (3H, s), 2.17-2.36 (1H, m), 2.68-2.84 (1H, m), 2.91-3.07 (1H, m), 3.19-3.47 (3H, m), 6.14-6.32 (1H, m), 6.79 (1H, d, J=7.9 Hz), 7.45-7.62 (4H, m), 7.93 (2H, d, J=8.1 Hz), 8.49 (1H, brs), 9.97 (1H, brs),
MS (ESI+): 339 (M+H).

REFERENCE EXAMPLE 38

N-{3-[2-(Acetylamino)ethyl]-4-hydroxy-2,3-dihydro-1H-inden-5-yl}-2-phenylacetamide

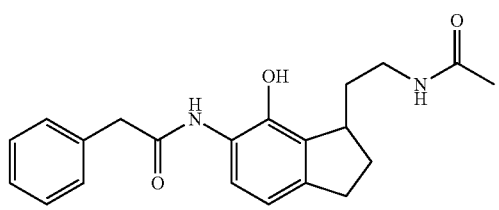 [SMILES: CC(=O)NCCC1CCc2ccc(NC(=O)Cc3ccccc3)c(O)c21]

N-[2-(6-Amino-7-hydroxy-2,3-dihydro-1H-inden-1-yl)ethyl]acetamide hydrochloride (100 mg, 0.369 mmol) was dissolved in pyridine (4 mL), phenylacetyl chloride (53.5 μL, 0.406 mmol) was added under ice-cooling, and the mixture was stirred for 15 min. Water was added to the reaction solution, and the solvent was evaporated under reduced pressure. The residue was purified by silica gel column chromatography (ethyl acetate/hexane=80/20→100/0) to give the title compound (31.0 mg, yield 24%).

¹H-NMR (CDCl₃) δ: 1.71-1.85 (3H, m), 1.99 (3H, s), 2.12-2.27 (1H, m), 2.63-2.76 (1H, m), 2.84-3.00 (1H, m), 3.11-3.25 (1H, m), 3.29-3.41 (2H, m), 3.78 (2H, s), 6.16 (1H, brs), 6.65 (1H, d, J=8.0 Hz), 6.90 (1H, d, J=8.0 Hz), 7.28-7.44 (5H, m), 7.51 (1H, brs), 9.58 (1H, brs),
MS (ESI+): 353 (M+H).

REFERENCE EXAMPLE 39

N-{3-[2-(Acetylamino)ethyl]-4-hydroxy-2,3-dihydro-1H-inden-5-yl}-3-phenylpropanamide

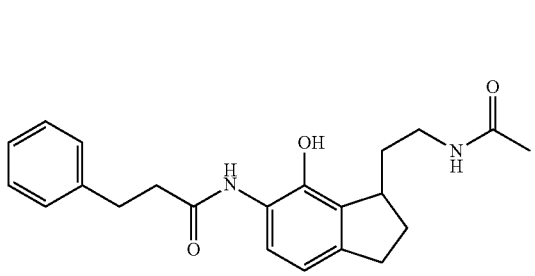 [SMILES: CC(=O)NCCC1CCc2ccc(NC(=O)CCc3ccccc3)c(O)c21]

N-[2-(6-Amino-7-hydroxy-2,3-dihydro-1H-inden-1-yl) ethyl]acetamide hydrochloride (100 mg, 0.369 mmol) was dissolved in pyridine (4 mL), 3-phenylpropionyl chloride (60.3 µL, 0.406 mmol) was added under ice-cooling, and the mixture was stirred for 15 min. Water was added to the reaction solution, and the solvent was evaporated under reduced pressure. The residue was purified by silica gel column chromatography (ethyl acetate/hexane=80/20→100/0) to give the title compound (74.4 mg, yield 55%).
$^1$H-NMR (CDCl$_3$) δ: 1.69-1.86 (3H, m), 2.00 (3H, s), 2.13-2.32 (1H, m), 2.66-2.78 (3H, m), 2.86-3.01 (1H, m), 3.06 (2H, t, J=7.7 Hz), 3.13-3.27 (1H, m), 3.28-3.42 (2H, m), 6.31 (1H, brs), 6.68 (1H, d, J=8.0 Hz), 6.99 (1H, d, J=8.0 Hz), 7.17-7.35 (5H, m), 7.86 (1H, brs), 9.68 (1H, s),
MS (ESI+): 367 (M+H).

REFERENCE EXAMPLE 40

N-{3-[2-(Acetylamino)ethyl]-4-hydroxy-2,3-dihydro-1H-inden-5-yl}-4-phenylbutanamide

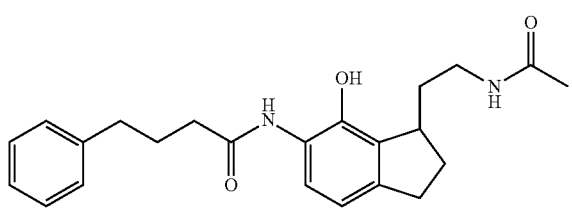 [SMILES: CC(=O)NCCC1CCc2ccc(NC(=O)CCCc3ccccc3)c(O)c21]

N-[2-(6-Amino-7-hydroxy-2,3-dihydro-1H-inden-1-yl) ethyl]acetamide hydrochloride (100 mg, 0.369 mmol) was dissolved in pyridine (4 mL), 4-phenylbutanoyl chloride (74.1 mg, 0.406 mmol) was added under ice-cooling, and the mixture was stirred for 15 min. Water was added to the reaction solution, and the solvent was evaporated under reduced pressure. The residue was purified by silica gel column chromatography (ethyl acetate/hexane=80/20→100/0) to give the title compound (96.8 mg, yield 69%).
$^1$H-NMR (CDCl$_3$) δ: 1.73-1.88 (3H, m), 2.01 (3H, s), 2.06-2.31 (3H, m), 2.43 (2H, t, J=7.4 Hz), 2.68-2.79 (3H, m), 2.89-3.03 (1H, m), 3.16-3.44 (3H, m), 6.16-6.30 (1H, m), 6.72 (1H, d, J=7.9 Hz), 7.12 (1H, d, J=7.9 Hz), 7.18-7.24 (3H, m), 7.27-7.34 (2H, m), 7.65 (1H, brs), 9.73 (1H, s),
MS (ESI+): 381 (M+H).

REFERENCE EXAMPLE 41

N-{3-[2-(Acetylamino)ethyl]-4-hydroxy-2,3-dihydro-1H-inden-5-yl}-5-pyridin-2-ylpentanamide

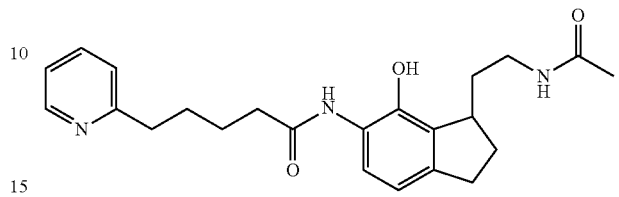

To 5-pyridin-2-ylpentanoic acid (72.8 mg, 0.406 mmol) was added thionyl chloride (0.4 mL), and the mixture was heated under reflux for 30 min. Thionyl chloride was evaporated under reduced pressure and the residue was diluted with pyridine (2 mL). The mixture was added to a solution of N-[2-(6-amino-7-hydroxy-2,3-dihydro-1H-inden-1-yl) ethyl]acetamide hydrochloride (100 mg, 0.369 mmol) in pyridine (2 mL) under ice-cooling, and the mixture was stirred for 15 min. Water was added, and the mixture was diluted with ethyl acetate, washed with saturated aqueous sodium hydrogencarbonate solution and saturated brine and dried over anhydrous sodium sulfate. The solvent was evaporated under reduced pressure, and the residue was purified by silica gel column chromatography (ethyl acetate/methanol=100/0→90/10) to give the title compound (37.7 mg, yield 26%).
$^1$H-NMR (CDCl$_3$) δ: 1.71-1.92 (7H, m), 1.98 (3H, s), 2.14-2.30 (1H, m), 2.49 (2H, t, J=6.9 Hz), 2.65-2.79 (1H, m), 2.79-3.03 (3H, m), 3.07-3.24 (1H, m), 3.29-3.49 (2H, m), 6.35 (1H, brs), 6.70 (1H, d, J=8.0 Hz), 7.03-7.20 (3H, m), 7.56-7.65 (1H, m), 8.47 (1H, d, J=5.8 Hz), 8.71 (1H, brs), hidden (1H).
MS (ESI+): 396 (M+H).

REFERENCE EXAMPLE 42

2-(2-Methyl-7,8-dihydro-6H-indeno[5,4-d][1,3]oxazol-8-yl)ethanamine hydrochloride

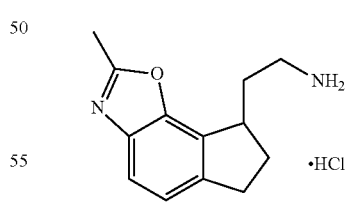

2-(2-Methyl-6,7-dihydro-8H-indeno[5,4-d][1,3]oxazol-8-ylidene)ethanamine (610 mg, 2.85 mmol) was dissolved in methanol (20 mL), a 10% palladium-carbon powder (61 mg) was added, and the mixture was stirred at room temperature for 24 hr under a hydrogen atmosphere. The catalyst was filtered off using celite, and the filtrate was concentrated. The residue was dissolved in ethyl acetate, converted to hydrochloride with 4N hydrochloric acid/ethyl acetate solution, and the solvent was evaporated under reduced pressure. Purification by recrystallization (ethyl acetate/methanol) gave the title compound (105 mg, yield 15%).

$^1$H-NMR (DMSO-d$_6$) δ: 1.68-1.87 (2H, m), 2.25-2.43 (2H, m), 2.58 (3H, s), 2.81-3.08 (4H, m), 3.39-3.53 (1H, m), 7.18 (1H, d, J=8.0 Hz), 7.43 (1H, d, J=8.0 Hz), 8.04 (3H, brs),
MS (ESI+): 217 (M+H),
Elemental analysis: for C$_{13}$H$_{17}$N$_2$ClO.0.6H$_2$O
Calcd. (%): C, 59.24; H, 6.95; N, 10.63
Found (%): C, 59.18; H, 6.77; N, 10.39.

REFERENCE EXAMPLE 43

2-Methyl-7-(1-methylethylidene)-6,7-dihydro-8H-indeno[5,4-d][1,3]oxazol-8-one

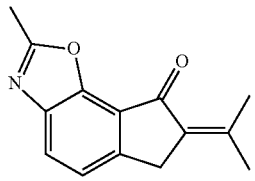 [SMILES: CC(C)=C1Cc2ccc3nc(C)oc3c2C1=O]

2-Methyl-6,7-dihydro-8H-indeno[5,4-d][1,3]oxazol-8-one (1.87 g, 10.0 mmol), acetone (3.68 mL, 50.0 mmol) and ICN Alumina B (manufactured by ICN, Akt.1, 20 g) were suspended in tetrahydrofuran (50 mL), and the mixture was stirred at 50° C. for 9 hr. Acetone (3.68 mL, 50.0 mmol) was added, and the mixture was further stirred for 12 hr. The reaction solution was filtered, and the filtrate was evaporated under reduced pressure. The residue was purified by silica gel column chromatography (ethyl acetate/hexane=10/90→50/50) to give the title compound (742 mg, yield 33%).

$^1$H-NMR (CDCl$_3$) δ: 2.03 (3H, s), 2.46 (3H, s), 2.71 (3H, s), 3.77 (2H, s), 7.36 (1H, d, J=8.0 Hz), 7.82 (1H, d, J=8.0 Hz),
melting point: 156-159° C. (recrystallized from ethyl acetate/hexane),
MS (ESI+): 228 (M+H),
Elemental analysis: for C$_{14}$H$_{13}$NO$_2$
Calcd. (%): C, 73.99; H, 5.76; N, 6.16
Found (%): C, 73.91; H, 5.69; N, 6.10.

REFERENCE EXAMPLE 44

7-Isopropyl-2-methyl-6,7-dihydro-8H-indeno[5,4-d][1,3]oxazol-8-one

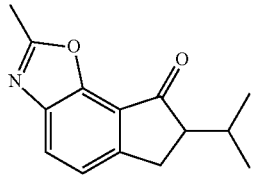 [SMILES: Cc1nc2ccc3c(c2o1)C(=O)C(C(C)C)C3]

To a solution of 2-methyl-7-(1-methylethylidene)-6,7-dihydro-8H-indeno[5,4-d][1,3]oxazol-8-one (677 mg, 2.98 mmol) in methanol/ethyl acetate (5/15 mL) was added a palladium-carbon powder (68 mg), and the mixture was stirred at room temperature for 40 hr under a hydrogen atmosphere. The catalyst was filtered off, and the filtrate was evaporated under reduced pressure. The residue was purified by silica gel column chromatography (ethyl acetate) to give the title compound (662 mg, yield 97%).

$^1$H-NMR (CDCl$_3$) δ: 0.83 (3H, d, J=6.9 Hz), 1.07 (3H, d, J=7.1 Hz), 2.39-2.53 (1H, m), 2.70 (3H, s), 2.74-2.82 (1H, m), 3.06 (1H, dd, J=17.6, 3.9 Hz), 3.28 (1H, dd, J=17.6, 8.0 Hz), 7.37 (1H, d, J=8.0 Hz), 7.85 (1H, d, J=8.0 Hz),
MS (ESI+): 230 (M+H).

REFERENCE EXAMPLE 45

(8-Hydroxy-7-isopropyl-2-methyl-7,8-dihydro-6H-indeno[5,4-d][1,3]oxazol-8-yl)acetonitrile

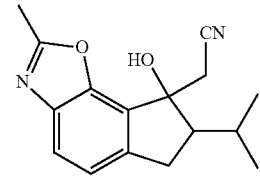 [SMILES: Cc1nc2ccc3c(c2o1)C(O)(CC#N)C(C(C)C)C3]

To a solution of 1,1,1,3,3,3-hexamethyldisilazane (917 mg, 5.68 mmol) in tetrahydrofuran (10 mL) was added 1.6M butyllithium/hexane solution (3.55 mL, 5.68 mmol) at −78° C., and the mixture was stirred for 15 min. Thereto was added a solution of acetonitrile (313 µL, 5.95 mmol) in tetrahydrofuran (2 mL), and the mixture was stirred for 30 min. Then, a solution of 7-isopropyl-2-methyl-6,7-dihydro-8H-indeno[5,4-d][1,3]oxazol-8-one (650 mg, 2.84 mmol) in tetrahydrofuran (2 mL) was added. After stirring for 30 min, the reaction solution was diluted with saturated aqueous ammonium chloride solution and ethyl acetate, washed with water and saturated brine and dried over anhydrous sodium sulfate. The solvent was evaporated under reduced pressure, and the residue was purified by silica gel column chromatography (ethyl acetate/hexane=20/80→100/0) to give the title compound (614 mg, yield 80%).

$^1$H-NMR (CDCl$_3$) δ: 1.03 (3H, d, J=6.6 Hz), 1.21 (3H, d, J=6.6 Hz), 2.06-2.18 (1H, m), 2.19 (1H, brs), 2.46 (1H, q, J=7.9 Hz), 2.66 (3H, s), 2.96 (1H, dd, J=15.9, 8.2 Hz), 3.16-3.30 (2H, m), 3.55 (1H, d, J=16.8 Hz), 7.16 (1H, d, J=8.0 Hz), 7.57 (1H, d, J=8.0 Hz).

melting point: 149-152° C. (recrystallized from ethyl acetate/hexane),
MS (ESI+): 271 (M+H),
Elemental analysis: for C$_{16}$H$_{18}$N$_2$O$_2$
Calcd. (%): C, 71.09; H, 6.71; N, 10.36
Found (%): C, 71.00; H, 6.79; N, 10.35.

EXAMPLE 1

N-[2-(6,7-Dihydro-8H-indeno[5,4-d][1,3]oxazol-8-ylidene)ethyl]acetamide

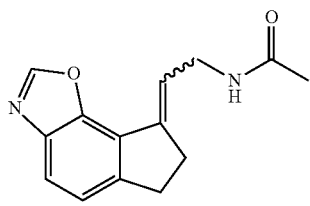 [SMILES: CC(=O)NCC=C1CCc2ccc3ncoc3c21]

2-(6,7-Dihydro-8H-indeno[5,4-d][1,3]oxazol-8-ylidene)ethanamine (30.0 mg, 0.148 mmol) was dissolved in tetrahydrofuran (1 mL), triethylamine (31.0 μL, 0.222 mmol) and acetic anhydride (16.8 μL, 0.178 mmol) were added under ice-cooling, and the mixture was stirred for 15 min. To the reaction solution was added saturated aqueous sodium hydrogencarbonate solution, and the mixture was extracted with ethyl acetate and washed with saturated brine. The solvent was evaporated under reduced pressure, and the residue was purified by silica gel column chromatography (ethyl acetate/methanol=100/0→95/5) to give the title compound (19.0 mg, yield 53%).

$^1$H-NMR (CDCl$_3$) δ: 2.03 (3H, s), 2.87-2.96 (2H, m), 3.14-3.24 (2H, m), 4.10 (2H, dd, J=6.9, 5.8 Hz), 5.62 (1H, brs), 6.28-6.37 (1H, m), 7.25 (1H, d, J=8.0 Hz), 7.62 (1H, d, J=8.0 Hz), 8.09 (1H, s),

MS (ESI+): 243 (M+H).

EXAMPLE 2

N-[2-(6,7-Dihydro-8H-indeno[5,4-d][1,3]oxazol-8-ylidene)ethyl]propionamide

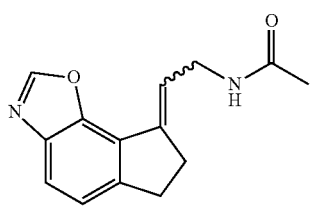 [SMILES: CC(=O)NCC=C1CCc2ccc3ncoc3c21]

2-(6,7-Dihydro-8H-indeno[5,4-d][1,3]oxazol-8-ylidene)ethanamine (30.0 mg, 0.148 mmol) was dissolved in tetrahydrofuran (1 mL), triethylamine (31.0 μL, 0.222 mmol) and propionic anhydride (22.8 μL, 0.178 mmol) were added under ice-cooling, and the mixture was stirred for 15 min. To the reaction solution was added saturated aqueous sodium hydrogencarbonate solution. The mixture was extracted with ethyl acetate and washed with saturated brine. The solvent was evaporated under reduced pressure, and the residue was purified by silica gel column chromatography (ethyl acetate/hexane=50/50→100/0) to give the title compound (33.9 mg, yield 89%).

$^1$H-NMR (CDCl$_3$) δ: 1.20 (3H, t, J=7.7 Hz), 2.26 (2H, q, J=7.7 Hz), 2.87-2.98 (2H, m), 3.14-3.24 (2H, m), 4.11 (2H, t, J=6.3 Hz), 5.59 (1H, brs), 6.26-6.37 (1H, m), 7.25 (1H, d, J=8.2 Hz), 7.62 (1H, d, J=8.2 Hz), 8.09 (1H, s), melting point: 148-150° C. (recrystallized from ethyl acetate),

MS (ESI+): 257 (M+H),

Elemental analysis: for C$_{15}$H$_{16}$N$_2$O$_2$

Calcd. (%): C, 70.29; H, 6.29; N, 10.93

Found (%): C, 69.97; H, 6.28; N, 10.96.

EXAMPLE 3

N-[2-(2-Methyl-6,7-dihydro-8H-indeno[5,4-d][1,3]oxazol-8-ylidene)ethyl]acetamide

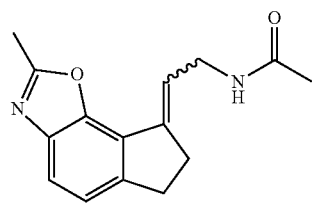 [SMILES: CC(=O)NCC=C1CCc2ccc3nc(C)oc3c21]

A half amount of 2-(2-methyl-6,7-dihydro-8H-indeno[5,4-d][1,3]oxazol-8-ylidene)ethanamine obtained in Reference Example 19 was dissolved in tetrahydrofuran (6.9 mL), triethylamine (144 μL, 1.04 mmol) and acetic anhydride (78.3 μL, 0.828 mmol) were added under ice-cooling, and the mixture was stirred for 15 min. To the reaction solution was added saturated aqueous sodium hydrogencarbonate solution, and the mixture was extracted with ethyl acetate and washed with saturated brine. The solvent was evaporated under reduced pressure, and the residue was purified by silica gel column chromatography (ethyl acetate/methanol=100/0→95/5) to give the title compound (171 mg).

$^1$H-NMR (CDCl$_3$) δ: 2.04 (3H, s), 2.67 (3H, s), 2.86-2.95 (2H, m), 3.12-3.21 (2H, m), 4.05-4.14 (2H, m), 5.58 (1H, brs), 6.22-6.35 (1H, m), 7.18 (1H, d, J=8.0 Hz), 7.48 (1H, d, J=8.0 Hz), melting point: 188-190° C. (recrystallized from ethyl acetate),

MS (ESI+): 257 (M+H),

Elemental analysis: for C$_{15}$H$_{16}$N$_2$O$_2$

Calcd. (%): C, 70.29; H, 6.29; N, 10.93

Found (%): C, 70.17; H, 6.17; N, 10.54.

EXAMPLE 4

N-[2-(2-Methyl-6H-indeno[5,4-d][1,3]oxazol-8-yl)ethyl]acetamide

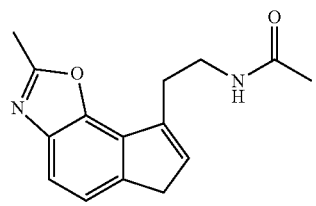 [SMILES: CC(=O)NCCC1=CCc2ccc3nc(C)oc3c21]

N-[2-(2-Methyl-6,7-dihydro-8H-indeno[5,4-d][1,3]oxazol-8-ylidene)ethyl]acetamide (63.5 mg, 0.248 mmol) was dissolved in toluene (2.5 mL), sulfuric acid (24.3 μL, 0.248 mmol) was added, and the mixture was stirred at 100° C. for 5 hr. To the reaction solution was added saturated aqueous sodium hydrogencarbonate solution. The mixture was extracted with ethyl acetate and washed with saturated brine. The solvent was evaporated under reduced pressure. The residue was purified by silica gel column chromatography (ethyl acetate/methanol=100/0→90/10) to give the title compound (40.0 mg, yield 63%).

$^1$H-NMR (CDCl$_3$) δ: 1.95 (3H, s), 2.68 (3H, s), 3.03 (2H, dt, J=6.7, 1.5 Hz), 3.43-3.54 (2H, m), 3.64-3.76 (2H, m), 5.56 (1H, brs), 6.36 (1H, s), 7.40 (1H, d, J=8.0 Hz), 7.49 (1H, d, J=8.0 Hz), melting point: 154-156° C. (recrystallized from hexane/ethyl acetate),

MS (ESI+): 257 (M+H),

Elemental analysis: for C$_{15}$H$_{16}$N$_2$O$_2$

Calcd. (%): C, 70.29; H, 6.29; N, 10.93

Found (%): C, 70.16; H, 6.27; N, 11.03.

EXAMPLE 5

N-[2-(2-Methyl-6,7-dihydro-8H-indeno[5,4-d][1,3]oxazol-8-ylidene)ethyl]propionamide

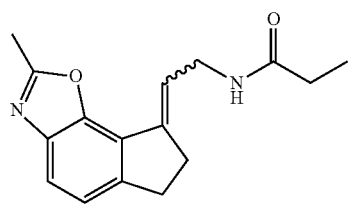 [SMILES: CCC(=O)NCC=C1CCc2ccc3nc(C)oc3c21]

A half amount of 2-(2-methyl-6,7-dihydro-8H-indeno[5,4-d][1,3]oxazol-8-ylidene)ethanamine obtained in Reference Example 19 was dissolved in tetrahydrofuran (6.9 mL), triethylamine (144 μL, 1.04 mmol) and propionic anhydride (106 μL, 0.828 mmol) were added under ice-cooling, and the mixture was stirred for 15 min. To the reaction solution was added saturated aqueous sodium hydrogencarbonate solution. The mixture was extracted with ethyl acetate, washed with saturated brine and the solvent was evaporated under reduced pressure. The residue was purified by silica gel column chromatography (ethyl acetate/hexane=50/50→100/0) to give the title compound (140 mg).

$^1$H-NMR (CDCl$_3$) δ: 1.20 (3H, t, J=7.7 Hz), 2.26 (2H, q, J=7.7 Hz), 2.67 (3H, s), 2.85-2.95 (2H, m), 3.11-3.22 (2H, m), 4.11 (2H, t, J=6.3 Hz), 5.61 (1H, brs), 6.23-6.32 (1H, m), 7.17 (1H, d, J=8.0 Hz), 7.47 (1H, d, J=8.0 Hz), melting point: 214-216° C. (recrystallized from ethyl acetate),

MS (ESI+): 271 (M+H),

Elemental analysis: for C$_{16}$H$_{18}$N$_2$O$_2$

Calcd. (%): C, 71.09; H, 6.71; N, 10.36

Found (%): C, 71.03; H, 6.65; N, 10.09.

EXAMPLE 6

N-{2-[2-(4-Phenylbutyl)-6,7-dihydro-8H-indeno[5,4-d][1,3]oxazol-8-ylidene]ethyl}acetamide

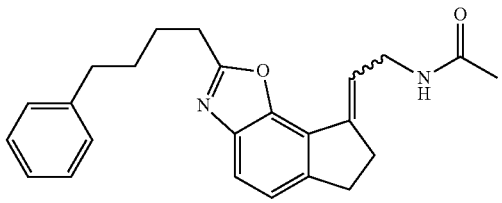 [SMILES: CC(=O)NCC=C1CCc2ccc3nc(CCCCc4ccccc4)oc3c21]

A half amount of 2-[2-(4-phenylbutyl)-6,7-dihydro-8H-indeno[5,4-d][1,3]oxazol-8-ylidene]ethanamine obtained in Reference Example 20 was dissolved in tetrahydrofuran (1.9 mL), triethylamine (40.0 μL, 0.287 mmol) and acetic anhydride (21.7 μL, 0.229 mmol) were added under ice-cooling, and the mixture was stirred for 15 min. To the reaction solution was added saturated aqueous sodium hydrogencarbonate solution. The mixture was extracted with ethyl acetate and washed with saturated brine. The solvent was evaporated under reduced pressure. The residue was purified by silica gel column chromatography (ethyl acetate/hexane=50/50→100/0) to give the title compound (43.0 mg).

$^1$H-NMR (CDCl$_3$) δ: 1.72-1.85 (2H, m), 1.88-2.01 (2H, m), 2.03 (3H, s), 2.70 (2H, t, J=7.4 Hz), 2.84-2.94 (2H, m), 2.98 (2H, t, J=7.4 Hz), 3.11-3.21 (2H, m), 4.05-4.14 (2H, m), 5.60 (1H, brs), 6.20-6.31 (1H, m), 7.12-7.22 (4H, m), 7.23-7.33 (2H, m), 7.49 (1H, d, J=8.0 Hz), melting point: 113-115° C. (recrystallized from hexane/ethyl acetate),

MS (ESI+): 375 (M+H),

Elemental analysis: for C$_{24}$H$_{26}$N$_2$O$_2$

Calcd. (%): C, 76.98; H, 7.00; N, 7.48

Found (%): C, 76.81; H, 6.99; N, 7.55.

EXAMPLE 7

N-{2-[2-(4-Phenylbutyl)-6,7-dihydro-8H-indeno[5,4-d][1,3]oxazol-8-ylidene]ethyl}propionamide

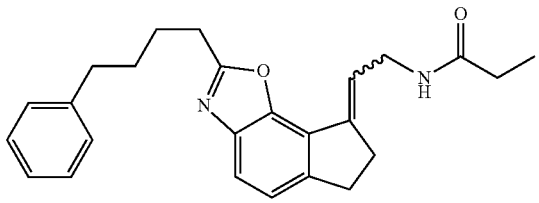 [SMILES: CCC(=O)NCC=C1CCc2ccc3nc(CCCCc4ccccc4)oc3c21]

A half amount of 2-[2-(4-phenylbutyl)-6,7-dihydro-8H-indeno[5,4-d][1,3]oxazol-8-ylidene]ethanamine obtained in Reference Example 20 was dissolved in tetrahydrofuran (1.9 mL), triethylamine (40.0 μL, 0.287 mmol) and propionic anhydride (29.4 μL, 0.229 mmol) were added under ice-cooling, and the mixture was stirred for 15 min. To the reaction solution was added saturated aqueous sodium hydrogencarbonate solution. The mixture was extracted with ethyl acetate and washed with saturated brine. The solvent was evaporated under reduced pressure. The residue was purified by silica gel column chromatography (ethyl acetate/hexane=30/70→70/30) to give the title compound (45.1 mg).

¹H-NMR (CDCl₃) δ: 1.20 (3H, t, J=7.4 Hz), 1.71-1.85 (2H, m), 1.88-2.04 (2H, m), 2.25 (2H, q, J=7.4 Hz), 2.70 (2H, t, J=7.6 Hz), 2.85-2.95 (2H, m), 2.99 (2H, t, J=7.6 Hz), 3.10-3.21 (2H, m), 4.07-4.15 (2H, m), 5.55 (1H, brs), 6.21-6.31 (1H, m), 7.13-7.22 (4H, m), 7.22-7.32 (2H, m), 7.49 (1H, d, J=8.0 Hz), melting point: 111-113° C. (recrystallized from hexane/ethyl acetate),

MS (ESI+): 389 (M+H),

Elemental analysis: for C₂₅H₂₈N₂O₂

Calcd. (%): C, 77.29; H, 7.26; N, 7.21

Found (%): C, 77.10; H, 7.28; N, 7.35.

EXAMPLE 8

N-[2-(2-Methyl-6,7-dihydro-8H-indeno[5,4-d][1,3]thiazol-8-ylidene)ethyl]acetamide

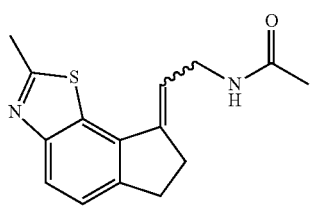 [SMILES: CC(=O)NCC=C1CCc2ccc3nc(C)sc3c21]

2-(2-Methyl-6,7-dihydro-8H-indeno[5,4-d][1,3]thiazol-8-ylidene)ethanamine obtained in Reference Example 21 was dissolved in tetrahydrofuran (30 mL), triethylamine (314 μL, 2.25 mmol) and acetic anhydride (85 μL, 0.899 mmol) were added under ice-cooling, and the mixture was stirred at room temperature for 10 min. To the reaction solution was added saturated aqueous sodium hydrogencarbonate solution. The mixture was extracted with ethyl acetate and washed with saturated brine. The solvent was evaporated under reduced pressure. The residue was purified by silica gel column chromatography (ethyl acetate/methanol=100/0→95/5) to give the title compound (76.0 mg, total yield from Reference Example 17 37%).

¹H-NMR (CDCl₃) δ: 2.03 (3H, s), 2.87 (3H, s), 2.91-3.00 (2H, m), 3.13-3.21 (2H, m), 4.08-4.17 (2H, m), 5.57 (1H, brs), 5.80-5.91 (1H, m), 7.36 (1H, d, J=8.2 Hz), 7.84 (1H, d, J=8.2 Hz), melting point: 184-186° C. (recrystallized from hexane/ethyl acetate),

MS (ESI+): 273 (M+H),

Elemental analysis: for C₁₅H₁₆N₂OS

Calcd. (%): C, 66.15; H, 5.92; N, 10.29

Found (%): C, 65.91; H, 5.83; N, 10.30.

EXAMPLE 9

N-[2-(7,8-Dihydro-6H-indeno[5,4-d][1,3]oxazol-8-yl)ethyl]acetamide

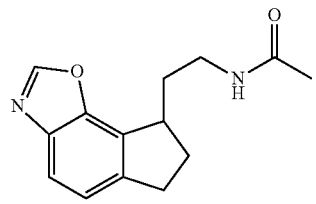 [SMILES: CC(=O)NCCC1CCc2ccc3ncoc3c21]

N-[2-(6,7-Dihydro-8H-indeno[5,4-d][1,3]oxazol-8-ylidene)ethyl]acetamide (19.0 mg, 0.0784 mmol) was dissolved in methanol (1 mL), a 10% palladium-carbon powder (10 mg) was added, and the mixture was stirred at room temperature for 1 hr under a hydrogen atmosphere. The catalyst was filtered off using celite, and the filtrate was concentrated under reduced pressure. The residue was purified by silica gel column chromatography (ethyl acetate/methanol=90/10) to give the title compound (16.0 mg, yield 84%).

¹H-NMR (CDCl₃) δ: 1.74-1.97 (2H, m), 1.99 (3H, s), 2.21-2.36 (1H, m), 2.39-2.54 (1H, m), 2.93-3.18 (2H, m), 3.27-3.41 (1H, m), 3.42-3.61 (2H, m), 5.56 (1H, brs), 7.23 (1H, d, J=8.0 Hz), 7.59 (1H, d, J=8.0 Hz), 8.03 (1H, s),

MS (ESI+): 245 (M+H).

EXAMPLE 10

N-[2-(7,8-Dihydro-6H-indeno[5,4-d][1,3]oxazol-8-yl)ethyl]propionamide

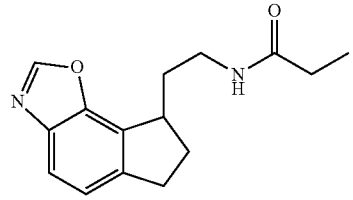 [SMILES: CCC(=O)NCCC1CCc2ccc3ncoc3c21]

N-[2-(6,7-Dihydro-8H-indeno[5,4-d][1,3]oxazol-8-ylidene)ethyl]propionamide (28.7 mg, 0.112 mmol) was dissolved in methanol (1.1 mL), a 10% palladium-carbon powder (14 mg) was added, and the mixture was stirred at room temperature for 1.5 hr under a hydrogen atmosphere. The catalyst was filtered off using celite, and the filtrate was concentrated under reduced pressure. The residue was purified by silica gel column chromatography (ethyl acetate/hexane=50/50→100/0) to give the title compound (25.6 mg, yield 88%).

¹H-NMR (CDCl₃) δ: 1.16 (3H, t, J=7.6 Hz), 1.75-1.99 (2H, m), 2.16-2.36 (3H, m), 2.38-2.53 (1H, m), 2.92-3.18 (2H, m), 3.28-3.42 (1H, m), 3.43-3.61 (2H, m), 5.55 (1H, brs), 7.23 (1H, d, J=8.2 Hz), 7.58 (1H, d, J=8.2 Hz), 8.03 (1H, s), melting point: 89-90° C. (recrystallized from hexane/ethyl acetate),

MS (ESI+): 259 (M+H),

Elemental analysis: for C₁₅H₁₈N₂O₂

Calcd. (%): C, 69.74; H, 7.02; N, 10.84
Found (%): C, 69.68; H, 7.03; N, 10.98.

EXAMPLE 11

N-[2-(2-Methyl-7,8-dihydro-6H-indeno[5,4-d][1,3]oxazol-8-yl)ethyl]acetamide

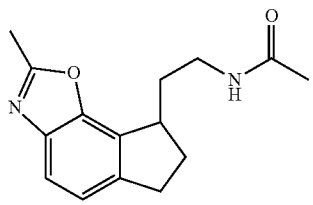

N-[2-(2-Methyl-6,7-dihydro-8H-indeno[5,4-d][1,3]oxazol-8-ylidene)ethyl]acetamide (165 mg, 0.644 mmol) was dissolved in methanol (6.4 mL), a 10% palladium-carbon powder (82 mg) was added, and the mixture was stirred at room temperature for 12 hr under a hydrogen atmosphere. The catalyst was filtered off using celite, and the filtrate was concentrated under reduced pressure. The residue was purified by silica gel column chromatography (ethyl acetate/methanol=100/0→95/5) to give the title compound (148 mg, yield 89%).

$^1$H-NMR (CDCl$_3$) δ: 1.69-1.96 (2H, m), 1.99 (3H, s), 2.23-2.50 (2H, m), 2.63 (3H, s), 2.89-3.15 (2H, m), 3.28-3.56 (3H, m), 5.54 (1H, brs), 7.15 (1H, d, J=8.0 Hz), 7.44 (1H, d, J=8.0 Hz), melting point: 93-95° C. (recrystallized from hexane/ethyl acetate),
MS (ESI+): 259 (M+H),
Elemental analysis: for C$_{15}$H$_{18}$N$_2$O$_2$
Calcd. (%): C, 69.74; H, 7.02; N, 10.84
Found (%): C, 69.77; H, 6.97; N, 10.95.

EXAMPLE 12

(S)-N-[2-(2-Methyl-7,8-dihydro-6H-indeno[5,4-d][1,3]oxazol-8-yl)ethyl]acetamide

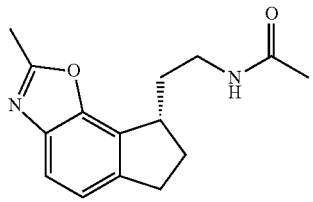 [SMILES: CC(=O)NCC[C@@H]1CCc2ccc3nc(C)oc3c21]

Racemic N-[2-(2-methyl-7,8-dihydro-6H-indeno[5,4-d][1,3]oxazol-8-yl)ethyl]acetamide (768 mg, 3.00 mmol) was fractionated by high performance liquid chromatography (instrument: Prep LC 2000 (manufactured by Nihon Waters K.K.), column: CHIRALPAK AD (50 mmID×500 mL, manufactured by Daicel Chemical Industries, Ltd.), mobile phase: hexane/ethanol/diethylamine=90/10/0.1, flow rate: 60 mL/min, column temperature: 30° C., sample concentration: 1.02 mg/mL, injection weight: 31 mg). A fraction containing an optically active compound having a shorter retention time under the above-mentioned high performance liquid chromatography conditions was concentrated. The concentrate was re-dissolved in ethanol, and concentrated to dryness. Hexane was added again, and the mixture was concentrated to dryness to give the title compound (381 mg, 99.9% ee). Enantiomer excess (ee) was measured by high performance liquid chromatography (column: CHIRALPAK AD (4.6 mmID×250 mL, manufactured by Daicel Chemical Industries, Ltd.), mobile phase: hexane/ethanol/diethylamine=90/10/0.1, flow rate: 0.5 mL/min, column temperature: 30° C., sample concentration: 0.65 mg/mL (hexane/ethanol), injection volume: 10 μL).

$^1$H-NMR (CDCl$_3$) δ: 1.69-1.96 (2H, m), 1.99 (3H, s), 2.23-2.50 (2H, m), 2.63 (3H, s), 2.89-3.15 (2H, m), 3.28-3.56 (3H, m), 5.54 (1H, brs), 7.15 (1H, d, J=8.0 Hz), 7.44 (1H, d, J=8.0 Hz), melting point: 111-113° C. (recrystallized from hexane/ethyl acetate),
MS (ESI+): 259 (M+H),
[α]$_D^{20}$: −53.4° (c 0.5035, methanol),
Elemental analysis: for C$_{15}$H$_{18}$N$_2$O$_2$
Calcd. (%): C, 69.74; H, 7.02; N, 10.84
Found (%): C, 69.53; H, 7.01; N, 10.96.

EXAMPLE 13

(R)-N-[2-(2-Methyl-7,8-dihydro-6H-indeno[5,4-d][1,3]oxazol-8-yl)ethyl]acetamide

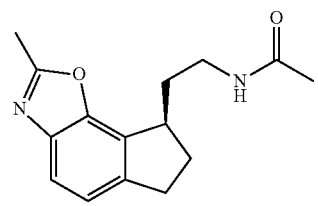 [SMILES: CC(=O)NCC[C@H]1CCc2ccc3nc(C)oc3c21]

By the method similar to Example 12, racemic N-[2-(2-methyl-7,8-dihydro-6H-indeno[5,4-d][1,3]oxazol-8-yl)ethyl]acetamide (768 mg, 3.00 mmol) was fractionated by high performance liquid chromatography (instrument: Prep LC 2000 (manufactured by Nihon Waters K.K.), column: CHIRALPAK AD (50 mmID×500 mL, manufactured by Daicel Chemical Industries, Ltd.), mobile phase: hexane/ethanol/diethylamine=90/10/0.1, flow rate: 60 mL/min, column temperature: 30° C., sample concentration: 1.02 mg/mL, injection weight: 31 mg). An optically active compound (381 mg, 99.7% ee) having a longer retention time under the above-mentioned high performance liquid chromatography conditions was obtained. Enantiomer excess (ee) was measured by high performance liquid chromatography (column: CHIRALPAK AD (4.6 mmID×250 mL, manufactured by Daicel Chemical Industries, Ltd.), mobile phase: hexane/ethanol/diethylamine=90/10/0.1, flow rate: 0.5 mL/min, column temperature: 30° C., sample concentration: 0.65 mg/mL (hexane/ethanol), injection volume: 10 μL).

$^1$H-NMR (CDCl$_3$) δ: 1.69-1.96 (2H, m), 1.99 (3H, s), 2.23-2.50 (2H, m), 2.63 (3H, s), 2.89-3.15 (2H, m), 3.28-3.56 (3H, m), 5.54 (1H, brs), 7.15 (1H, d, J=8.0 Hz), 7.44 (1H, d, J=8.0 Hz), melting point: 111-113° C. (recrystallized from hexane/ethyl acetate),
MS (ESI+): 259 (M+H),
[α]$_D^{20}$: +50.7° (c 0.5125, methanol),
Elemental analysis: for C$_{15}$H$_{18}$N$_2$O$_2$ Calcd. (%): C, 69.74; H, 7.02; N, 10.84
Found (%): C, 69.61; H, 7.01; N, 10.89.

EXAMPLE 14

N-[2-(2-Methyl-7,8-dihydro-6H-indeno[5,4-d][1,3]oxazol-8-yl)ethyl]propionamide

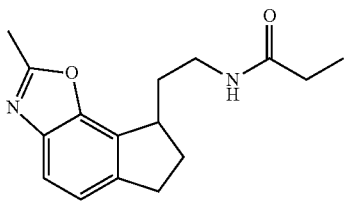 [SMILES: CCC(=O)NCCC1CCc2ccc3nc(C)oc3c21]

N-[2-(2-Methyl-6,7-dihydro-8H-indeno[5,4-d][1,3]oxazol-8-ylidene)ethyl]propionamide (135 mg, 0.499 mmol) was dissolved in methanol (5 mL), a 10% palladium-carbon powder (27 mg) was added, and the mixture was stirred at room temperature for 2.5 hr under a hydrogen atmosphere. The catalyst was filtered off using celite, and the filtrate was concentrated under reduced pressure. The residue was purified by silica gel column chromatography (ethyl acetate/hexane=50/50→100/0) to give the title compound (115 mg, yield 85%).

$^1$H-NMR (CDCl$_3$) δ: 1.16 (3H, t, J=7.6 Hz), 1.70-1.98 (2H, m), 2.15-2.51 (4H, m), 2.63 (3H, s), 2.88-3.15 (2H, m), 3.28-3.56 (3H, m), 5.54 (1H, brs), 7.14 (1H, d, J=7.7 Hz), 7.44 (1H, d, J=7.7 Hz), melting point: 111-113° C. (recrystallized from hexane/ethyl acetate),

MS (ESI+): 273 (M+H),

Elemental analysis: for C$_{16}$H$_{20}$N$_2$O$_2$·0.1H$_2$O
Calcd. (%): C, 70.10; H, 7.43; N, 10.22
Found (%): C, 70.14; H, 7.28; N, 10.23.

EXAMPLE 15

(S)-N-[2-(2-Methyl-7,8-dihydro-6H-indeno[5,4-d][1,3]oxazol-8-yl)ethyl]propionamide

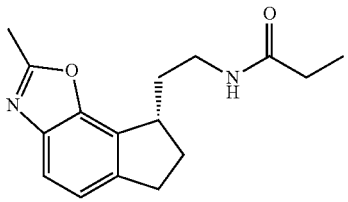 [SMILES: CCC(=O)NCC[C@@H]1CCc2ccc3nc(C)oc3c21]

Racemic N-[2-(2-methyl-7,8-dihydro-6H-indeno[5,4-d][1,3]oxazol-8-yl)ethyl]propionamide (96 mg, 0.353 mmol) was fractionated by high performance liquid chromatography (instrument: Prep LC 2000 (manufactured by Nihon Waters K.K.), column: CHIRALPAK AS (50 mmID×500 mL, manufactured by Daicel Chemical Industries, Ltd.), mobile phase: hexane/ethanol/diethylamine=94/6/0.1, flow rate: 60 mL/min, column temperature: 30° C., sample concentration: 1.61 mg/mL, injection weight: 48 mg). A fraction containing an optically active compound having a shorter retention time under the above-mentioned high performance liquid chromatography conditions was concentrated. The concentrate was re-dissolved in ethanol, and concentrated to dryness. Hexane was added again, and the mixture was concentrated to dryness to give the title compound (46 mg, 99.9% ee). Enantiomer excess (ee) was measured by high performance liquid chromatography (column: CHIRALPAK AS (4.6 mmID×250 mL, manufactured by Daicel Chemical Industries, Ltd.), mobile phase: hexane/ethanol/diethylamine=95/5/0.1, flow rate: 0.5 mL/min, column temperature: 30° C., sample concentration: 0.62 mg/mL (hexane/ethanol), injection volume: 10 μL).

$^1$H-NMR (CDCl$_3$) δ: 1.16 (3H, t, J=7.6 Hz), 1.70-1.98 (2H, m), 2.15-2.51 (4H, m), 2.63 (3H, s), 2.88-3.15 (2H, m), 3.28-3.56 (3H, m), 5.54 (1H, brs), 7.14 (1H, d, J=7.7 Hz), 7.44 (1H, d, J=7.7 Hz), melting point: 129-131° C. (recrystallized from hexane/ethyl acetate),

MS (ESI+): 273 (M+H),

[α]$_D^{20}$: −48.8° (c 0.535, methanol),

Elemental analysis: for C$_{16}$H$_{20}$N$_2$O$_2$
Calcd. (%): C, 70.56; H, 7.40; N, 10.29
Found (%): C, 70.40; H, 7.39; N, 10.34.

EXAMPLE 16

(R)-N-[2-(2-Methyl-7,8-dihydro-6H-indeno[5,4-d][1,3]oxazol-8-yl)ethyl]propionamide

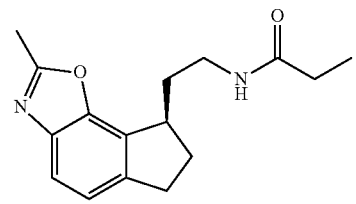 [SMILES: CCC(=O)NCC[C@H]1CCc2ccc3nc(C)oc3c21]

By a method similar to Example 15, racemic N-[2-(2-methyl-7,8-dihydro-6H-indeno[5,4-d][1,3]oxazol-8-yl)ethyl]propionamide (96 mg, 0.353 mmol) was fractionated by high performance liquid chromatography (instrument: Prep LC 2000 (manufactured by Nihon Waters K.K.), column: CHIRALPAK AS (50 mmID×500 mL, manufactured by Daicel Chemical Industries, Ltd.), mobile phase: hexane/ethanol/diethylamine=94/6/0.1, flow rate: 60 mL/min, column temperature: 30° C., sample concentration: 1.61 mg/mL, injection weight: 48 mg). An optically active compound (45 mg, 99.7% ee) having a longer retention time under the above-mentioned high performance liquid chromatography conditions was obtained. Enantiomer excess (ee) was measured by high performance liquid chromatography (column: CHIRALPAK AS (4.6 mmID×250 mL, manufactured by Daicel Chemical Industries, Ltd.), mobile phase: hexane/ethanol/diethylamine=95/5/0.1, flow rate: 0.5 mL/min, column temperature: 30° C., sample concentration: 0.62 mg/mL (hexane/ethanol), injection volume: 10 μL).

$^1$H-NMR (CDCl$_3$) δ: 1.16 (3H, t, J=7.6 Hz), 1.70-1.98 (2H, m), 2.15-2.51 (4H, m), 2.63 (3H, s), 2.88-3.15 (2H, m), 3.28-3.56 (3H, m), 5.54 (1H, brs), 7.14 (1H, d, J=7.7 Hz), 7.44 (1H, d, J=7.7 Hz), melting point: 129-131° C. (recrystallized from hexane/ethyl acetate),

MS (ESI+): 273 (M+H),

[α]$_D^{20}$: +48.2° (c 0.550, methanol),

Elemental analysis: for C$_{16}$H$_{20}$N$_2$O$_2$

Calcd. (%): C, 70.56; H, 7.40; N, 10.29
Found (%): C, 70.30; H, 7.37; N, 10.31.

EXAMPLE 17

N-{2-[2-(4-Phenylbutyl)-7,8-dihydro-6H-indeno[5,4-d][1,3]oxazol-8-yl]ethyl}acetamide

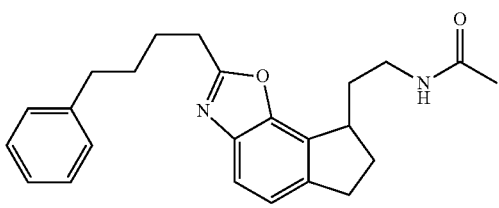 [SMILES: CC(=O)NCCC1CCc2ccc3nc(CCCCc4ccccc4)oc3c21]

N-{2-[2-(4-Phenylbutyl)-6,7-dihydro-8H-indeno[5,4-d][1,3]oxazol-8-ylidene]ethyl}acetamide (32.5 mg, 0.0868 mmol) was dissolved in methanol (0.87 mL), a 10% palladium-carbon powder (6 mg) was added, and the mixture was stirred at room temperature for 24 hr under a hydrogen atmosphere. The catalyst was filtered off using celite, and the filtrate was concentrated under reduced pressure. The residue was purified by silica gel column chromatography (ethyl acetate) to give the title compound (29.8 mg, yield 91%).

$^1$H-NMR (CDCl$_3$) δ: 1.70-2.01 (6H, m), 1.97 (3H, s), 2.16-2.32 (1H, m), 2.36-2.50 (1H, m), 2.69 (2H, t, J=7.6 Hz), 2.90-3.13 (4H, m), 3.26-3.39 (1H, m), 3.41-3.54 (2H, m), 5.52 (1H, brs), 7.12-7.22 (4H, m), 7.23-7.31 (2H, m), 7.46 (1H, d, J=8.0 Hz),

MS (ESI+): 377 (M+H).

EXAMPLE 18

N-{2-[2-(4-Phenylbutyl)-7,8-dihydro-6H-indeno[5,4-d][1,3]oxazol-8-yl]ethyl}propionamide

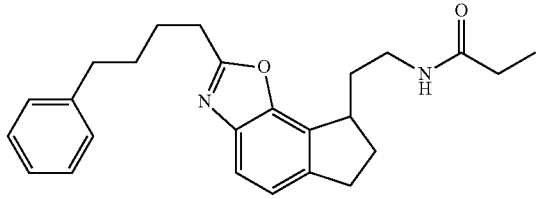

N-{2-[2-(4-Phenylbutyl)-6,7-dihydro-8H-indeno[5,4-d][1,3]oxazol-8-ylidene]ethyl}propionamide (35.7 mg, 0.0919 mmol) was dissolved in methanol (0.92 mL), a 10% palladium-carbon powder (7 mg) was added, and the mixture was stirred at room temperature for 10 hr under a hydrogen atmosphere. The catalyst was filtered off using celite, and the filtrate was concentrated under reduced pressure. The residue was purified by silica gel column chromatography (ethyl acetate/hexane=33/67) to give the title compound (31.2 mg, yield 87%).

$^1$H-NMR (CDCl$_3$) δ: 1.15 (3H, t, J=7.6 Hz), 1.71-2.00 (6H, m), 2.13-2.30 (3H, m), 2.34-2.52 (1H, m), 2.69 (2H, t, J=7.6 Hz), 2.89-3.15 (4H, m), 3.27-3.41 (1H, m), 3.42-3.55 (2H, m), 5.51 (1H, brs), 7.11-7.21 (4H, m), 7.23-7.31 (2H, m), 7.46 (1H, d, J=8.0 Hz),

MS (ESI+): 391 (M+H).

EXAMPLE 19

N-[2-(2-Methyl-7,8-dihydro-6H-indeno[5,4-d][1,3]thiazol-8-yl)ethyl]acetamide

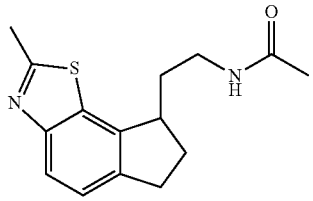 [SMILES: CC(=O)NCCC1CCc2ccc3nc(C)sc3c21]

N-[2-(2-Methyl-6,7-dihydro-8H-indeno[5,4-d][1,3]thiazol-8-ylidene)ethyl]acetamide (61.0 mg, 0.224 mmol) was dissolved in methanol (3 mL), a 10% palladium-carbon powder (10 mg) was added, and the mixture was stirred at room temperature for 15 hr under a hydrogen atmosphere. The catalyst was filtered off using celite, and the filtrate was concentrated under reduced pressure. The residue was purified by silica gel column chromatography (ethyl acetate/methanol=100/0→95/5) to give the title compound (49.6 mg, yield 81%).

$^1$H-NMR (CDCl$_3$) δ: 1.60-1.80 (1H, m), 1.84-2.06 (4H, m), 2.14-2.30 (1H, m), 2.34-2.51 (1H, m), 2.82 (3H, s), 2.88-3.18 (2H, m), 3.24-3.51 (3H, m), 5.62 (1H, brs), 7.30 (1H, d, J=8.2 Hz), 7.76 (1H, d, J=8.2 Hz),

MS (ESI+): 275 (M+H).

EXAMPLE 20

(S)-N-[2-(2-Methyl-7,8-dihydro-6H-indeno[5,4-d][1,3]thiazol-8-yl)ethyl]acetamide

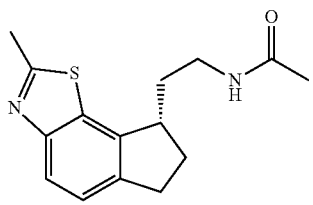 [SMILES: CC(=O)NCC[C@@H]1CCc2ccc3nc(C)sc3c21]

Racemic N-[2-(2-methyl-7,8-dihydro-6H-indeno[5,4-d][1,3]thiazol-8-yl)ethyl]acetamide (1.00 g) was fractionated by high performance liquid chromatography (instrument: Prep LC 2000 (manufactured by Nihon Waters K.K.), column: CHIRALPAK AD (50 mmID×500 mL, manufactured by Daicel Chemical Industries, Ltd.), mobile phase: hexane/ethanol=90/10, flow rate: 80 mL/min, column temperature: 30° C., sample concentration: 10 mg/mL (hexane/ethanol=90/10), injection weight: 500 mg×2). A fraction containing an optically active compound having a shorter retention time under the above-mentioned high performance liquid chromatography conditions was concentrated to give the title compound (504 mg, 99.9% ee). Enantiomer excess (ee) was measured by high performance liquid chromatography (column: CHIRALPAK AD (4.6 mmID×250 mL, manufactured by Daicel Chemical Industries, Ltd.), mobile phase: hexane/ethanol=90/10, flow rate: 1.0 mL/min, column temperature:

30° C., sample concentration: 0.25 mg/mL (hexane/ethanol=90/10), injection volume: 10 μL).

$^1$H-NMR (CDCl$_3$) δ: 1.65-1.80 (1H, m), 1.88-2.06 (1H, m), 1.94 (3H, s), 2.14-2.29 (1H, m), 2.35-2.51 (1H, m), 2.83 (3H, s), 2.91-3.19 (2H, m), 3.24-3.52 (3H, m), 5.44 (1H, brs), 7.31 (1H, d, J=8.1 Hz), 7.77 (1H, d, J=8.1 Hz), melting point: 116-117° C. (recrystallized from hexane/ethyl acetate),

MS (ESI+): 275 (M+H),

[α]$_D^{20}$: −133.0° (c 0.4480, methanol),

Elemental analysis: for C$_{15}$H$_{18}$N$_2$OS

Calcd. (%): C, 65.66; H, 6.61; N, 10.21

Found (%): C, 65.73; H, 6.76; N, 10.10.

EXAMPLE 21

(R)-N-[2-(2-Methyl-7,8-dihydro-6H-indeno[5,4-d][1,3]thiazol-8-yl)ethyl]acetamide

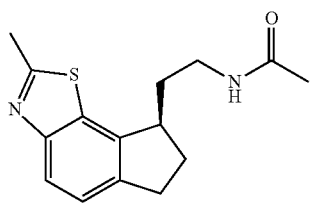 [SMILES: CC(=O)NCC[C@H]1CCc2ccc3nc(C)sc3c21]

Racemic N-[2-(2-methyl-7,8-dihydro-6H-indeno[5,4-d][1,3]thiazol-8-yl)ethyl]acetamide (1.00 g) was fractionated by high performance liquid chromatography (instrument: Prep LC 2000 (manufactured by Nihon Waters K.K.), column: CHIRALPAK AD (50 mmID×500 mL, manufactured by Daicel Chemical Industries, Ltd.), mobile phase: hexane/ethanol=90/10, flow rate: 80 mL/min, column temperature: 30° C., sample concentration: 10 mg/mL (hexane/ethanol=90/10), injection weight: 500 mg×2). A fraction containing an optically active compound having a longer retention time under the above-mentioned high performance liquid chromatography conditions was concentrated to give the title compound (492 mg, 99.9% ee). Enantiomer excess (ee) was measured by high performance liquid chromatography (column: CHIRALPAK AD (4.6 mmID×250 mL, manufactured by Daicel Chemical Industries, Ltd.), mobile phase: hexane/ethanol=90/10, flow rate: 1.0 mL/min, column temperature: 30° C., sample concentration: 0.25 mg/mL (hexane/ethanol=90/10), injection volume: 10 μL).

$^1$H-NMR (CDCl$_3$) δ: 1.67-1.80 (1H, m), 1.85-2.06 (1H, m), 1.95 (3H, s), 2.12-2.30 (1H, m), 2.35-2.51 (1H, m), 2.83 (3H, s), 2.91-3.18 (2H, m), 3.24-3.52 (3H, m), 5.46 (1H, brs), 7.31 (1H, d, J=8.1 Hz), 7.77 (1H, d, J=8.1 Hz), melting point: 115-116° C. (recrystallized from hexane/ethyl acetate),

MS (ESI+): 275 (M+H),

[α]$_D^{20}$: +136.5° (c 0.5035, methanol),

Elemental analysis: for C$_{15}$H$_{18}$N$_2$OS

Calcd. (%): C, 65.66; H, 6.61; N, 10.21

Found (%): C, 65.69; H, 6.77; N, 10.19.

EXAMPLE 22

N-[2-(2-Ethyl-7,8-dihydro-6H-indeno[5,4-d][1,3]oxazol-8-yl)ethyl]acetamide

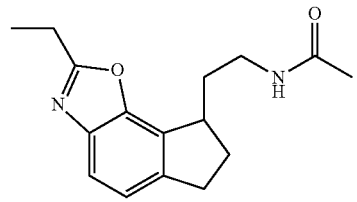 [SMILES: CCc1nc2ccc3c(c2o1)C(CCNC(C)=O)CC3]

N-{3-[2-(Acetylamino)ethyl]-4-hydroxy-2,3-dihydro-1H-inden-5-yl}propanamide (88.5 mg, 0.305 mmol) and pyridinium p-toluenesulfonate (15.3 mg, 0.061 mmol) were heated under reflux in xylene (3.1 mL) for 2.5 hr. The solvent was evaporated under reduced pressure, and the residue was purified by silica gel column chromatography (ethyl acetate/hexane=50/50→100/0) to give the title compound (69.8 mg, yield 84%).

$^1$H-NMR (CDCl$_3$) δ: 1.46 (3H, t, J=7.7 Hz), 1.71-1.96 (2H, m), 1.98 (3H, s), 2.20-2.34 (1H, m), 2.36-2.51 (1H, m), 2.96 (2H, q, J=7.7 Hz), 2.98-3.15 (2H, m), 3.28-3.41 (1H, m), 3.42-3.57 (2H, m), 5.54 (1 H, brs), 7.15 (1H, d, J=8.0 Hz), 7.46 (1H, d, J=8.0 Hz), melting point: 76-78° C. (recrystallized from hexane/ethyl acetate),

MS (ESI+): 273 (M+H),

Elemental analysis: for C$_{16}$H$_{20}$N$_2$O$_2$

Calcd. (%): C, 70.56; H, 7.40; N, 10.29

Found (%): C, 70.25; H, 7.35; N, 10.33.

EXAMPLE 23

N-{2-[2-(Hydroxymethyl)-7,8-dihydro-6H-indeno[5,4-d][1,3]oxazol-8-yl]ethyl}acetamide

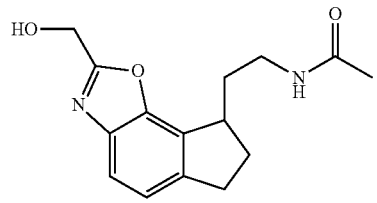 [SMILES: CC(=O)NCCC1CCc2ccc3nc(CO)oc3c21]

To a solution of N-(2-{2-[(benzyloxy)methyl]-7,8-dihydro-6H-indeno[5,4-d][1,3]oxazol-8-yl}ethyl)acetamide (50.0 mg, 0.131 mmol) in methanol (1 mL) was added a 10% palladium-carbon powder (100 mg), and the mixture was stirred at 50° C. for 24 hr under a hydrogen atmosphere. The catalyst was filtered off, and the filtrate was concentrated under reduced pressure. The residue was purified by silica gel column chromatography (methanol/ethyl acetate=0/100→5/95) and recrystallized (ethyl acetate/hexane) to give the title compound (19.0 mg, yield 53%).

$^1$H-NMR (CDCl$_3$) δ: 1.80-1.97 (2H, m), 1.99 (3H, s), 2.08-2.25 (1H, m), 2.36-2.51 (1H, m), 2.91-3.16 (2H, m), 3.33-3.61 (4H, m), 4.90 (2H, d, J=5.5 Hz), 5.57 (1H, brs), 7.19 (1H, d, J=8.0 Hz), 7.50 (1H, d, J=8.0 Hz),
melting point: 132-134° C. (ethyl acetate/hexane),
MS (ESI+): 275 (M+H),
Elemental analysis: for $C_{15}H_{18}N_2O_3$
Calcd. (%): C, 65.68; H, 6.61; N, 10.21
Found (%): C, 65.54; H, 6.63; N, 10.11.

EXAMPLE 24

N-[2-(2-Isopropyl-7,8-dihydro-6H-indeno[5,4-d][1,3]oxazol-8-yl)ethyl]acetamide

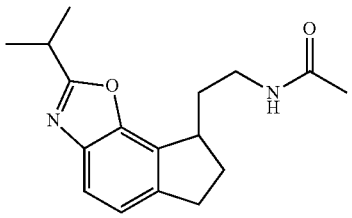

N-{3-[2-(Acetylamino)ethyl]-4-hydroxy-2,3-dihydro-1H-inden-5-yl}-2-methylpropanamide (118 mg, 0.369 mmol) and pyridinium p-toluenesulfonate (18.5 mg, 0.074 mmol) were heated under reflux in xylene (3.7 mL) for 5 hr. The solvent was evaporated under reduced pressure, and the residue was purified by silica gel column chromatography (methanol/ethyl acetate=0/100→10/90) to give the title compound (60 mg, yield 57%).
$^1$H-NMR (CDCl$_3$) δ: 1.46 (6H, dd, J=6.9, 1.1 Hz), 1.72-1.95 (2H, m), 1.98 (3H, s), 2.16-2.33 (1H, m), 2.34-2.51 (1H, m), 2.86-3.61 (6H, m), 5.73 (1H, brs), 7.14 (1H, d, J=8.2 Hz), 7.47 (1H, d, J=8.2 Hz),
MS (ESI+): 287 (M+H).

EXAMPLE 25

N-{2-[2-(Trifluoromethyl)-7,8-dihydro-6H-indeno[5,4-d][1,3]oxazol-8-yl]ethyl}acetamide

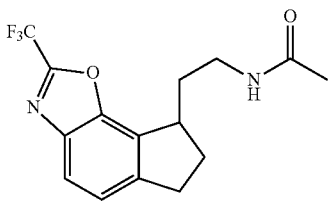 [SMILES: CC(=O)NCCC1CCc2ccc3nc(C(F)(F)F)oc3c21]

N-{3-[2-(Acetylamino)ethyl]-4-hydroxy-2,3-dihydro-1H-inden-5-yl}-2,2,2-trifluoroacetamide (27.8 mg, 0.0842 mmol) and pyridinium p-toluenesulfonate (4.2 mg, 0.0168 mmol) were heated under reflux in xylene (1 mL) for 5 hr. The solvent was evaporated under reduced pressure, and the residue was purified by silica gel column chromatography (ethyl acetate/hexane=50/50→100/0) to give the title compound (17.2 mg, yield 65%).
$^1$H-NMR (CDCl$_3$) δ: 1.72-1.88 (1H, m), 1.88-2.01 (1H, m), 2.00 (3H, s), 2.26-2.41 (1H, m), 2.43-2.57 (1H, m), 2.94-3.21 (2H, m), 3.31-3.64 (3H, m), 5.57 (1H, brs), 7.33 (1H, d, J=8.2 Hz), 7.66 (1H, d, J=8.2 Hz),
melting point: 114-116° C. (recrystallized from hexane/ethyl acetate),
MS (ESI+): 313 (M+H).

EXAMPLE 26

N-{2-[2-(4-Hydroxybutyl)-7,8-dihydro-6H-indeno[5,4-d][1,3]oxazol-8-yl]ethyl}acetamide

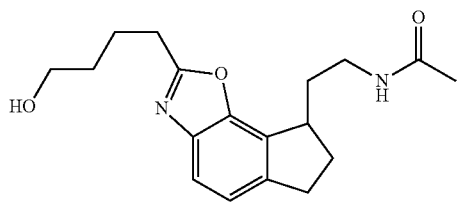 [SMILES: CC(=O)NCCC1CCc2ccc3nc(CCCCO)oc3c21]

To a solution of N-(2-{2-[4-(benzyloxy)butyl]-7,8-dihydro-6H-indeno[5,4-d][1,3]oxazol-8-yl}ethyl)acetamide (79.5 mg, 0.196 mmol) in methanol (2 mL) was added a 10% palladium-carbon powder (160 mg), and the mixture was stirred at room temperature for 6 hr under a hydrogen atmosphere. The catalyst was filtered off, and the filtrate was concentrated under reduced pressure. The residue was purified by silica gel column chromatography (methanol/ethyl acetate=0/100→5/95) to give the title compound (50.0 mg, yield 81%).
$^1$H-NMR (CDCl$_3$) δ: 1.67-2.08 (9H, m), 2.12-2.30 (1H, m), 2.33-2.51 (1H, m), 2.89-3.15 (4H, m), 3.25-3.58 (3H, m), 3.69 (2H, t, J=6.3 Hz), 5.61 (1H, brs), 7.15 (1H, d, J=8.0 Hz), 7.45 (1H, d, J=8.0 Hz), hidden (1H),
MS (ESI+): 317 (M+H).

EXAMPLE 27

N-{2-[2-(3-Hydroxybutyl)-7,8-dihydro-6H-indeno[5,4-d][1,3]oxazol-8-yl]ethyl}acetamide

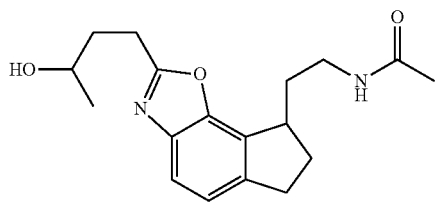 [SMILES: CC(=O)NCCC1CCc2ccc3nc(CCC(C)O)oc3c21]

To a solution of N-(2-{2-[3-(benzyloxy)butyl]-7,8-dihydro-6H-indeno[5,4-d][1,3]oxazol-8-yl}ethyl)acetamide (155 mg, 0.381 mmol) in methanol (4 mL) was added a 10% palladium-carbon powder (300 mg), and the mixture was stirred at 50° C. for 4 hr under a hydrogen atmosphere. The catalyst was filtered off, and the filtrate was concentrated under reduced pressure. The residue was purified by silica gel column chromatography (methanol/ethyl acetate=0/100→5/95) to give the title compound (101 mg, yield 84%).
$^1$H-NMR (CDCl$_3$) δ: 1.22-1.29 (3H, m), 1.65-2.29 (9H, m), 2.32-2.49 (1H, m), 2.86-3.15 (4H, m), 3.24-3.60 (3H, m), 3.79-4.04 (1H, m), 5.64 (1H, brs), 7.14 (1H, d, J=8.0 Hz), 7.44 (1H, d, J=8.0 Hz),
MS (ESI+): 317 (M+H).

EXAMPLE 28

N-{2-[2-(3-Oxobutyl)-7,8-dihydro-6H-indeno[5,4-d][1,3]oxazol-8-yl]ethyl}acetamide

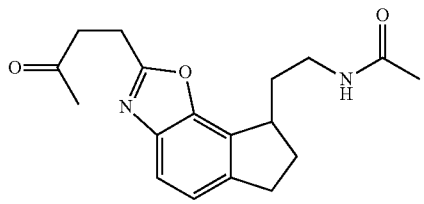 [SMILES: CC(=O)CCc1nc2ccc3c(c2o1)C(CCNC(C)=O)CC3]

A suspension of N-{2-[2-(3-hydroxybutyl)-7,8-dihydro-6H-indeno[5,4-d][1,3]oxazol-8-yl]ethyl}acetamide (72.0 mg, 0.228 mmol), 4 Å molecular sieves (72 mg), 4-methylmorpholine N-oxide (66.8 mg, 0.570 mmol) and tetra-n-propylammonium perruthenate(VII) (8.0 mg, 0.0228 mmol) in acetonitrile (3 mL) was stirred at room temperature for 2 hr. To the reaction mixture was added water and the mixture was extracted with ethyl acetate. The extract was washed with saturated brine and dried over anhydrous sodium sulfate. The solvent was evaporated under reduced pressure, and the residue was purified by silica gel column chromatography (methanol/ethyl acetate=0/100→5/95) and recrystallized (ethyl acetate/hexane) to give the title compound (22.2 mg, yield 31%).

$^1$H-NMR (CDCl$_3$) δ: 1.72-1.96 (2H, m), 1.98 (3H, s), 2.17-2.33 (4H, m), 2.35-2.48 (1H, m), 2.88-3.13 (4H, m), 3.15-3.23 (2H, m), 3.25-3.37 (1H, m), 3.41-3.57 (2H, m), 5.63 (1H, brs), 7.14 (1H, d, J=8.2 Hz), 7.40-7.45 (1H, m),
melting point: 111-112° C. (ethyl acetate/hexane),
MS (ESI+): 315 (M+H),
Elemental analysis: for C$_{18}$H$_{22}$N$_2$O$_3$
Calcd. (%): C, 68.77; H, 7.05; N, 8.91
Found (%): C, 68.66; H, 7.04; N, 8.92.

EXAMPLE 29

N-[2-(2-Cyclopropyl-7,8-dihydro-6H-indeno[5,4-d][1,3]oxazol-8-yl)ethyl]acetamide

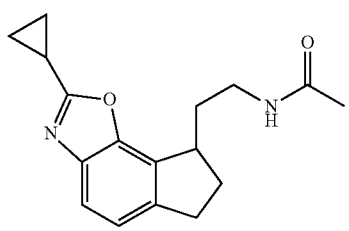 [SMILES: CC(=O)NCCC1CCc2ccc3nc(C4CC4)oc3c21]

N-{3-[2-(Acetylamino)ethyl]-4-hydroxy-2,3-dihydro-1H-inden-5-yl}cyclopropanecarboxamide (119 mg, 0.369 mmol) and pyridinium p-toluenesulfonate (18.5 mg, 0.074 mmol) were heated under reflux in xylene (3.7 mL) for 5 hr. The solvent was evaporated under reduced pressure, and the residue was purified by silica gel column chromatography (methanol/ethyl acetate=0/100→10/90) to give the title compound (73 mg, yield 70%).

$^1$H-NMR (CDCl$_3$) δ: 1.10-1.20 (2H, m), 1.21-1.29 (2H, m), 1.69-1.93 (2H, m), 1.98 (3H, s), 2.11-2.30 (2H, m), 2.31-2.49 (1H, m), 2.84-3.16 (2H, m), 3.25-3.57 (3H, m), 5.73 (1H, brs), 7.11 (1H, d, J=8.0 Hz), 7.38 (1H, d, J=8.0 Hz),
melting point: 92-95° C. (recrystallized from hexane/ethyl acetate),
MS (ESI+): 285 (M+H),
Elemental analysis: for C$_{17}$H$_{20}$N$_2$O$_2$
Calcd. (%): C, 71.81; H, 7.09; N, 9.85
Found (%): C, 71.69; H, 7.11; N, 9.79.

EXAMPLE 30

N-[2-(2-Phenyl-7,8-dihydro-6H-indeno[5,4-d][1,3]oxazol-8-yl)ethyl]acetamide

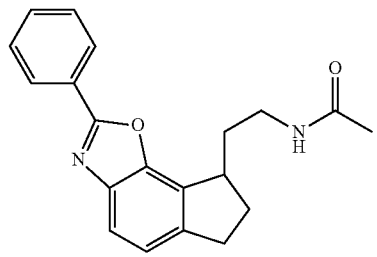 [SMILES: CC(=O)NCCC1CCc2ccc3nc(-c4ccccc4)oc3c21]

N-{3-[2-(Acetylamino)ethyl]-4-hydroxy-2,3-dihydro-1H-inden-5-yl}benzamide (100 mg, 0.257 mmol) and pyridinium p-toluenesulfonate (12.9 mg, 0.0513 mmol) were heated under reflux in xylene (5 mL) for 2.5 hr. The solvent was evaporated under reduced pressure, and the residue was purified by silica gel column chromatography (NH, ethyl acetate/hexane=30/70→60/40) and recrystallized (ethyl acetate/diisopropyl ether) to give the title compound (67.5 mg, yield 82%).

$^1$H-NMR (CDCl$_3$) δ: 1.76-1.97 (2H, m), 1.99 (3H, s), 2.31-2.57 (2H, m), 2.92-3.18 (2H, m), 3.37-3.66 (3H, m), 5.59 (1H, brs), 7.21 (1H, d, J=8.0 Hz), 7.50-7.60 (4H, m), 8.20-8.27 (2H, m),
melting point: 124-126° C. (recrystallized from ethyl acetate/diisopropyl ether),
MS (ESI+): 321 (M+H),
Elemental analysis: for C$_{20}$H$_{20}$N$_2$O$_2$
Calcd. (%): C, 74.98; H, 6.29; N, 8.74
Found (%): C, 74.86; H, 6.26; N, 8.83.

EXAMPLE 31

N-[2-(2-Benzyl-7,8-dihydro-6H-indeno[5,4-d][1,3]oxazol-8-yl)ethyl]acetamide

N-{3-[2-(Acetylamino)ethyl]-4-hydroxy-2,3-dihydro-1H-inden-5-yl}-2-phenylacetamide (29.0 mg, 0.0823 mmol) and pyridinium p-toluenesulfonate (4.1 mg, 0.0164 mmol) were heated under reflux in xylene (2 mL) for 2.5 hr. The solvent was evaporated under reduced pressure and the residue was purified by silica gel column chromatography (NH, ethyl acetate/hexane=30/70→60/40) to give the title compound (7.7 mg, yield 28%).

$^1$H-NMR (CDCl$_3$) δ: 1.73-1.91 (2H, m), 1.93 (3H, s), 2.07-2.21 (1H, m), 2.35-2.49 (1H, m), 2.87-3.14 (2H, m), 3.14-3.30 (1H, m), 3.37-3.52 (2H, m), 4.27 (2H, s), 5.45 (1H, brs), 7.15 (1H, d, J=8.0 Hz), 7.26-7.40 (5H, m), 7.47 (1H, d, J=8.0 Hz),

MS (ESI+): 335 (M+H).

EXAMPLE 32

N-{2-[2-(2-Phenylethyl)-7,8-dihydro-6H-indeno[5,4-d][1,3]oxazol-8-yl]ethyl}acetamide

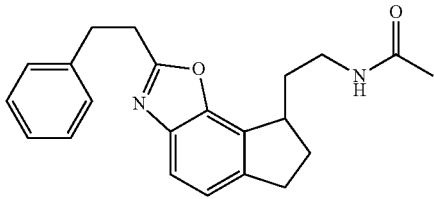 [SMILES: CC(=O)NCCC1CCc2ccc3nc(CCc4ccccc4)oc3c21]

N-{3-[2-(Acetylamino)ethyl]-4-hydroxy-2,3-dihydro-1H-inden-5-yl}-3-phenylpropanamide (72.5 mg, 0.198 mmol) and pyridinium p-toluenesulfonate (12.4 mg, 0.0493 mmol) were heated under reflux in xylene (5 mL) for 2.5 hr. The solvent was evaporated under reduced pressure and the residue was purified by silica gel column chromatography (NH, ethyl acetate/hexane=30/70→60/40) and recrystallized (ethyl acetate/diisopropyl ether) to give the title compound (19.8 mg, yield 29%).

$^1$H-NMR (CDCl$_3$) δ: 1.69-1.96 (2H, m), 1.98 (3H, s), 2.15-2.31 (1H, m), 2.35-2.50 (1H, m), 2.88-3.15 (2H, m), 3.16-3.39 (5H, m), 3.39-3.54 (2H, m), 5.49 (1H, brs), 7.16 (1H, d, J=8.0 Hz), 7.20-7.35 (5H, m), 7.47 (1H, d, J=8.0 Hz), melting point: 85-87° C. (recrystallized from ethyl acetate/diisopropyl ether),

MS (ESI+): 349 (M+H),

Elemental analysis: for C$_{22}$H$_{24}$N$_2$O$_2$

Calcd. (%): C, 75.83; H, 6.94; N, 8.04

Found (%): C, 75.54; H, 6.93; N, 8.10.

EXAMPLE 33

N-{2-[2-(3-Phenylpropyl)-7,8-dihydro-6H-indeno[5,4-d][1,3]oxazol-8-yl]ethyl}acetamide

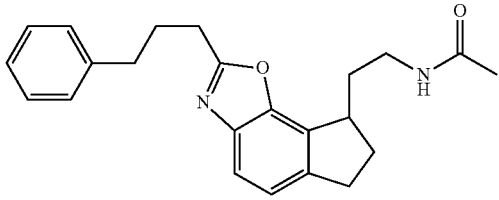 [SMILES: CC(=O)NCCC1CCc2ccc3nc(CCCc4ccccc4)oc3c21]

N-{3-[2-(Acetylamino)ethyl]-4-hydroxy-2,3-dihydro-1H-inden-5-yl}-4-phenylbutanamide (90.0 mg, 0.237 mmol) and pyridinium p-toluenesulfonate (11.9 mg, 0.0475 mmol) were heated under reflux in xylene (5 mL) for 2.5 hr. The solvent was evaporated under reduced pressure and the residue was purified by silica gel column chromatography (NH, ethyl acetate/hexane=30/70→60/40) and recrystallized (ethyl acetate/diisopropyl ether) to give the title compound (70.9 mg, yield 83%).

$^1$H-NMR (CDCl$_3$) δ: 1.70-1.94 (2H, m), 1.96 (3H, s), 2.16-2.33 (3H, m), 2.35-2.50 (1H, m), 2.77 (2H, t, J=7.4 Hz), 2.89-3.13 (4H, m), 3.27-3.55 (3H, m), 5.53 (1H, brs), 7.15 (1H, d, J=8.0 Hz), 7.17-7.35 (5H, m), 7.46 (1H, d, J=8.0 Hz), melting point: 95-97° C. (recrystallized from ethyl acetate/diisopropyl ether),

MS (ESI+): 363 (M+H),

Elemental analysis: for C$_{23}$H$_{26}$N$_2$O$_2$

Calcd. (%): C, 76.21; H, 7.23; N, 7.73

Found (%): C, 76.08; H, 7.20; N, 7.83.

EXAMPLE 34

N-(2-{2-[(Benzyloxy)methyl]-7,8-dihydro-6H-indeno[5,4-d][1,3]oxazol-8-yl}ethyl)acetamide

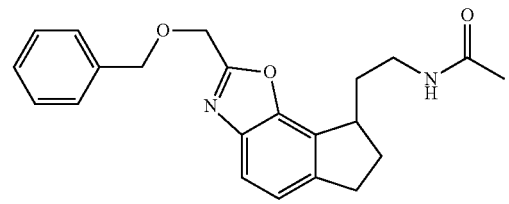 [SMILES: CC(=O)NCCC1CCc2ccc3nc(COCc4ccccc4)oc3c21]

N-{3-[2-(Acetylamino)ethyl]-4-hydroxy-2,3-dihydro-1H-inden-5-yl}-2-(benzyloxy)acetamide (280 mg, 0.732 mmol) and pyridinium p-toluenesulfonate (36.6 mg, 0.146 mmol) were heated under reflux in xylene (15 mL) for 2.5 hr. The solvent was evaporated under reduced pressure and the residue was purified by silica gel column chromatography (NH, ethyl acetate/hexane=30/70→60/40) to give the title compound (62.8 mg, yield 23%).

$^1$H-NMR (CDCl$_3$) δ: 1.75-1.94 (2H, m), 1.95 (3H, s), 2.20-2.34 (1H, m), 2.37-2.51 (1H, m), 2.93-3.15 (2H, m), 3.24-3.38 (1H, m), 3.41-3.58 (2H, m), 4.70 (2H, s), 4.78 (2H, s), 5.62 (1H, brs), 7.21 (1H, d, J=8.0 Hz), 7.28-7.42 (5H, m), 7.54 (1H, d, J=8.0 Hz),

MS (ESI+): 365 (M+H).

EXAMPLE 35

N-(2-{2-[4-(Benzyloxy)butyl]-7,8-dihydro-6H-indeno[5,4-d][1,3]oxazol-8-yl}ethyl)acetamide

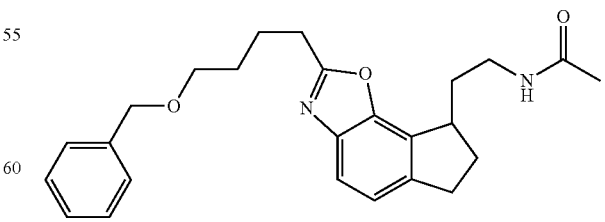

N-{3-[2-(Acetylamino)ethyl]-4-hydroxy-2,3-dihydro-1H-inden-5-yl}-5-(benzyloxy)pentanamide (100 mg, 0.236 mmol) and pyridinium p-toluenesulfonate (11.8 mg, 0.0471 mmol) were heated under reflux in xylene (5 mL) for 2.5 hr.

The solvent was evaporated under reduced pressure and the residue was purified by silica gel column chromatography (NH, ethyl acetate/hexane=30/70→60/40) to give the title compound (87.0 mg, yield 91%).

$^1$H-NMR (CDCl$_3$) δ: 1.70-1.93 (4H, m), 1.93-2.07 (5H, m), 2.18-2.32 (1H, m), 2.35-2.51 (1H, m), 2.89-3.14 (4H, m), 3.24-3.39 (1H, m), 3.40-3.58 (4H, m), 4.50 (2H, s), 5.55 (1H, brs), 7.14 (1H, d, J=8.0 Hz), 7.22-7.38 (5H, m), 7.45 (1H, dd, J=8.0, 0.8 Hz),

MS (ESI+): 407 (M+H).

EXAMPLE 36

N-(2-{2-[3-(Benzyloxy)butyl]-7,8-dihydro-6H-indeno[5,4-d][1,3]oxazol-8-yl}ethyl)acetamide

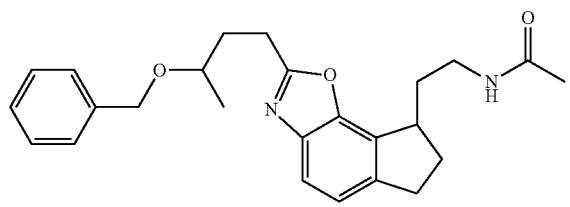 [SMILES: CC(=O)NCCC1CCc2ccc3nc(CCC(C)OCc4ccccc4)oc3c21]

N-{3-[2-(Acetylamino)ethyl]-4-hydroxy-2,3-dihydro-1H-inden-5-yl}-4-(benzyloxy)pentanamide (210 mg, 0.495 mmol) and pyridinium p-toluenesulfonate (24.8 mg, 0.0991 mmol) were heated under reflux in xylene (10 mL) for 14 hr. The solvent was evaporated under reduced pressure and the residue was purified by silica gel column chromatography (NH, ethyl acetate/hexane=30/70→60/40) to give the title compound (162 mg, yield 81%).

$^1$H-NMR (CDCl$_3$) δ: 1.28 (3H, d, J=6.0 Hz), 1.66-2.00 (5H, m), 2.01-2.32 (3H, m), 2.33-2.49 (1H, m), 2.87-3.16 (4H, m), 3.19-3.56 (3H, m), 3.62-3.74 (1H, m), 4.42 (1H, dd, J=11.6, 5.2 Hz), 4.59 (1H, dd, J=11.6, 5.7 Hz), 5.56 (1H, brs), 7.14 (1H, d, J=8.0 Hz), 7.18-7.34 (5H, m), 7.45 (1H, d, J=8.0 Hz),

MS (ESI+): 407 (M+H).

EXAMPLE 37

N-{2-[2-(4-Pyridin-2-ylbutyl)-7,8-dihydro-6H-indeno[5,4-d][1,3]oxazol-8-yl]ethyl}acetamide

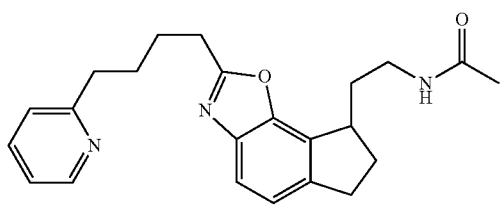 [SMILES: CC(=O)NCCC1CCc2ccc3nc(CCCCc4ccccn4)oc3c21]

N-{3-[2-(Acetylamino)ethyl]-4-hydroxy-2,3-dihydro-1H-inden-5-yl}-5-pyridin-2-ylpentanamide (37.7 mg, 0.0953 mmol) and pyridinium p-toluenesulfonate (4.8 mg, 0.0191 mmol) were heated under reflux in xylene (1 mL) for 1.5 hr. The solvent was evaporated under reduced pressure, washed with saturated aqueous sodium hydrogencarbonate solution and saturated brine and dried over anhydrous sodium sulfate. The solvent was evaporated under reduced pressure, and the residue was purified by silica gel column chromatography (NH, ethyl acetate/hexane=30/70→80/20) to give the title compound (20.9 mg, yield 58%).

$^1$H-NMR (CDCl$_3$) δ: 1.74-2.02 (6H, m), 1.96 (3H, s), 2.18-2.33 (1H, m), 2.35-2.51 (1H, m), 2.81-3.14 (6H, m), 3.25-3.40 (1H, m), 3.40-3.56 (2H, m), 5.94 (1H, brs), 7.06-7.19 (3H, m), 7.44 (1H, d, J=8.0 Hz), 7.58 (1H, td, J=7.7, 1.9 Hz), 8.42-8.53 (1H, m),

MS (ESI+): 378 (M+H).

EXAMPLE 38

N-[2-(2-Methoxy-7,8-dihydro-6H-indeno[5,4-d][1,3]oxazol-8-yl)ethyl]acetamide

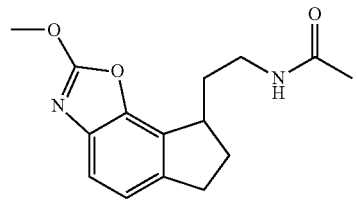 [SMILES: COc1nc2ccc3c(c2o1)C(CCNC(C)=O)CC3]

N-[2-(6-Amino-7-hydroxy-2,3-dihydro-1H-inden-1-yl)ethyl]acetamide hydrochloride (100 mg, 0.369 mmol) and tetramethoxymethane (151 mg, 1.11 mmol) were heated under reflux in tetrahydrofuran (3.7 mL) for 2 hr. The reaction solution was diluted with ethyl acetate and saturated aqueous sodium hydrogencarbonate solution, washed with saturated brine and dried over anhydrous sodium sulfate. The solvent was evaporated under reduced pressure, and the residue was purified by silica gel column chromatography (ethyl acetate/methanol=100/0→95/5) to give the title compound (58.4 mg, yield 58%).

$^1$H-NMR (CDCl$_3$) δ: 1.72-1.94 (2H, m), 1.98 (3H, s), 2.13-2.29 (1H, m), 2.31-2.48 (1H, m), 2.85-3.12 (2H, m), 3.23-3.37 (1H, m), 3.37-3.55 (2H, m), 4.21 (3H, s), 5.57 (1H, brs), 7.09 (1H, d, J=8.0 Hz), 7.29 (1H, d, J=8.0 Hz), melting point: 126-128° C. (recrystallized from ethyl acetate),

MS (ESI+): 275 (M+H),

Elemental analysis: for C$_{15}$H$_{18}$N$_2$O$_3$

Calcd. (%): C, 65.68; H, 6.61; N, 10.21

Found (%): C, 65.56; H, 6.48; N, 10.22.

EXAMPLE 39

N-{2-[2-(Methylthio)-7,8-dihydro-6H-indeno[5,4-d][1,3]oxazol-8-yl]ethyl}acetamide

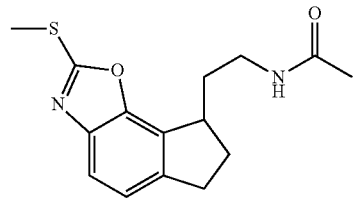

N-[2-(2-Mercapto-7,8-dihydro-6H-indeno[5,4-d][1,3]oxazol-8-yl)ethyl]acetamide (108 mg, 0.391 mmol) was dissolved in N,N-dimethylformamide (4 mL), iodomethane (48.6 μL, 0.782 mmol) and potassium carbonate (59.4 mg, 0.430 mmol) were added, and the mixture was stirred at room temperature for 15 min. The reaction solution was diluted with diethyl ether, washed with saturated aqueous sodium hydrogencarbonate solution and saturated brine and dried over anhydrous sodium sulfate. The solvent was evaporated under reduced pressure, and the residue was purified by silica gel column chromatography (ethyl acetate/hexane=50/50→100/0) to give the title compound (81.2 mg, yield 72%).

$^1$H-NMR (CDCl$_3$) δ: 1.72-1.94 (2H, m), 1.98 (3H, s), 2.16-2.34 (1H, m), 2.35-2.49 (1H, m), 2.76 (3H, s), 2.88-3.13 (2H, m), 3.27-3.54 (3H, m), 5.60 (1H, brs), 7.13 (1H, d, J=8.0 Hz), 7.40 (1H, d, J=8.0 Hz), melting point: 115-117° C. (recrystallized from hexane/ethyl acetate),

MS (ESI+): 291 (M+H),

Elemental analysis: for C$_{15}$H$_{18}$N$_2$O$_2$S

Calcd. (%): C, 62.04; H, 6.25; N, 9.65

Found (%): C, 61.80; H, 6.16; N, 9.49.

EXAMPLE 40

N-{2-[2-(Dimethylamino)-7,8-dihydro-6H-indeno[5,4-d][1,3]oxazol-8-yl]ethyl}acetamide

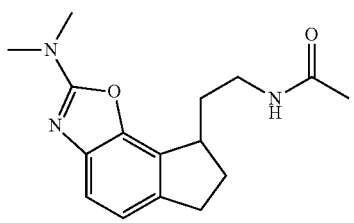 [SMILES: CC(=O)NCCC1CCc2ccc3nc(N(C)C)oc3c21]

N-[2-(6-Amino-7-hydroxy-2,3-dihydro-1H-inden-1-yl)ethyl]acetamide hydrochloride (100 mg, 0.369 mmol) was suspended in dichloromethane (3.7 mL), triethylamine (51.5 μg, 0.369 mmol) was added at room temperature, and the mixture was stirred for 15 min. Thereto was added dichloromethylenedimethyliminium chloride (59.9 mg, 0.369 mmol), and the mixture was heated under reflux for 1 hr. To the reaction solution was added saturated aqueous sodium hydrogencarbonate solution. The mixture was diluted with ethyl acetate, washed with saturated brine and dried over anhydrous sodium sulfate. The solvent was evaporated under reduced pressure, and the residue was purified by silica gel column chromatography (ethyl acetate/methanol=100/0→90/10) to give the title compound (7.4 mg, yield 7%).

$^1$H-NMR (CDCl$_3$) δ: 1.73-1.92 (2H, m), 1.96 (3H, s), 2.11-2.26 (1H, m), 2.30-2.45 (1H, m), 2.81-3.10 (2H, m), 3.20 (6H, s), 3.27-3.55 (3H, m), 5.50 (1 H, brs), 7.00 (1H, d, J=8.0 Hz), 7.16 (1H, d, J=8.0 Hz),

MS (ESI+): 288 (M+H).

EXAMPLE 41

1-Methyl-2-{[2-(2-methyl-7,8-dihydro-6H-indeno[5,4-d][1,3]oxazol-8-yl)ethyl]amino}-2-oxoethyl acetate

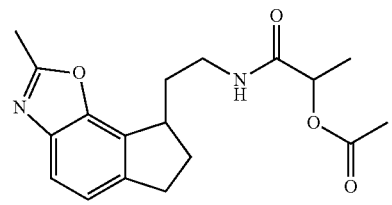 [SMILES: CC(=O)OC(C)C(=O)NCCC1CCc2ccc3nc(C)oc3c21]

2-(2-Methyl-7,8-dihydro-6H-indeno[5,4-d][1,3]oxazol-8-yl)ethanamine hydrochloride (150 mg, 0.593 mmol) and triethylamine (166 μL, 1.19 mmol) were dissolved in tetrahydrofuran (5 mL), 2-chloro-1-methyl-2-oxoethyl acetate (108 mg, 0.712 mmol) was added, and the mixture was stirred at room temperature for 30 min. The solvent was evaporated under reduced pressure, and the residue was purified by silica gel column chromatography (ethyl acetate/hexane=70/30→100/0) to give the title compound (78.4 mg, yield 40%).

$^1$H-NMR (CDCl$_3$) δ: 1.47 (3H, d, J=6.9 Hz), 1.73-1.99 (2H, m), 2.11-2.16 (3H, m), 2.18-2.32 (1H, m), 2.34-2.51 (1H, m), 2.63 (3H, s), 2.88-3.16 (2H, m), 3.27-3.59 (3H, m), 5.08-5.28 (1H, m), 6.25 (1H, brs), 7.15 (1H, d, J=8.0 Hz), 7.44 (1H, d, J=8.0 Hz),

MS (ESI+): 331 (M+H).

EXAMPLE 42

2-Hydroxy-N-[2-(2-methyl-7,8-dihydro-6H-indeno[5,4-d][1,3]oxazol-8-yl)ethyl]propanamide

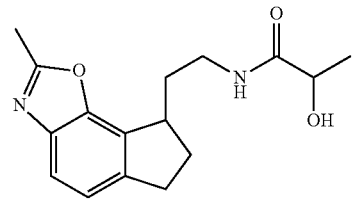 [SMILES: Cc1nc2ccc3c(c2o1)C(CCNC(=O)C(C)O)CC3]

To a solution of 1-methyl-2-{[2-(2-methyl-7,8-dihydro-6H-indeno[5,4-d][1,3]oxazol-8-yl)ethyl]amino}-2-oxoethyl acetate (70 mg, 0.212 mmol) in tetrahydrofuran (2 mL) was added 1N aqueous sodium hydroxide solution (2 mL), and the mixture was stirred at room temperature for 2 hr. The solvent was evaporated under reduced pressure. The residue was diluted with ethyl acetate, washed with saturated brine and dried over anhydrous sodium sulfate. The solvent was evaporated under reduced pressure, and the residue was purified by silica gel column chromatography (methanol/ethyl acetate) to give the title compound (52.4 mg, yield 86%).

$^1$H-NMR (CDCl$_3$) δ: 1.44 (3H, dd, J=6.7, 3.7 Hz), 1.73-1.99 (2H, m), 2.21-2.52 (3H, m), 2.63 (3H, s), 2.88-3.16 (2H, m), 3.30-3.60 (3H, m), 4.15-4.31 (1H, m), 6.60 (1H, brs), 7.14 (1H, d, J=8.0 Hz), 7.43 (1H, d, J=8.0 Hz),

MS (ESI+): 289 (M+H).

EXAMPLE 43

N-[2-(2-Methyl-7,8-dihydro-6H-indeno[5,4-d][1,3]oxazol-8-yl)ethyl]cyclopropanecarboxamide

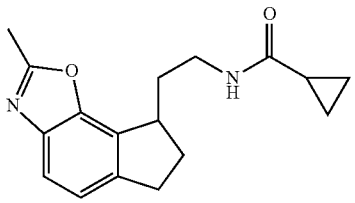 [SMILES: Cc1nc2ccc3c(c2o1)C(CCNC(=O)C1CC1)CC3]

2-(2-Methyl-7,8-dihydro-6H-indeno[5,4-d][1,3]oxazol-8-yl)ethanamine hydrochloride (100 mg, 0.396 mmol) and triethylamine (111 μL, 0.792 mmol) were dissolved in tetrahydrofuran (4 mL), cyclopropanecarbonyl chloride (43.1 μL, 0.475 mmol) was added under ice-cooling, and the mixture was stirred for 15 min. To the reaction solution was added saturated aqueous sodium hydrogencarbonate solution, and the solvent was evaporated under reduced pressure. The residue was purified by silica gel column chromatography (ethyl acetate/hexane=40/60→80/20) to give the title compound (47.6 mg, yield 42%).

$^1$H-NMR (CDCl$_3$) δ: 0.65-0.77 (2H, m), 0.90-1.02 (2H, m), 1.23-1.36 (1H, m), 1.70-1.98 (2H, m), 2.21-2.50 (2H, m), 2.63 (3H, s), 2.88-3.15 (2H, m), 3.30-3.59 (3H, m), 5.68 (1H, brs), 7.15 (1H, d, J=8.0 Hz), 7.44 (1H, d, J=8.0 Hz), melting point: 134-137° C. (recrystallized from hexane/ethyl acetate),

MS (ESI+): 285 (M+H),

Elemental analysis: for C$_{17}$H$_{20}$N$_2$O$_2$

Calcd. (%): C, 71.81; H, 7.09; N, 9.85

Found (%): C, 71.55; H, 7.07; N, 9.64.

EXAMPLE 44

N-[2-(2-Methyl-7,8-dihydro-6H-indeno[5,4-d][1,3]oxazol-8-yl)ethyl]benzamide

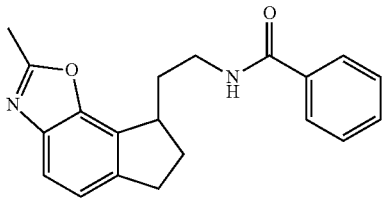 [SMILES: Cc1nc2ccc3c(c2o1)C(CCNC(=O)c1ccccc1)CC3]

2-(2-Methyl-7,8-dihydro-6H-indeno[5,4-d][1,3]oxazol-8-yl)ethanamine hydrochloride (100 mg, 0.396 mmol) and triethylamine (111 μL, 0.792 mmol) were dissolved in tetrahydrofuran (4 mL), benzoyl chloride (55.1 μL, 0.475 mmol) was added under ice-cooling, and the mixture was stirred for 15 min. To the reaction solution was added saturated aqueous sodium hydrogencarbonate solution, and the solvent was evaporated under reduced pressure. The residue was purified by silica gel column chromatography (ethyl acetate/hexane=20/80→60/40) to give the title compound (55.6 mg, yield 44%).

$^1$H-NMR (CDCl$_3$) δ: 1.88-2.05 (2H, m), 2.28-2.56 (2H, m), 2.61 (3H, s), 2.89-3.17 (2H, m), 3.47-3.64 (2H, m), 3.65-3.80 (1H, m), 6.25 (1H, brs), 7.16 (1H, d, J=8.0 Hz), 7.36-7.54 (4H, m), 7.66-7.78 (2H, m), melting point: 73-76° C. (recrystallized from hexane/ethyl acetate),

MS (ESI+): 321 (M+H).

EXAMPLE 45

2,2,2-Trifluoro-N-[2-(2-methyl-7,8-dihydro-6H-indeno[5,4-d][1,3]oxazol-8-yl)ethyl]acetamide

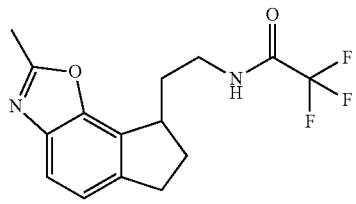 [SMILES: Cc1nc2ccc3c(c2o1)C(CCNC(=O)C(F)(F)F)CC3]

2-(2-Methyl-7,8-dihydro-6H-indeno[5,4-d][1,3]oxazol-8-yl)ethanamine hydrochloride (100 mg, 0.396 mmol) and triethylamine (111 μL, 0.792 mmol) were dissolved in tetrahydrofuran (4 mL), trifluoroacetic anhydride (82.1 μL, 0.594 mmol) was added under ice-cooling, and the mixture was stirred for 15 min. To the reaction solution was added saturated aqueous sodium hydrogencarbonate solution, and the solvent was evaporated under reduced pressure. The residue was purified by silica gel column chromatography (ethyl acetate/hexane=10/90→30/70) and recrystallized (hexane/ethyl acetate) to give the title compound (16.6 mg, yield 13%).

$^1$H-NMR (CDCl$_3$) δ: 1.82-2.01 (2H, m), 2.22-2.37 (1H, m), 2.38-2.53 (1H, m), 2.64 (3H, s), 2.90-3.18 (2H, m), 3.32-3.69 (3H, m), 6.46 (1H, brs), 7.16 (1H, d, J=8.0 Hz), 7.46 (1H, d, J=8.0 Hz), melting point: 104-106° C. (recrystallized from hexane/ethyl acetate),

MS (ESI+): 313 (M+H).

EXAMPLE 46

1-Ethyl-3-[2-(2-methyl-7,8-dihydro-6H-indeno[5,4-d][1,3]oxazol-8-yl)ethyl]urea

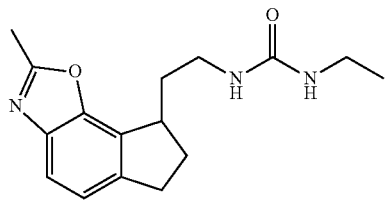 [SMILES: CCNC(=O)NCCC1CCc2ccc3nc(C)oc3c21]

2-(2-Methyl-7,8-dihydro-6H-indeno[5,4-d][1,3]oxazol-8-yl)ethanamine hydrochloride (156 mg, 0.617 mmol) and triethylamine (86.1 μL, 0.617 mmol) were dissolved in tetrahydrofuran (6.2 mL), ethyl isocyanate (58.6 μL, 0.741 mmol) was added under ice-cooling, and the mixture was stirred for 15 min. The solvent was evaporated under reduced pressure, and the residue was purified by silica gel column chromatography (ethyl acetate) to give the title compound (20.2 mg, yield 11%).

$^1$H-NMR (CDCl$_3$) δ: 1.15 (3H, t, J=7.1 Hz), 1.69-1.96 (2H, m), 2.20-2.34 (1H, m), 2.34-2.51 (1H, m), 2.63 (3H, s), 2.88-3.13 (2H, m), 3.14-3.58 (5H, m), 4.16 (1H, brs), 4.31 (1H, brs), 7.14 (1H, d, J=8.0 Hz), 7.44 (1H, d, J=8.0 Hz), melting point: 136-138° C. (recrystallized from ethyl acetate),

MS (ESI+): 288 (M+H).

EXAMPLE 47

N-[2-(2-Mercapto-7,8-dihydro-6H-indeno[5,4-d][1,3]oxazol-8-yl)ethyl]acetamide

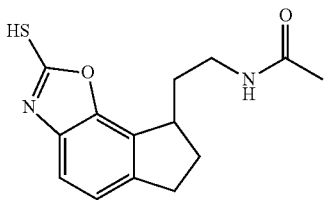 [SMILES: CC(=O)NCCC1CCc2ccc3nc(S)oc3c21]

N-[2-(6-Amino-7-hydroxy-2,3-dihydro-1H-inden-1-yl)ethyl]acetamide hydrochloride (100 mg, 0.369 mmol) and potassium O-ethyl dithiocarbonate (65.1 mg, 0.406 mmol) were heated under reflux in pyridine (1 mL) for 2 hr. The reaction solution was diluted with ethyl acetate, washed with 1N hydrochloric acid and saturated brine and dried over anhydrous sodium sulfate. The solvent was evaporated under reduced pressure, and the residue was purified by silica gel column chromatography (ethyl acetate/methanol=100/0→90/10) to give the title compound (64.8 mg, yield 64%).

$^1$H-NMR (DMSO-d$_6$) δ: 1.42-1.60 (1H, m), 1.68-1.79 (1H, m), 1.79 (3H, s), 2.13-2.37 (2H, m), 2.76-3.01 (2H, m), 3.10-3.20 (2H, m), 3.34-3.45 (1H, m), 7.00 (1H, d, J=7.7 Hz), 7.13 (1H, d, J=7.7 Hz), 7.92 (1H, brs), hidden (1H),

MS (ESI+): 277 (M+H).

EXAMPLE 48

N-[2-(8-Hydroxy-7-isopropyl-2-methyl-7,8-dihydro-6H-indeno[5,4-d][1,3]oxazol-8-yl)ethyl]acetamide

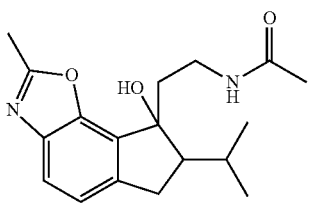 [SMILES: CC(=O)NCCC1(O)c2c(ccc3nc(C)oc23)CC1C(C)C]

To a solution of (8-hydroxy-7-isopropyl-2-methyl-7,8-dihydro-6H-indeno[5,4-d][1,3]oxazol-8-yl)acetonitrile (584 mg, 2.16 mmol) in ethanol (11 mL) were added Raney cobalt (5.84 g) and 2M ammonia/ethanol solution (11 mL), and the mixture was stirred at room temperature for 24 hr under a hydrogen atmosphere. The catalyst was filtered off using celite, and the filtrate was concentrated under reduced pressure. The residue was dissolved in tetrahydrofuran (11 mL), triethylamine (82.9 μL, 0.594 mmol) and acetic anhydride (51.0 μL, 0.540 mmol) were added under ice-cooling, and the mixture was stirred for 5 min. To the reaction solution was added saturated aqueous sodium hydrogencarbonate solution, and the solvent was evaporated under reduced pressure. The residue was purified by silica gel column chromatography (methanol/ethyl acetate=0/100→10/90) to give the title compound (132 mg, yield 19%).

$^1$H-NMR (CDCl$_3$) δ: 0.80 (3H, d, J=6.6 Hz), 1.10 (3H, d, J=6.9 Hz), 1.91 (3H, s), 2.10-2.42 (4H, m), 2.65 (3H, s), 2.87-2.98 (1H, m), 3.00-3.13 (1H, m), 3.21-3.38 (1H, m), 3.39-3.54 (1H, m), 5.90 (1H, brs), 7.12 (1H, d, J=8.0 Hz), 7.51 (1H, d, J=8.0 Hz), hidden (1H),

MS (ESI+): 317 (M+H).

EXAMPLE 49

N-[2-(7-Isopropyl-2-methyl-6H-indeno[5,4-d][1,3]oxazol-8-yl)ethyl]acetamide

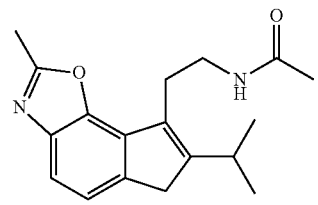 [SMILES: CC(=O)NCCC1=C(C(C)C)Cc2ccc3nc(C)oc3c21]

To a solution of N-[2-(8-hydroxy-7-isopropyl-2-methyl-7,8-dihydro-6H-indeno[5,4-d][1,3]oxazol-8-yl)ethyl]acetamide (132 mg, 0.417 mmol) in toluene (4.2 mL) were added p-toluenesulfonic acid monohydrate (396 mg, 2.08 mmol) and magnesium sulfate (1 g), and the mixture was stirred at 100° C. for 1 hr. The reaction solution was diluted with ethyl acetate, washed with saturated aqueous sodium hydrogencarbonate solution and saturated brine and dried over anhydrous sodium sulfate. The solvent was evaporated under reduced pressure, and the residue was purified by silica gel column chromatography (NH, ethyl acetate/hexane=30/70→100/0) to give the title compound (76.1 mg, yield 61%).

$^1$H-NMR (CDCl$_3$) δ: 1.20 (6H, d, J=6.9 Hz), 1.90 (3H, s), 2.67 (3H, s), 2.97 (2H, t, J=6.3 Hz), 3.03-3.15 (1H, m), 3.46 (2H, s), 3.56-3.66 (2H, m), 5.56 (1H, brs), 7.35 (1H, d, J=8.0 Hz), 7.41 (1H, d, J=8.0 Hz), melting point: 135-138° C. (recrystallized from ethyl acetate/hexane),

MS (ESI+): 299 (M+H),

Elemental analysis: for C$_{18}$H$_{22}$N$_2$O$_2$

Calcd. (%): C, 72.46; H, 7.43; N, 9.39

Found (%): C, 72.42; H, 7.54; N, 9.41.

FORMULATION EXAMPLE 1

| (1) | Compound obtained in Example 1 | 10.0 g |
| (2) | Lactose | 60.0 g |
| (3) | Cornstarch | 35.0 g |
| (4) | Gelatin | 3.0 g |
| (5) | Magnesium stearate | 2.0 g |

A mixture of the compound (10.0 g) obtained in Example 1, lactose (60.0 g) and cornstarch (35.0 g) is granulated using 10 wt % aqueous gelatin solution (30 mL) (3.0 g as gelatin) by passing a 1 mm mesh sieve, dried at 40° C. and sieved again. The obtained granules are mixed with magnesium stearate (2.0 g) and the mixture is compressed. The obtained core tablets are coated with a sugar coating using an aqueous suspension of saccharose, titanium dioxide, talc and gum arabic. The coated tablets are glazed with bees wax to give 1000 coated tablets.

FORMULATION EXAMPLE 2

| (1) | Compound obtained in Example 1 | 10.0 g |
|---|---|---|
| (2) | Lactose | 70.0 g |
| (3) | Cornstarch | 50.0 g |
| (4) | Soluble starch | 7.0 g |
| (5) | Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

EXPERIMENTAL EXAMPLE 1

Melatonin Receptor Binding Assay
(1) Preparation of CHO-hMelR7 Cells Expressing Human Melatonin 1 Receptors A cDNA fragment (SEQ ID NO: 1) encoding full-length of human melatonin 1 receptors (human $MT_1$ receptors) was incorporated into expression vector pAKKO-111H (former name pAKKO1.11H; Biochim Biophys Acta. Vol. 1219(2), pp. 251-259, 1994) to give plasmid pAKKO-hMelR7 for animal cell expression. CHO/dhfr-cells (ATCC, #CRL-9096) were plated at a concentration of $0.3 \times 10^6$ cells/dish in a 6 cm culture dish (Becton Dickinson), and cultured under the conditions of 37° C., 5% $CO_2$ for 48 hr. The cells were transfected with pAKKO-hMelR7 plasmid DNA (5 μg) using Cellphect Transfection Kit (Amersham, #27-9268-01). The transfected cells were cultured in Dulbecco's modified Eagle medium (DMEM) (Sigma, #D6046) containing 10% dialyzed FBS (Biowest, #S180D), 1× Non-Essential Amino Acid (Invitrogen, #11140-050) and 50 μg/mL Gentamycin (Invitrogen, #15750-060), and the cell line that stably expressed the plasmid gene was selected. By a receptor binding assay using 2-[$^{125}$I] Iodomelatonin, CHO-hMelR7 cell line showing specific binding of 2-[$^{125}$I] Iodomelatonin was selected from the obtained clones.
(2) Preparation of CHO-hMT2 Cells Expressing Human Melatonin 2 Receptors A cDNA fragment (SEQ ID NO: 2) encoding full-length of human melatonin 2 receptors (human $MT_2$ receptors) was incorporated into expression vector pCMV-Script (Stratagene, #212220) to give the plasmid that was pCMV-human MT2 receptors expression vector for animal cell expression. CHO-K1 cells (ATCC, #CCL-61) were plated at the concentration of $1.5 \times 10^5$ cells/cm$^2$ in a 6 well plate (ASAHI TECHNO GLASS), and cultured under the conditions of 37° C., 5% $CO_2$ for 24 hr. For gene transfection, solution obtained by blending pCMV-human MT2 receptors expression vector (1.9 μg), Lipofectamine Transfection Reagent (Invitrogen, #18324-012) (11.3 μL) and Minimum Essential Medium Eagle (MEM) medium (Sigma, M8042) (93.8 μL), and reacting at room temperature for 20 min was added to the cells per one well. The transfected cells were cultured in MEM medium containing 10% FBS (Life Technology) and 300 μg/mL Geneticin (GIBCO, #10131), and the cell line that stably expressed the plasmid gene was selected. By a receptor binding assay using 2-[$^{125}$I] Iodomelatonin, CHO-hMT2 cell line showing specific binding of 2-[$^{125}$I] Iodomelatonin was selected from the obtained clones.
(3) Preparation of Cell Membrane Fraction of CHO Cell (CHO-hMelR7 and CHO-hMT2) Stably Expressing Human $MT_1$ and $MT_2$ Receptors CHO-hMelR7 and CHO-hMT2 cells were plated using Cellfactory (Nunc, #170009) under the conditions of $1 \times 10^8$ cells/2000 mL/flask. The cells were grown to confluent, and recovered by the following method. As the medium for CHO-hMelR7 and CHO-hMT2, MEM α containing 10% FBS and penicillin/streptomycin was used. 300 ng/mL of geneticin was added to the medium for CHO-hMT2.

The medium was discarded, cells were washed twice with 200 mL of EDTA/PBS(−), 200 mL of EDTA/PBS(−) was further added, and the cells were stood still at room temperature for 20 min until they were released. The cells were recovered in four 50 mL tubes (Becton Dickinson, #352070), and centrifuged at 1,500 rpm for 10 min at 4° C. using a low speed cooling centrifuge (Hitachi, CF7D2). The supernatant was discarded, the pellets in the four tubes were suspended in 10 mL of PBS(−), and combined in one tube (Becton Dickinson, #352070). The mixture was further centrifuged at 1,500 rpm for 10 min at 4° C., and the obtained pellets were suspended in 20 mL of ice-cooled homogenizing buffer [10 mM $NaHCO_3$, 5 mM EDTA, Protease inhibitor Complete (Roche), pH 7.4]. The cell suspension was homogenized 3 times using a polytron homogenizer at 20,000 rpm for 30 sec. The obtained homogenate was centrifuged (2,000 rpm, 10 min, 4° C.) using a low speed cooling centrifuge. The supernatant was recovered in an ultracentrifugation tube and ultracentrifuged (40,000 rpm, 60 min, 4° C.) using an ultracentrifuge (Beckman, L-90K). To the obtained pellets was added a suspending buffer [50 mM Tris-HCl, 1 mM EDTA, Protease inhibitor Complete (Roche), pH 7.4], and the pellets were suspended by pipetting. The protein concentration of this suspension was measured, diluted to 2 mg/mL to give cell membrane fractions of CHO-hMelR7 and CHO-hMT2 cells. The membrane fractions were dispensed to 1.5 mL tubes (Eppendorf, #0030120.086) by 100 μL, preserved in a freezer (−80° C.) and used for a binding assay. Protein was quantified using BCA protein assay kit (Pierce) with BSA as the standard.
(4) Preparation of Membrane Fraction Suspension Immediately before use, the membrane fractions of CHO-hMelR7 and CHO-hMT2 cells of the above-mentioned (3) were diluted 20-fold with assay buffer (50 mM Tris-HCl, pH 7.7).
(5) Preparation of 2-[$^{125}$I] Iodomelatonin Solution 2-[$^{125}$I] Iodomelatonin (#NEX236, PerkinElmer) was diluted with the assay buffer to 400 pM for $MT_1$ and 1 nM for $MT_2$.
(6) Binding Reaction The assay buffer (80 μL) of the above-mentioned (4) was added to each well of a 96-well plate (type 3363, Corning). Then, a test compound (compound solution diluted with DMSO to 200-fold of the final measurement concentration) was added by 2 μL. 2 μL of DMSO was added to each well of the total binding control section, and 100 μM cold Melatonin solution (Sigma, diluted with DMSO to 100 μM) was added to each well of the nonspecific binding control section by 2 μL. Then, the membrane fraction suspension (100 μL) was added. 2-[$^{125}$I] Iodomelatonin solution of the above-mentioned (5) was added to each well mentioned above by 20 μL, and a binding reaction was carried out at 25° C. for 2.5 hr in a micromixer (TAITEC, Bioshaker M.BR-024).

(7) Measurement

Using a cell harvester (PerkinElmer), the binding reaction mixture in each well of the 96-well plate was transferred to a treated (immersed in 50 mM Tris, pH 7.7 in advance) filter plate (UniFilter GF/C, PerkinElmer) and filtered. After filtration, the plate was washed 4 times with the assay buffer, and dried in a dryer (42° C.) for 2 hr or more. 25 µL of a liquid scintillator (MicroScint O, PerkinElmer) was added to each well of the filter plate after drying, and the luminescence of scintillator was measured by TopCount (PerkinElmer) for 1 min.

Specific binding is a value obtained by subtracting nonspecific binding from the total binding. The binding inhibitory activity of the test compound is shown by the ratio of the value obtained by subtracting the measurement value when the test compound was added from the total binding, to the specific binding. The compound concentration ($IC_{50}$ value) showing 50% of binding inhibitory activity was calculated from the dose reaction curve. The results are shown in Table 1.

TABLE 1

| Example compound | $MT_1$ ($IC_{50}$, nM) | $MT_2$ ($IC_{50}$, nM) |
|---|---|---|
| 3 | 0.33 | 0.37 |
| 4 | 0.068 | 0.24 |
| 5 | 0.25 | 0.22 |
| 6 | 0.079 | 0.43 |
| 8 | 0.19 | 0.22 |
| 9 | 0.88 | 0.31 |
| 11 | 0.15 | 0.31 |
| 12 | 0.057 | 0.13 |
| 13 | 15 | 9.6 |
| 14 | 0.13 | 0.28 |
| 15 | 0.030 | 0.049 |
| 16 | 11 | 6.2 |
| 17 | 0.022 | 0.091 |
| 19 | 0.15 | 0.28 |
| 20 | 0.038 | 0.12 |
| 21 | 19 | 8.5 |
| 22 | 0.36 | 0.41 |
| 29 | 0.66 | 0.75 |
| 38 | 0.54 | 0.28 |
| 43 | 0.25 | 0.77 |
| 45 | 0.095 | 0.14 |

From the results of Table 1, it is known that compound (I) has superior melatonin receptor agonist activity.

EXPERIMENTAL EXAMPLE 2

In Vitro Metabolic Stability Test
(1) Preparation of Analysis Sample

The necessary amounts of the analysis samples were prepared at the following composition ratio. Test compound mixture: 0.1 mol/L phosphate buffer (pH 7.4) (41 µL), control microsome (manufactured by Gentest, human lymphoblastoid cell-derived control microsome, 10 mg protein/mL) (8 µL), and test compound 0.1 mM methanol solution (1 µL). Microsome mixed solution: 0.1 mol/L phosphate buffer (pH 7.4) (9 µL), human liver microsome (manufactured by XENOTECH, H0610, 20 mg protein/mL) (1 µL), and purified water (20 µL). NADPH production system: 50 mmol/L β-NADP+ (200 µL), 500 mmol/L Glucose-6-phosphate (200 µL), 150 unit/mL Glucose-6-phosphate dehydrogenase (200 µL), 0.1 mol/L $MgCl_2$ (1 mL), and purified water (2.4 mL).
(2) Reaction Test Microsome mixed solution (30 µL) and NADPH production system (20 µL) were sequentially dispensed to each well of a 96 well plate (type 3371, Corning), and a test compound mixture (50 µL) was added. Acetonitrile (100 µL) was added before start of incubation at 37° C. or 20 min later to give samples before and after incubation. These samples were centrifuged (3,000 rpm, 10 min), and the supernatant was dispensed to a 96 well plate by about 100 µL and 2-fold diluted with purified water (100 µL). 90 µL thereof was analyzed by HPLC.

HPLC analysis Conditions
Instrument: Shimadzu LC10vp
Column: CAPCELL PAK C18 MGII (4.6×75 mm, 3 µm)
Mobile phase A: 10 mmol/L ammonium acetate:acetonitrile=9:1
Mobile phase B: 10 mmol/L ammonium acetate:acetonitrile=1:9
Flow rate: 1 mL/min
Column temperature: 40° C.
Detection: UV (250 nm)
Gradient:

| Time (min) | Mobile phase B (%) |
|---|---|
| 0 | 25 |
| 8.5 | 100 |
| 12.5 | 100 |
| 12.51 | 25 |
| 17 | 25 |
| | (termination) |

(3) Data Analysis and Results

Elimination percentage was determined from the difference in the unchanged compound peak areas before and after the start of the reaction, normalized based on the reaction time and microsome concentration, and the elimination rate (%/min/mg) was calculated. The results are shown in Table 2.

TABLE 2

| Example compound | elimination rate (%/min/mg) |
|---|---|
| 12 | −0.3 |
| 15 | 2.6 |
| 19 | 2.4 |
| 20 | 2.7 |
| 38 | 2.6 |

From the results of Table 2, it is known that compound (I) has superior metabolic stability.

This application is based on application No. 2006-168518 filed in Japan, the contents of which are incorporated hereinto by reference.

The invention claimed is:
1. A compound represented by the formula:

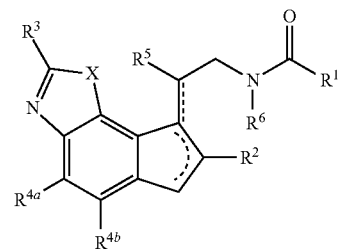

wherein
R¹ is a hydrocarbon group optionally having substituent(s), amino optionally having substituent(s), hydroxy optionally having a substituent or a heterocyclic group optionally having substituent(s);

R² is a hydrogen atom, a halogen atom, a hydrocarbon group optionally having substituent(s) or a heterocyclic group optionally having substituent(s);

R³ is a hydrogen atom, a hydrocarbon group optionally having substituent(s), amino optionally having substituent(s), hydroxy optionally having a substituent, mercapto optionally having a substituent or a heterocyclic group optionally having substituent(s);

$R^{4a}$ and $R^{4b}$ are the same or different and each is a hydrogen atom, a halogen atom, a hydrocarbon group optionally having substituent(s), amino optionally having substituent(s), hydroxy optionally having a substituent or mercapto optionally having a substituent;

R⁵ is a hydrogen atom, a halogen atom, a hydrocarbon group optionally having substituent(s), amino optionally having substituent(s), hydroxy optionally having a substituent or mercapto optionally having a substituent;

R⁶ is a hydrogen atom or a hydrocarbon group optionally having substituent(s);

X is an oxygen atom or a sulfur atom; and

----- shows a single bond or a double bond, or a pharmaceutically acceptable salt or prodrug thereof.

2. The compound of claim 1, which is represented by the formula:

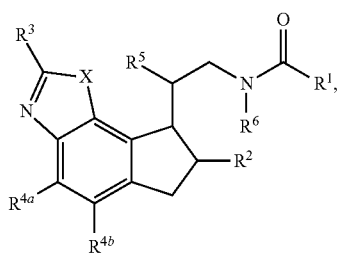

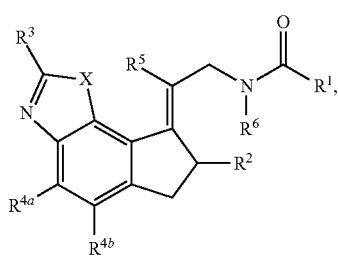

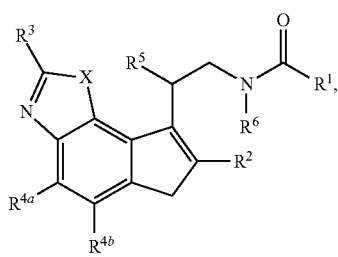

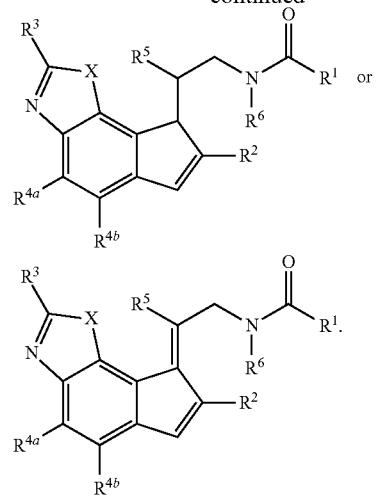

3. The compound of claim 1, wherein R¹ is $C_{1-6}$ alkyl optionally having substituent(s), $C_{3-6}$ cycloalkyl optionally having substituent(s) or $C_{2-6}$ alkenyl optionally having substituent(s).

4. The compound of claim 1, wherein R⁵ is a hydrogen atom or $C_{1-6}$ alkyl optionally having substituent(s).

5. The compound of claim 1, wherein R⁶ is a hydrogen atom or $C_{1-6}$ alkyl optionally having substituent(s).

6. The compound of claim 1, wherein R² is a hydrogen atom, a hydrocarbon group optionally having substituent(s) or a heterocyclic group optionally having substituent(s).

7. The compound of claim 1, wherein R³ is a hydrogen atom, $C_{1-6}$ alkyl optionally having substituent(s), $C_{2-6}$ alkenyl optionally having substituent(s) or amino optionally having substituent(s).

8. The compound of claim 1, wherein $R^{4a}$ and $R^{4b}$ are the same or different and each is a hydrogen atom, a halogen atom, hydroxy optionally having a substituent or $C_{1-6}$ alkyl optionally having substituent(s).

9. The compound of claim 1, wherein R¹ is $C_{1-6}$ alkyl optionally having substituent(s), $C_{3-6}$ cycloalkyl optionally having substituent(s) or $C_{2-6}$ alkenyl optionally having substituent(s);

R² is a hydrogen atom, a hydrocarbon group optionally having substituent(s) or a heterocyclic group optionally having substituent(s);

R³ is a hydrogen atom, $C_{1-6}$ alkyl optionally having substituent(s), $C_{2-6}$ alkenyl optionally having substituent(s) or amino optionally having substituent(s);

$R^{4a}$ and $R^{4b}$ are the same or different and each is a hydrogen atom, a halogen atom, hydroxy optionally having a substituent or $C_{1-6}$ alkyl optionally having substituent(s);

R⁵ is a hydrogen atom or $C_{1-6}$ alkyl optionally having substituent(s); and

R⁶ is a hydrogen atom or $C_{1-6}$ alkyl optionally having substituent(s).

10. The compound of claim 1, wherein R¹ is $C_{1-6}$ alkyl optionally having substituent(s);

R² is a hydrogen atom;

R³ is a hydrogen atom or $C_{1-6}$ alkyl optionally having substituent(s);

$R^{4a}$ and $R^{4b}$ are the same or different and each is a hydrogen atom or a halogen atom;

R⁵ is a hydrogen atom or $C_{1-6}$ alkyl optionally having substituent(s); and

R⁶ is a hydrogen atom.

11. A compound represented by the formula:

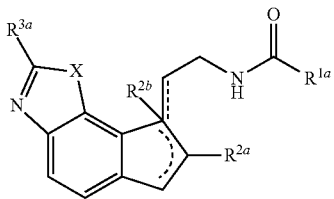

wherein $R^{1a}$ is (a) $C_{1-6}$ alkyl optionally having 1 to 3 substituents selected from $C_{1-6}$ alkyl-carbonyloxy, hydroxy and a halogen atom, (b) $C_{3-6}$ cycloalkyl, (c) phenyl or (d) mono- or di-$C_{1-6}$ alkylamino;

$R^{2a}$ is a hydrogen atom or $C_{1-6}$ alkyl;

$R^{2b}$ is a hydrogen atom or hydroxy;

$R^{3a}$ is (a) a hydrogen atom, (b) $C_{1-6}$ alkyl optionally having 1 to 3 substituents selected from phenyl, hydroxy, a halogen atom, $C_{1-6}$ alkyl-carbonyl, $C_{7-13}$ aralkyloxy and pyridyl, (c) $C_{3-6}$ cycloalkyl, (d) phenyl, (e) $C_{1-6}$ alkoxy, (f) mercapto, (g) $C_{1-6}$ alkylthio or (h) mono- or di-$C_{1-6}$ alkylamino;

X is an oxygen atom or a sulfur atom; and

___ shows a single bond or a double bond, or a pharmaceutically acceptable salt thereof.

12. The compound of claim 1 which is selected from the group consisting of:

N-[2-(2-methyl-6,7-dihydro-8H-indeno[5,4-d][1,3]oxazol-8-ylidene)ethyl]acetamide, N-[2-(2-methyl-6H-indeno[5,4-d][1,3]oxazol-8-yl)ethyl]acetamide, N-[2-(2-methyl-6,7-dihydro-8H-indeno[5,4-d][1,3]oxazol-8-ylidene)ethyl]propionamide, N-{2-[2-(4-phenylbutyl)-6,7-dihydro-8H-indeno[5,4-d][1,3]oxazol-8-ylidene]ethyl}acetamide, N-[2-(2-methyl-6,7-dihydro-8H-indeno[5,4-d][1,3]thiazol-8-ylidene)ethyl]acetamide, N-[2-(2-methyl-7,8-dihydro-6H-indeno[5,4-d][1,3]oxazol-8-yl)ethyl]acetamide, (R)-N-[2-(2-methyl-7,8-dihydro-6H-indeno[5,4-d][1,3]oxazol-8-yl)ethyl]acetamide, (S)-N-[2-(2-methyl-7,8-dihydro-6H-indeno[5,4-d][1,3]oxazol-8-yl)ethyl]acetamide, N-[2-(2-methyl-7,8-dihydro-6H-indeno[5,4-d][1,3]oxazol-8-yl)ethyl]propionamide, (R)-N-[2-(2-methyl-7,8-dihydro-6H-indeno[5,4-d][1,3]oxazol-8-yl)ethyl]propionamide, (S)-N-[2-(2-methyl-7,8-dihydro-6H-indeno[5,4-d][1,3]oxazol-8-yl)ethyl]propionamide, N-[2-(2-methyl-7,8-dihydro-6H-indeno[5,4-d][1,3]thiazol-8-yl)ethyl]acetamide, (R)-N-[2-(2-methyl-7,8-dihydro-6H-indeno[5,4-d][1,3]thiazol-8-yl)ethyl]acetamide, (S)-N-[2-(2-methyl-7,8-dihydro-6H-indeno[5,4-d][1,3]thiazol-8-yl)ethyl]acetamide, N-[2-(2-ethyl-7,8-dihydro-6H-indeno[5,4-d][1,3]oxazol-8-yl)ethyl]acetamide, (R)-N-[2-(2-ethyl-7,8-dihydro-6H-indeno[5,4-d][1,3]oxazol-8-yl)ethyl]acetamide, (S)-N-[2-(2-ethyl-7,8-dihydro-6H-indeno[5,4-d][1,3]oxazol-8-yl)ethyl]acetamide, N-[2-(2-methoxy-7,8-dihydro-6H-indeno[5,4-d][1,3]oxazol-8-yl)ethyl]acetamide, (R)-N-[2-(2-methoxy-7,8-dihydro-6H-indeno[5,4-d][1,3]oxazol-8-yl)ethyl]acetamide, and (S)-N-[2-(2-methoxy-7,8-dihydro-6H-indeno[5,4-d][1,3]oxazol-8-yl)ethyl]acetamide, or a pharmaceutically acceptable salt thereof.

13. A prodrug of the compound of claim 1.

14. A pharmaceutical composition comprising the compound of claim 1, and a pharmaceutically acceptable carrier.

15. A compound represented by the formula:

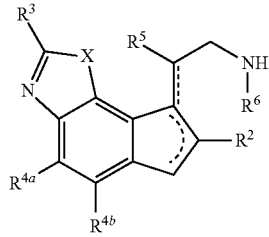

wherein $R^2$ is a hydrogen atom, a halogen atom, a hydrocarbon group optionally having substituent(s) or a heterocyclic group optionally having substituent(s);

$R^3$ is a hydrogen atom, a hydrocarbon group optionally having substituent(s), amino optionally having substituent(s), hydroxy optionally having a substituent, mercapto optionally having a substituent or a heterocyclic group optionally having substituent(s);

$R^{4a}$ and $R^{4b}$ are the same or different and each is a hydrogen atom, a halogen atom, a hydrocarbon group optionally having substituent(s), amino optionally having substituent(s), hydroxy optionally having a substituent or mercapto optionally having a substituent;

$R^5$ is a hydrogen atom, a halogen atom, a hydrocarbon group optionally having substituent(s), amino optionally having substituent(s), hydroxy optionally having a substituent or mercapto optionally having a substituent;

$R^6$ is a hydrogen atom or a hydrocarbon group optionally having substituent(s);

X is an oxygen atom or a sulfur atom; and

----- shows a single bond or a double bond, or a pharmaceutically acceptable salt thereof.

16. A method for treating a sleep disorder in a mammal, comprising administering an effective amount of the compound of claim 1 to the mammal.

17. A method for treating depression, anxiety or bipolar disorder in a mammal, comprising administering an effective amount of the compound of claim 1 to the mammal.

\* \* \* \* \*